US007024312B1

(12) United States Patent
Selifonov et al.

(10) Patent No.: US 7,024,312 B1
(45) Date of Patent: Apr. 4, 2006

(54) METHODS FOR MAKING CHARACTER STRINGS, POLYNUCLEOTIDES AND POLYPEPTIDES HAVING DESIRED CHARACTERISTICS

(75) Inventors: Sergey A. Selifonov, Los Altos, CA (US); Willem P. C. Stemmer, Los Gatos, CA (US); Claes Gustafsson, Belmont, CA (US); Matthew Tobin, San Jose, CA (US); Stephen del Cardayre, Belmont, CA (US); Phillip A. Patten, Menlo Park, CA (US); Jeremy Minshull, Menlo Park, CA (US); Lorraine J. Giver, Sunnyvale, CA (US)

(73) Assignee: Maxygen, Inc., Redwood City, CA (US)

( * ) Notice: Subject to any disclaimer, the term of this patent is extended or adjusted under 35 U.S.C. 154(b) by 0 days.

(21) Appl. No.: 09/618,579

(22) Filed: Jul. 18, 2000

Related U.S. Application Data

(63) Continuation-in-part of application No. 09/539,486, filed on Mar. 30, 2000, which is a continuation-in-part of application No. 09/494,282, filed on Jan. 18, 2000, which is a continuation-in-part of application No. PCT/US00/01202, filed on Jan. 18, 2000, which is a continuation-in-part of application No. 09/416,375, filed on Oct. 12, 1999, now abandoned, said application No. 09/539,486 is a continuation-in-part of application No. 09/484,850, filed on Jan. 18, 2000, now Pat. No. 6,368,861, and a continuation-in-part of application No. PCT/US00/01203, filed on Feb. 18, 2000, which is a continuation-in-part of application No. 09/408,392, filed on Sep. 28, 1999, now Pat. No. 6,376,246, and application No. 09/539,486, Mar. 30, 2000, and a continuation-in-part of application No. PCT/US00/01138, filed on Jan. 18, 2000, which is a continuation-in-part of application No. 09/416,837, filed on Oct. 12, 1999, now abandoned.

(60) Provisional application No. 60/141,049, filed on Jun. 24, 1999, provisional application No. 60/118,813, filed on Feb. 5, 1999, provisional application No. 60/118,854, filed on Feb. 5, 1999, provisional application No. 60/116,447, filed on Jan. 19, 1999.

(51) Int. Cl.
G01N 33/48 (2006.01)
C12Q 1/00 (2006.01)
C12Q 1/68 (2006.01)
C07H 21/02 (2006.01)
C07K 1/00 (2006.01)

(52) U.S. Cl. .............................. 702/19; 702/20; 435/4; 435/6; 435/15; 435/91.2; 536/23.1; 536/24.1; 530/300; 530/350

(58) Field of Classification Search .................... 435/6, 435/15, 91.2, 91.1, 192, 197, 4; 536/23.1, 536/24.1; 530/300, 350; 702/19, 20
See application file for complete search history.

(56) References Cited

U.S. PATENT DOCUMENTS

| | | |
|---|---|---|
| 4,959,312 A | 9/1990 | Sirotkin |
| 4,994,379 A | 2/1991 | Chang |
| 5,023,171 A | 6/1991 | Ho et al. |
| 5,043,272 A | 8/1991 | Hartley et al. |
| 5,066,584 A | 11/1991 | Gyllensten et al. |
| 5,198,346 A | 3/1993 | Ladner et al. |
| 5,223,409 A | 6/1993 | Ladner et al. |
| 5,264,563 A | 11/1993 | Huse |
| 5,319,308 A | 6/1994 | Dechene et al. |
| 5,408,181 A | 4/1995 | Dechene et al. |
| 5,447,839 A | 9/1995 | Manos et al. |
| 5,506,793 A | 4/1996 | Straayer et al. |
| 5,512,463 A | 4/1996 | Stemmer .................... 435/91.2 |
| 5,514,588 A | 5/1996 | Varadaraj ..................... 435/262 |
| 5,519,319 A | 5/1996 | Smith et al. |
| 5,521,077 A | 5/1996 | Khosla et al. |
| 5,565,350 A | 10/1996 | Kmiec |
| 5,580,730 A | 12/1996 | Okamoto |
| 5,603,793 A | 2/1997 | Yoshida et al. ............. 156/247 |
| 5,605,793 A | 2/1997 | Stemmer ........................ 435/6 |
| 5,612,205 A | 3/1997 | Kay et al. |
| 5,650,722 A | 7/1997 | Smith et al. |
| 5,675,253 A | 10/1997 | Smith et al. |
| 5,717,085 A | 2/1998 | Little et al. |
| 5,741,691 A | 4/1998 | Arnold et al. |
| 5,760,012 A | 6/1998 | Kmiec et al. |
| 5,763,239 A | 6/1998 | Short et al. .................... 435/6 |
| 5,789,228 A | 8/1998 | Lam et al. .................. 435/209 |
| 5,789,577 A | 8/1998 | Geysen |
| 5,811,238 A | 9/1998 | Stemmer et al. ............... 435/6 |
| 5,814,473 A | 9/1998 | Warren et al. ................ 435/15 |

(Continued)

FOREIGN PATENT DOCUMENTS

EP     0911396 A2     4/1999

(Continued)

OTHER PUBLICATIONS

Josson et al. Nucleic Acids Research, 1993, vol. 21, No. 3, pp. 733-739.*

(Continued)

*Primary Examiner*—John Brusca
*Assistant Examiner*—Shubo (Joe) Zhou
(74) *Attorney, Agent, or Firm*—Beyer Weaver & Thomas, LLP; Sharon M. Fujita; Norman J. Kruse

(57) ABSTRACT

"In silico" nucleic acid recombination methods, related integrated systems utilizing genetic operators and libraries made by in silico shuffling methods are provided.

24 Claims, 22 Drawing Sheets

U.S. PATENT DOCUMENTS

| | | | |
|---|---|---|---|
| 5,824,469 A | 10/1998 | Horwitz et al. | 435/6 |
| 5,828,905 A | 10/1998 | Rao | 435/91.1 |
| 5,830,696 A | 11/1998 | Short | 435/69.1 |
| 5,830,721 A | 11/1998 | Stemmer et al. | 435/489 |
| 5,834,252 A | 11/1998 | Stemmer et al. | 435/91.1 |
| 5,837,458 A | 11/1998 | Minshull et al. | 435/6 |
| 5,866,363 A | 2/1999 | Pieczenik | 435/69.1 |
| 5,869,644 A | 2/1999 | Shortle et al. | |
| 5,876,997 A | 3/1999 | Kretz | 435/196 |
| 5,912,119 A | 6/1999 | Radman et al. | |
| 5,925,749 A | 7/1999 | Mathur et al. | 536/23.1 |
| 5,939,250 A | 8/1999 | Short | 435/4 |
| 5,939,300 A | 8/1999 | Robertson et al. | 435/192 |
| 5,942,430 A | 8/1999 | Robertson et al. | 435/197 |
| 5,948,666 A | 9/1999 | Callen et al. | 435/194 |
| 5,958,672 A | 9/1999 | Short | 435/4 |
| 5,958,751 A | 9/1999 | Murphy et al. | 435/208 |
| 5,962,258 A | 10/1999 | Mathur et al. | 435/69.1 |
| 5,962,283 A | 10/1999 | Warren et al. | 435/128 |
| 5,965,408 A | 10/1999 | Short | 435/252.3 |
| 5,985,646 A | 11/1999 | Murphy et al. | 435/252.3 |
| 6,001,574 A | 12/1999 | Short et al. | 435/6 |
| 6,004,788 A | 12/1999 | Short | 435/183 |
| 6,030,779 A | 2/2000 | Short | 435/6 |
| 6,054,267 A | 4/2000 | Short | 435/6 |
| 6,096,548 A | 8/2000 | Stemmer | |
| 6,107,073 A | 8/2000 | Chen | |
| 6,117,679 A | 9/2000 | Stemmer | |
| 6,125,331 A | 9/2000 | Toh | |
| 6,132,970 A | 10/2000 | Stemmer | |
| 6,153,410 A | 11/2000 | Arnold et al. | |
| 6,159,690 A | 12/2000 | Borrebaeck et al. | |
| 6,188,965 B1 | 2/2001 | Mayo et al. | |
| 6,269,312 B1 | 7/2001 | Mayo et al. | |
| 6,323,030 B1 | 11/2001 | Stemmer | |
| 6,365,408 B1 | 4/2002 | Stemmer | |
| 6,403,312 B1 | 6/2002 | Dahiyat et al. | |
| 6,518,065 B1 | 2/2003 | Stemmer | |
| 6,537,776 B1 | 3/2003 | Short | 435/69.1 |
| 6,605,449 B1 | 8/2003 | Short | 435/69.1 |

FOREIGN PATENT DOCUMENTS

| | | |
|---|---|---|
| EP | 0911396 A3 | 5/1999 |
| EP | 0934999 A1 | 8/1999 |
| WO | WO 91/06643 A1 | 5/1991 |
| WO | WO 92/06176 | 4/1992 |
| WO | WO 95/15972 | 6/1995 |
| WO | WO 95/22625 | 8/1995 |
| WO | WO 96/16073 A2 | 5/1996 |
| WO | WO 96/16073 A3 | 5/1996 |
| WO | WO 96/33207 | 10/1996 |
| WO | WO 97/07205 | 2/1997 |
| WO | WO 97/20078 | 6/1997 |
| WO | WO 97/25410 | 7/1997 |
| WO | WO 97/33957 | 9/1997 |
| WO | WO 97/35957 | 10/1997 |
| WO | WO 97/35966 | 10/1997 |
| WO | WO 97/44361 | 11/1997 |
| WO | WO 97/48416 | 12/1997 |
| WO | WO 97/48717 | 12/1997 |
| WO | WO 97/48794 | 12/1997 |
| WO | WO 98/00526 | 1/1998 |
| WO | WO 98/01581 | 1/1998 |
| WO | WO 98/13485 | 4/1998 |
| WO | WO 98/13487 | 4/1998 |
| WO | WO 98/24799 | 6/1998 |
| WO | WO 98/27230 | 6/1998 |
| WO | WO 98/28416 | 7/1998 |
| WO | WO 98/31837 | 7/1998 |
| WO | WO 98/36080 | 8/1998 |
| WO | WO 98/41622 | 9/1998 |
| WO | WO 98/41623 | 9/1998 |
| WO | WO 98/41653 | 9/1998 |
| WO | WO 98/42832 | 10/1998 |
| WO | WO 98/48034 | 10/1998 |
| WO | WO 98/49350 | 11/1998 |
| WO | WO 98/58085 | 12/1998 |
| WO | WO 99/07837 | 2/1999 |
| WO | WO 99/08539 | 2/1999 |
| WO | WO 99/10472 | 3/1999 |
| WO | WO 99/10539 | 3/1999 |
| WO | WO 99/19518 | 4/1999 |
| WO | WO 99/21979 | 5/1999 |
| WO | WO 99/23107 | 5/1999 |
| WO | WO 99/23236 | 5/1999 |
| WO | WO 99/41368 | 8/1999 |
| WO | WO 99/41369 | 8/1999 |
| WO | WO 99/41383 | 8/1999 |
| WO | WO 99/41402 | 8/1999 |
| WO | WO 99/45154 | 9/1999 |
| WO | WO 99/57128 | 11/1999 |
| WO | WO 99/65927 | 12/1999 |
| WO | WO 00/00632 | 1/2000 |
| WO | WO 00/23564 A2 | 4/2000 |
| WO | WO 00/37684 | 6/2000 |
| WO | WO00/42559 | 7/2000 |
| WO | WO 00/42560 | 7/2000 |
| WO | WO 00/42561 | 7/2000 |
| WO | WO00/47612 | 8/2000 |
| WO | WO 00/53744 | 9/2000 |
| WO | WO 00/58517 | 10/2000 |
| WO | WO01/61344 | 8/2001 |
| WO | WO01/75767 | 10/2001 |
| WO | WO03/055978 | 10/2003 |

OTHER PUBLICATIONS

Dahiyat et al., "Automated design of the surface positions of protein helices" *Protein Science* (1997) 6:1333-1337.

Dahiyat and Mayo "De Novo Protein Design: Fully Automated Sequence Selection" *Science* (1997) vol. 278 pp. 82-87.

Dahiyat et al., "De Novo Protein Design: Towards Fully Automated Sequence Selection" *J. Mol. Biol.* (1997) 273:789-796.

Dahiyat and Mayo "Probing the role of packing specificity in protein design" *Proc. Matl. Acad. Sci. U.S.A.*, 1997 vol. 94 pp. 10172-10177.

Gordon and Mayo "Branch-and-Terminate: a combinatorial optimization algorithm for protein design" *Structure* (1999) 7:1089-1098.

Gordon et al., "Energy functions for protein design" *Current Opinion in Structural Biology* (1999) 9:509-513.

Gordon and Mayo "Radical Performance Enhancements for Combinatorial Optimization Algorithms Based on the Dead-End Elimination Theorem" *Journal of Computational Chemistry*, 1998 vol. 19 No. 13, 1505-1514.

Haney et al., "Structural Basis for Thermostability and Identification of Potential Active Site Residues for Adenylate Kinases From the Archaeal Genus Methanococcus" *Proteins* (1997) 28:117-130.

Harayama, Shigeaki, (1998) "Artificial evolution by DNA shuffling" *Tibtech* vol. 16 pp 76-82.

Malakauskas and Mayo "Design, structure and stability of a hyperthermophilic protein variant" *Nature Structural Biology* (1998) vol. 5, No. 6, 470-475.

Pollock et al., "Coevolving Protein Residues: Maximum Likelihood Identification and Relationship to Structure" *J. Mol. Biol.* (1999) 287:187-198.

Stemmer (1994) DNA shuffling by random fragmentation and reassembly: In vitro recombination for molecular evolution *Proc. Natl. Acad. Sci. USA* vol. 91, pp 10747-10751.
Stemmer et al., "Single-step assembly of a gene and entire plasmid from large numbers of oligodeoxyribonucleotides" *Gene* (1995) 164:49-53.
Street and Mayo "Computational protein design" *Structure* (1999) 7:R105-R109.
Street and Mayo "Intrinsic B-sheet propensities result from van der Waals interactions between side chains and local backbone" *Proc. Natl. Acad. Sci. U.S.A.* (1999) vol. 96 pp. 9074-9076.
Street and Mayo "Pairwise calculation of protein solvent-accessible surface areas" *Folding & Design* (1998) 3:253-258.
Strop and Mayo "Rubredoxin Variant Folds without Iron" *J. American Chem. Soc.* (1999) vol. 121 No. 11 pp. 2341-2345.
Singh et al., (1996) "Application of Genetic Algorithms to Combinatorial Synthesis: A Computational Approach to Lead Identification and Lead Optimization" *J. Chem. Inf. Comput. Sci* vol. 118 pp 1669-1676.
Venkatasubramanian et al., (1995) "Evolutionary Design of Molecules with Desired Properties Using the Genetic Algorithm" *J. Chem. Inf. Comput. Sci.* vol. 35 pp. 188-195.
Wollenberg and Atchley "Separation of phylogenetic and functional associations in biological sequences by using the parametric bootstrap" *PNSA*, 2000 vol. 97, No. 7, pp. 3288-3291.
Zhang, Ching (1994) "A Genetic Algorithm for Molecular Sequence Comparison" *Proceedings of the International Conference on Systems, Man, and Cypernetics* pp 1926-1931.
Crameri & Stemmer "1020-Fold aptamer library amplification without gel purification" *Nucleic Acid Research* (1993) vol. 21 No. 18 p. 4110.
Feng & Doolittle, *J. Mol. Evol.* 35:351-360 (1987).
Higgins & Sharp, *CABIOS*5:151-153 (1989).
Sun (1999) "Modeling DNA Shuffling" *Journal of Computational Biology* 6(1):77-90.
Giver and Arnold "Combinatorial protein design by in vitro recombination" *Current Opinion in Chemical Biology* (1998) 2:335-338.
Sun, Fengzhu, "Modeling DNA Shuffling" *Proceedings of the Second Annual International Conference on Computational Molecular Biology* (1998) 251-257.
Zhao et al., "Molecular evolution by staggered extention process (StEP) in vitro recombination" *Nature Biotechnology* vol. 16 (1998) pp. 258-261.
Altschul et al., *J. Mol. Biol.* 215:403-410 (1990).
Boehnke et al. (1991) "Statistical methods for multipoint radiation hybrid mapping" *Am. J. Hum. Genet.* 49:1174-1188.
Brunner and Bujard (1987) *EMBO J.* 6;3139-3144.
Change et al. (1999) "Evolution of a cytokine using DNA family shuffling" *Nature Biotechnology* 17:793-797.
Christians et al. (1999) "Directed evolution of thymidine kinase for AZT phosphorylation using DNA family shuffling" *Nature Biotechnology* 17:259-264.
Crameri and Stemmer (1995) "Combinatorial multiple cassette mutagenesis creates all the permutations of mutant and wildtype cassettes" *BioTechniques* 18:194-195.
Crameri et al. (1996) "Construction and evolution of antibody-phage libraries by DNA shuffling" *Nature Medicine* 2:100-103.
Crameri et al. (1996) "Improved green fluorescent protein by molecular evolution using DNA shuffling" *Nature Biotechnology* 14:315-319.

Crameri et al. (1997) "Molecular evolution of an arsenate detoxification pathway by DNA shuffling," *Nature Biotechnology* 15:436-438.
Crameri et al. (1998) "DNA shuffling of a family of genes from diverse species accelerates directed evolution" *Nature* 391:288-291.
Gates et al. (1996) "Affinity selective isolation of ligands from peptide libraries through display on a lac repressor 'headpiece dimer'" *Journal of Molecular Biology* 255:373-386.
Irvine et al. (1991) "SELEXION: systematic evolution of ligands by exponential enrichment with integrated optimization by non-linear analysis" *J. Mol. Biol.* 222:739-761.
Jonsson et al. (1993) *Nucleic Acids Res.* 21:733-739.
Kelly et al. (1994) "A test of the Markovian model of DNA evolution" *Biometrics* 50(3):653-64.
Knaus and Bujard (1988) *EMBO J.* 7:2919-2923.
Lander and Waterman (1988) Genomic mapping by fingerprinting random clones: a mathematical analysis *Genomics* 2:231-239.
Lanzer and Bujard (1988) *Proc. Natl. Acad. Sci.* 85:8973-8977.
Minshull and Stemmer (1999) "Protein evolution by molecular breeding" *Current Opinion in Chemical Biology* 3:284-290.
Ness et al. (1999) "DNA Shuffling of subgenomic sequences of subtilisin" *Nature Biotechnology* 17:893-896.
Patten et al. (1997) "Applications of DNA Shuffling to Pharmaceuticals and Vaccines" *Current Opinion in Biotechnology* 8:724-733.
Stemmer (1994) "Rapid evolution of a protein in vitro by DNA shuffling" *Nature* 370:389-391.
Stemmer (1995) "Searching Sequence Space" *Bio/Technology* 13:549-553.
Stemmer (1995) "The Evolution of Molecular Computation" *Science* 270: 1510.
Stemmer (1996) "Sexual PCR and Assembly PCR" In: *The Encyclopedia of Molecular Biology*. VCH Publishers, New York. pp. 447-457.
Stemmer, et al., (1999) "Molecular breeding of viruses for targeting and other clinical properties. Tumor Targeting" 4:1-4.
Sun and Waterman (1996) "A mathematical analysis of in vitro molecular selection-amplification" *J. Mol. Biol.* 258: 650-660.
Zhang et al. (1997) "Directed evolution of an effective fucosidase from a galactosidase by DNA shuffling and screening" *Proceedings of the National Academy of Sciences, U.S.A.* 94:4504-4509.
Alexeev et al. "Stable and Inheritable changes in genotype and phenotype of albino melanocytes induced by an RNA-DNA oligonucleotide." *Nature Biotechnology* 1343-1346 (1998).
Alberts et al. "Recombinant DNA Technology." *New York Publishing, Inc.* 291-312 (1994).
Altschul et al. "Basic Local Alignment Search Tool." *J. Mol. Biol.* 215:403-410 (1990).
Barlett "Long-lasting gene repair ." *Nature Biotechnology* 16:1312 (1998).
Boehnke et al. "Statistical Methods for Multipoint Radation Hybrid Mapping." *Am. J. Hum. Genet.* 49:1174-1188 (1991).
Botstein et al. "Strategies and Applications of in Vitro Mutagenesis." *Science* 229:1193-1201 (1985).

Brunner & Bujard "Promoter recognition and promoter strength in the *Eschichia coli*." *EMBO J.* 6:3139-3144 (1987).

Carter "Site-directed mutagenesis." *Biochem J.* 237:1-7 (1986).

Carter "Improved Oligonucleotide-Directed Mutagenesis Using M13 Vectors." *Methods in Enzymol* 154:382-403 (1987).

Carter "Improved oligonucleotide site-directed mutagenesis using M13 vectors." *Nucleic Acids Res.* 13:4431-4443 (1985).

Chang et al. "Evolution of a cytokine using DNA family shuffling." *Nature Biotechnology* 17:793-797 (1999).

Chee et al. "Accessing Genetic Information with High-Density DNA Arrays." *Science* 274:610-614 (1996).

Christians et al. "Directed evolution of thymidine kinase for AZT phosphorylation using DNA family shuffling." *Nature Biotechnology* 17:259-264 (1999).

Cole-Strauss et al. "Correction of the Mutation Responsible for Sickle Cell Anemia by an RNA-DNA Oligonucleotide." *Science* 1386-1389 (1996).

Crameri et al. DNA shuffling of a family of genes from diverse species accelerates directed evolution. *Nature* 391: 288-291 (1998).

Crameri et al. "Improved Green Fluorescent Protein by Molecular Evolution Using DNA Shuffling" *Nature Biotech* 14:315-319 (1996).

Crameri et al. "Construction and evolution of antibody-phage libraries by DNA shuffling." *Nature Medicine* 2:100-103 (1996).

Crameri et al. "Molecular evolution of an arsenate detoxification pathway by DNA shuffling." *NatureBiotech* 15:436-438 (1997).

Dale et al. "Oligonucleotide-directed Random Mutagenesis Using the Phosporothioate Method." *Methods Mol. Biol.* 57:369-374 (1996).

Fodor et al. "Light-Directed, Spatially Addressable Parallel Chemical Synthesis." *Science* 251-767-777 (1991).

Fodor "Genome Analysis: Genome Technology." *FASEB Journal* 11:121 (1997).

Fodor "Massively Parallel Genomics." *Science* 227:393-395 (1997).

Gates et al. "Affinity Selective Isolation of Ligands from Peptide Libraries Through Display on a lac Repressor 'Headpiece'" *J. Mol.Bio.* 255:373-386 (1996).

Hill et al. "The structure of granulocyte-colony-stimulating factor and its relationship to other growth factors." *PNAS* 90:5167 (1993).

Irvine et al. "Systematic Evolution of Ligands by Exponential Enrichment with Integrated Optimization by Non-linear Analysis." *J. Mol. Biol.* 222:739-761 (1991).

Kaczorowski et al. "Co-operatively of hexamer ligation." *Gene* 179(1):189-193 (1996).

Karlin et al. "Applications and statistics for multiple high-scoring segments in molecular sequences." *PNAS USA* 90:5873-5787 (1993).

Kayushin et al. "A convenient approach to the synthesis of trinucleotide phosphoroamidites-synthons for the generation of oligonucleotide/peptide libraries." *Nucleic Acids Res.* 24:3748-3755 (1996).

Kelly et al. "A Test of the Markovian Model of DNA Evolution." *Biometrice* 50(3):653-664 (1994).

Knaus and Bujard "$P_L$ of coliphage lambda: an alternative solution for an efficient promoter." *EMBO J.*7:2912-2923 (1998).

Kren et al. "Targeted Nucleotide Exchange in the Alkaline Phosphatase Gene of HuH-7 Celles Mediated by a Chimeric RNA/DNA Oligonucleotide." *Hepatology* 25(6):1462-1468 (1997).

Kren et al. "In Vivo site-directed mutagenesis of the factor IX gene by chimeric RNA/DNA oligonucleotides." *Nature Medicine*4(3):285-290 (1998).

Kunkel "The Efficiency of Oligonucleotide-Directed Mutagenesis." *Nucleic Acids & Mol. Biol* (1997).

Lander and Waterman "Genomic Mapping by Fingerprinting Random Clones: A Mathematical Analysis." *Genomics* 2:231-239 (1998).

Lanzer and Bujard "Promoters largely determine the efficiency for repressor action." *Proc. Natl. Acad. Sci. USA*85: 8973-8977 (1998).

Ling et al. "Approaches to DNA Mutagenesis: An Overview." *Anal Biochem.* 254(2):157-178 (1997).

Mehling et al. "Nucleotide sequences of streptomycete 16S ribosomal DNA: towards a specific identification system for streptomycetes using PCR." *Microbiology* 141:2139-2147 (1995).

Minshull "Protein evolution by molecular breeding." *Curr. Opin. In Chem. Bio.*3:284-290 (1999).

Mintz et al. "EHD1-An EH-Domain-Containing Protein with a Specific Expression Pattern." *Genomics* 59(1):66-76 (1999).

Muerhoff et al. Identification of conserved nucleotide sequences within the GB virus c 5-untranslated region: Design of PCR primers for detection of viral RNA *J. Virological Methods* 62:55-62 (1996).

Nakamaye et al. "Inhibition of restriction endonuclease Nci l Cleavage by phosphorothioate groups and its applications to olgonucleotide-directed mutagenesis." *Nucleic Acids. Res.* 14:9679-9698 (1986).

Needleman et al. "A General Method Applicable to the Search for Similarities in the Amino Acid Sequence of Two Proteins." *J. Mol. Biol.* 48:443 (1970).

Ness "DNA shuffling of subgenomic sequences of subtilisin." *Nature Biotech.* 17:893-896 (1999).

Pathy "Modular exchange principles in proteins." *Curr Opinion in Structural Biology* 1:351-361 (1991).

Pathy "Introns and exons." *Curr. Opinion in Structural Biology* 4:383-392 (1994).

Patten et al. "Applications of DNA shuffling to pharmaceuticals and vaccines." *Curr Opin in Biotech* 8:724-733 (1997).

Pearson et al. "Improved tools for biological sequence comparison." *PNAS* 85:2444 (1998).

Porter et al. "Direct PCR Sequencing with boronated Nucleotides." *Nucleic Acids Res.* 25(8):1611-1617 (1997).

Sayers et al. "5'-3'Exonucleases in phosphorothioate-baised oligonucleotide-directed mutagenesis." *Nucleic Acids Res.* 16:791-802(1988).

Sayers et al. "Strand specific cleavage of phosphorothioate-containing DNA by reaction with restriction endonucleases in the presence of ethidium bromide." *Nucleic Acids Res.* 16:803-814 (1988).

Smith "In Vitro Mutagenesis." *Ann. Rev. Genet.* 19:423-462 (1985).

Smith et al. "Comparison of Biosequences."*Adv. Appl. Math* 2:482 (1981).

Stemmer et al. "Rapid evolution of a protein in vitro by DNA shuffling." *Nature* 370:389-391 (1994).

Stemmer "Searching Sequence Space." *Bio/Tech* 13:549-533 (1995).

Stemmer "Sexual PCR and Assembly PCR." *Ency.Mol. Bio.* 447-457 (1996).
Stemmer et al. "Molecular breeding of viruses for targeting and other clinical properties." *Tumor Targeting* 4:59-62 (1999).
Stemmer "The Evolution of Molecular Computation." *Science* 270:1510 (1995).
Strauss "The Site-Specific Correction of Genetic Defects." *Nature Medicine* 4:274-275 (1998).
Sun et al. "A Mathematical Analysis of in vitro Molecular Selection-Amplification." *J. Mol. Biol.* 258:650-660 (1996).
Taylor et al. "The use of phosphorothioate-modified DNA in restriction enzyme reactions to prepare nicked DNA." *Nucleic Acids Res.* 13:8749-8764 (1985).
Taylor et al. "The rapid generation of oligonucleotide-directed mutations at high frequency using phosphorothioate-modified DNA." *Nucleic Acids Res.* 13:8765-8787 (1985).
Virnekas et al. "Trinucleotide phisphoramidites: ideal reagents for the synthesis of mixed olignucleotides for random mutagenesis." *Nucleic Acids Res.* 22:5600-5607 (1994).
Von Der Osten et al. "Protein engineering of subtilisins to improve stability in detergent formulations." *J. Biotechnol.* 28:55-68 (1993).
Wells "Importance of hydrogen-bond formation in stabilizing the transition state of subtilisin." *Trans. R. Soc. Lond.* A317:415-423 (1986).
Whipple et al. "Application of Genetic Algorithms to Combinatorial Sknthesis: A Computational Approach to Lead Idantification and Lead Optimization." *J. AM. Chem Soc.* 118:1669-1676 (1996).
Xiang et al. "Targeted gene conversion in a mammalian CD34+-enriched cell population using a chimeric RNA/DNA olgonucleotide." *J. Mol. Med.* 75:829-835 (1997).
Yood et al. "Targeted gene correction of episomal DNA in mammalian cells mediated by a chimeric RNA-DNA oligonucleotide." *PNAS* 93:2071-2076 (1996).
Yokomori et al. "A Similarity measure for DNA sequence analysis based on locality." *Genome Inf. Ser.* 4:283-292 (1993).
Young et al. "Characterization of the Receptor binding determinants of granulocyte colony stimulating factor." *Protein Science* 6:1228-1236 (1997).
Zang et al. "Directed evolution of a fucosidase from a galactosidase by DNA shuffling and screening." *PNAS USA* 94:4504-4509 (1997).
Zoller "New recombinant DNA methodology for protein engineering." *Curr. Opinion in Biotechnology* 3:348-354 (1992).
Arkin "Optimizing Nucleotide Mixtures to Encode Specific Subsets of Smino Acids for Semi-Random Mutagenesis." Biotechnology (N Y). Mar. 1992;10(3):297-300.
Arkin "An algorithm for protein engineering: Simulations of recursive ensemble mutagenesis." Proc Natl Acad Sci U S A. Aug. 15, 1992;89(16):7811-5.
Delagrave "Searching Sequence Space to Engineer Proteins: Exponential Ensemble Mutagenesis." Biotechnology (N Y). Dec. 1993;11(13):1548-52.
Delagrave "Recursive ensemble mutagenesis." Protein Eng. Apr. 1993;6(3):327-31.
Delagrave "Context dependence of phenotype prediction and diversity in combinatorial mutagenesis." Protein Eng. Mar. 1995;8(3):237-42.

Goldman "An Algprithmically Optimized Combinatorial Library Screened by Digital Imaging Spectroscopy."7 Biotechnology (N Y). Dec. 1992;10(12):1557-61.
Robles "Hydropathy and Molar Volume Constraints on Combinatorial Mutants of the Photosynthetic Reaction Center." J Mol Biol. Jul. 5, 1993;232(1):242-52.
Youvan Imaging Sequence Space. Nature. May 5, 1994;369 (6475):79-80.
Chamberlain et al. (1990) "Multiplex PCR for the Diagonosis of Duchenne Muscular Dystrophy." *PCR Protocols* 272-281.
Hayashi et al. (1994) "Simultaneous Mutagenesis of Anitbody CDR Regions by Overlap Extension and PCR." *Bio Techniques* 17(2):310-315.
Jirholt et al. (1998) "Exploiting sequence space: shuffling in vivo formed complementarity determining regions into a master framework." *Gene* 215:471-476.
Kobayashi et al (1997) "Analysis of Assembly of Synthetic Antibody Fragments: Expression of Functional scFv with Predefined Specificity." *BioTechniques* 23(3):500-503.
Prodromou et al (1992) "Recursive PCR: a novel technique for total gene synthesis." *Protein Engineering* 5(8):827-829.
Soderlind et al.(1999) "Complementarity-dtermining region (CDR) implantatio: a theme or recombination." *Immunothnology* 4:279-285.
Soderlind et al.( (2000) "Recombining germline0derived CDR sequences for creating diverse single-framework antibody libraries." *Nature Biothecnology* 18:852-856.
Soderlind et al. (1995) "Domain libraries: Synthetic diversity for de novo design of antibody V-regions." *Gene* 160:269-272.
Dewey et al. (1998) "Non-equilibrum Thermodynamics of Molecular Evolution." *J. Theor Biol*.193:593-599.
Morchio et al. (1997) "Simulation of Protein Evolution: Evidence for a Non-linear Aminoacidic Substitution Rate." *Riv Biol* 83-94.
Dahiyat and Mayo, "Protein Design Automation," Protein Science, 5:895-903, (1996).
Su et al., "Coupling Backbone Flexibility and Amino Acid Sequence Selection in Protein Design," Protein Science, 6:1701-1707, (1997).
Voigt et al., "Computationally Focusing the Directed Evolution of Proteins," Journal of Cellular Biochemistry Supplement, 37:58-63 (2001).
Hellberg et al., "Minimum Analogue Peptide Sets (MAPS) for quantitative Structure-Activity Relationships," Int. J. Peptide Protein Res. 37:414-427 (1991).
Martin van Heel, "A New Family of Powerful Multivariates Statistical Sequence Analysis Techniques," J. Mol. Biol, 220:877-887 (1991).
Goldman et al., "Estimating Protein Function From Combinatorial Sequence Data Using Decision Algorithms and Neural Networks," Drug Dev. Research 33:125-132 (1994).
Gustafsson et al., "Exploration of Sequence Space for Protein Engineering," J. Mol. Recognit. 14:308-314 (2001).
Miyazawa et al., "Residue-Residue Potentials with a Favorable Contact Pair Term and an Unfavorable High Packing Density Term, for Simulation and Threading," J. Mol. Biol., 256:623-644 (1996).
Chao Zhang, "Extracting Contact Energies From Protein Structures: A Study Using a Simplified Model," Proteins: Structure, Function, and Genetics, 31:299-308 (1998).
Miyazawa et al., "Self-Consistent Estimation of Inter-Residue Protein Contact Engergies Based on an Equilibrium Mixture Approximation of Residues," Proteins: Structure, Function, and Genetics, 34:49-68 (1999).

Miyazawa et al., "An Empirical Engergy Potential With a References State for Protein Fold and Sequence Recognition," Proteins: Structure, Function, and Genetics, 36:357-369 (1999).

Moore et al., "Predicting Crossover Generation in DNS Shuffling," PNAS, vol. 98, No. 6, 3226-3231 (2001).

Lehman et al., "Engineering Proteins for Thermostability: the Use of Sequence Alignments Versus Rational Design and Directed Evolution," Current Opinion in Biotechnology, 13:371-375 (2001).

Colleen Kelly, "A Test of the Markovian Model of DNA Evolution," Biometrics 50, 653-664, (1994).

H.W. Hellinga, "Rational Protein Design: Combining Theory and Experiment," Proc. Natl. Acad. Sci. USA, vol. 94, pp. 10015-10017, (1997).

William F. DeGrado, "Proteins from Scratch," Science, vol. 278, 80-81 (1997).

Jonsson, et al, "Quaintitative Sequence-Activity Modeils (QSAM)- Tool For Sequence Design", Nuclear Acid Research vol. 21, No. 3, pp. 733-739 (1993).

Sjostrom, et al, "Signal Peptide Amino Acid Sequences In *Escheruchua coli* Contain Information Related To Final Protein Localization. A Multivariate Data Analysis", The CMBO Journal vol. 6, No. 3, pp 823-831, (1987).

Patel, et al, "Patenting Computer-Designed Peptides", Journal Of Computer-Acid Molecular Design 12 pp543-556, (1998).

Schneider, et al, "Peptide Design by Artificial Neural Networks and Computer-Based Evolutionary Search", Proc. Natl. Acad. Sci. USA, vol. 95, pp. 12179-121184, Oct. 1998.

Mee, et al, "Design of Active Analogues of a 15-Residue Peptide Using D-Optimal Design QSAR and a Combinatorial Search Algorithm", J Peptide Res. 49, pp. 89-102, (1997).

Bogarad, et al, "A Hierarchical Approach to Protein Molecular Evolution", Proc. Natl. Acad. Sci. USA, vol. 96, pp. 2597-2595, Mar. 1999.

Darius, et al, "Simulated Molecular Evolution Or Computer-Generated Artifacts?", Biophysical Journal, vol. 67, pp. 2120-2122, Nov. 1994.

Diatchenko et al. (1996) "Suppression subtractive hybridiztion: A method for generating different regulated or tissue-specific cDNA probes and libraries." PNAS USA 93:6025-6030.

Shao et al. (1998) "Random-priming in vitro recobination: an effective tool for directed evolution." Nucleic Acids Research 26(2):681-683.

Gregory L. Moore, Costas D. Maranas, *Modeling DNA Mutation and Recombination for Directed Evolution Experiments*, Department of Chemical Engineering, The Pennsylvania State University, University Park, Received Oct. 28, 1999, Accepted in revised from Apr. 15, 2000 © 2000 Academic Press.

Jan Drenth, Principles of Protein X-Ray Crystallography, Springer-Verlag, pp. 12-18, 1995.

Robert F. Service, "Tapping DNA for Structures Produces a Trickle," News Focus, Science, vol. 298, pp. 948-950, 2002.

Accelrys Website, GCG Winconsin Package, 15 Pages, 2002.

Lewis Ricki, The Scientist, pp. 1-4, 1993.

Chen et al., "Tuning the Activity of an Enzyme for Unusual Environments: Sequential Random Mutagenesis of Substilisin E for Catalysis in Dimethylformamide," Proc. Natl. Acad. Sci. USA, vol. 90, pp. 5618-5622, 1993.

Abkevich et al., "Impact of Local and Non-Local Interactions on Thermodynamics and Kinetics of Protein Folding," J. Mol. Biol., 252: 460-471, 1995.

Richards et al., "Advances in Protein Chemistry," Adv. Protein Chem., 55:ix-xi, 2000.

M. Ostwemeier et al., "A Combinatorial Approach to Hybrid Enzymes Independent of DNA Homology," Nature Biotechnology, vol. 17, pp. 1205-1209, 1999.

Arnold, "Combinatorial and Computational Challenges for Biocatalyst design", *Nature, 2001, 409(6817):253-257*.

Boder et al., "Directed Evolution of Antibody Fragments with Monovalent Femtomolar Antigen binding Affinity", *Proc. Natl. Acad. Sci. USA, 97 (20):10701-10705*, 2000.

Bohm, "New approaches in molecular structure prediction", *Biophys Chem., 1996, 59: 1-32*.

Chen & Arnold, F.H., "Tuning the Activity of an Enzyme for Unusual Environments: Sequential Random Mutagenesis of Subtilisin E for Catalysis in Dimethyyformamide", *Proc. Natl. Acad. Sci. U.S.A. 1993, 90:5618-5622*.

De Maeyer et al., "All in One: A Highly Detailed Roamer Library Improves Both Accuracy and Speed in the Modeling of Sidechains by Dead-End Elimination", *Folding & Design, 1997, 2, 53-66*.

Desjarlais & Clarke N.D., "Computer Search Algorithms in Protein Modification and Design," *Curr. Opin. Struct. Biol., 1998, 8:471-475*.

Dube et al., "Selection of New Biologically Active Molecules from Random Nucleotide Sequences," Gene 1993, 137:41-47.

Dunbrack & Karplus, M., "Backbone-Dependent Rotamer Library for Proteins Application to Sidechain Prediction," *J. Mol. Biol.* 1993, 230:543-574.

Dunbrack & Karplus, "Conformational Analysis of the Backbone-Dependent Roamer Preferences of Protein Sidechains," *Nature Struct. Bio/.* 1994, 1:334-340.

Fetrow et al ., "New program for Protein Tertiary Structure Prediction," *Biotechnol., 1993*, 11(4):479-484.

Flickinger et al., "Enzymes, Directed Evolution", in *2 Encyclopedia of Bioprocess Technology: Fermentation, Biocatalysis, and Bioseparation* 1999, 2:971-987.

Giver et al, "Directed evolution of a Thermostable Esterase," *Proc. Nat!. Acad. Sci., USA 1998*, 95:12809-12813.

Godzik, "In Search of the Ideal Protein Sequence," *Protein Engineering*, 1995, 8:409-416.

Hogue et al., "Structure Databases," *Methods Biochem. Anal.* 1998, 39:46-73.

Johnson et al., "The Traveling Salesmand Problem: A Case Study in Local Optimization," In Local Search in Combinatorial Optimization, Edited by Aarts et al., John Wiley & Sons Ltd., 21-310, 1997.

Geladi et al., "Partial Least Squares Regression: A Tutorial," Anal Chim Acta, 168: 1-17, 1986.

Holowachuk et al., "Efficient Gene Synthesis by Klenow Assembly/Extension-Pfu Polymerase Amplification (KAPPA) of Overlapping Olingonucleotides," PCR Methods Appl, 4:299-302, 1995.

Aita et al., "Theory of Evolutionary Molecular Engineering Through Simultaneous Accumulation of Advantageous Mutations," J. Theor. Biol., 207:543-556, 2000.

Jain et al., "The Crystal Structure of an Autoprocessed Ser221 Cys-subtilisin E-propeptide Complexat 2.0 A Resolution," *Mol. Biol.* 1998, 284:137-144.

Joo et al., "Laboratory Evolution of Peroxide-Mediated Cytochrome P450 Hydroxylation.," Nature 1999, 399:670-672.

Kay, "NMR Methods for the Study of Protein Structure and Dynamics," Biochem. Cell Biol., 1997, 75:1-1 5 (1997).

Koehl & Delarue, "Application of a Self-consistent Mean Field Theory to Predict Protein Side-chains Conformation and Estimate Their Conformational Entropy", J. Mol. Bioi. 1994, 239:249-275.

Koehl & Delarue, Mean-field Minimization Methods for Biological Macromolecules Curr. Opin. In Struct. Biol. 1996, 6:222-226.

Lazar, "De Novo Design of the Hydrophobic Core of Ubiquitin," Protein Science, 1997, 6:1167-1178.

Lee & Richards, "The Interpretation of Protein Structures: Estimation of Static Accessibility," J. Mol. Biol.,1971, 55: 379-400.

Lee & Subbiah "Prediction of Protein Side-chain Conformation by Packing Optimization," J. Mol. Biol., 1991, 217,373-388.

Lee, "Predicting Protein Mutant Energetics by Self-consistent Ensemble Optimization," J. Mol. Biol., 1994, 236:918-939.

Levitt et al., "Protein folding: The endgame," *Annu. Rev. Biochem.*, 1997, 66:549-579.

Li et al., "Emergence of Preferred Structures in a Simple Model of Protein Folding," *Science* 1996, 273:666-669.

Matsumura et al., "Structural Studies of Mutants of T4 Lysozyme That Alter Hydrophobic Stabilization," *J. Biol. Chem.* 1989, 264:16059-16066.

Miyazaki & Arnold, "Exploring Nonnatural Evolutionary Pathways by Saturation Mutagenesis: Rapid Improvement of Protein Function," *J. Molecular Evolution*, 1999, 49:716-720.

Miyazaki & Arnold, "Directed Evolution Study of Temperature Adaptation in a Psychrophilic Enzyme," *J.Mol. Biol.* 2000, 297:1015-1026.

Moore & Arnold, "Directed Evolution of a Para-nitrobenzyl esterase for aqueous-organic Solvents," *Nature Biotechnology*, 1996, 14(4):458.

Nikolova et al., "Semirational Design of Active Tumor Suppressor P53 DNA Binding Domain with Enhanced Stability," *Proc. Natl. Acad. Sci. U.S.A.* 1998, 95:14675-14680.

Pjura et al, "Development of an in vivo Method to Identify Mutants of Phage T4 lysozyme of Enhanced Thermostability," *Protein Science* 1993, 2:2217-2225.

Fontana & Shuster, "Continuity in Evolution: On the Nature of Transitions," *Science* 1998, 280:1451-1455.

Sasai, "Conformation, Energy, and Folding Ability of Selected Amino Acid Sequences," *Proc. Natl. Acad. Sci. USA*, 1995, 92: 8438-8442.

Saven & Wolynes, "Statistical Mechanics of the Combinatorial Synthesis and Analysis of Folding Macromolecules," *J. Phys. Chem. B.* 1997, 101:8375-8389.

Skandalis et al., "Creating Novel Enzymes by Applied Molecular Evolution," *Chem. Biol.* 1997, 4:889-898.

Whitlow, "1.85 A structure of Anti-Fluorescein 4-4-20 Fab," *Protein Engineering*, 1995, 8:749-761.

Wilson et al., "Modeling Side-chain Conformation for Homologous Proteins Using an Energy-Based Rotomer Search," *J. Mol. Biol.* 1993, 229:996-1006.

Wuthrich, "NMR—This Other Method for Protein and Nucleic Acid Structure Determination," *Acta Cyrstallogr.*, 1995, D51:249-270.

You & Arnold, "Directed Evolution of Subtilisin E in *Bacillus Subtilis* to Enhance Total Activity in Aqueous Dimethylformamide", *Protein Engineering* 1994, 9(1):77-83.

Zhao & Arnold, "Optimization of DNA shuffling for High Fidelity Recombination," *Nuci. Acids Res., 1997, 25(6): 1307-1308*.

Zhao & Arnold, "Directed Evolution Converts Subtilisin E into a Functional Equivalent of Thermitase," *Protein Engineering 1999, 12(1):47-53*.

Martin et al., "Measuring Diversity: Experimental Design of Combinatorial Libraries for Drug Discovery," J. Med. Chem. 38, 1431-1436, 1995.

Sheridan et al., "Using a Genetic Algorithm to Suggest Combinatorial Libraries," J. Chem. Inf. Compu. Sci., 35, 310-320, 1995.

D.K. Agrafiotis, "Multiobjective Optimization of Combinatorial Libraries," IBM J. Res & Dev., vol., 45, No. 3, 545-566, 2001.

Peter Halling, "Is Random Mutation More Rational", Nature Biotechnology, vol. 14, Apr. 1996.

Jonathan King, "Unexpected Pathways to Protein Stabilization", Nature Biotechnology, vol. 14, Apr. 1996.

Roger Sheldon, "Picking a Winner", Nature, vol. 399, Jun. 17, 1999, pp.636-637.

Holler et al., "In Vitro evolution of a T Cell Receptor with High Affinity for Peptide /MHC", Proc. National Academy Sci USA, vol., 97, No. 10, May 9, 2000, pp. 5387-5392.

Foote et al., Breaking the Affinity Ceiling for Antibodies and T. Cell Receptors, Proc. National Academy Sci USA, vol. 97, No. 20, Sep. 26, 2000, pp. 10679-10681.

Corpet et al., "Browsing Protein Families Via the Rich Family Description Format," Bioinformatics, vol. 15, No. 12, 1999, pp. 1020-1027.

Mironov et al., "Computer Analysis of Transcription Regulatory Patterns in Completely Sequenced Bacterial Genomes," Nucleic Acids Research, vol. 27, No. 14, 1999, pp. 2981-2989.

Kel et al., A genetic algorithm for designing gene family-specific oligonucleotide sets used for hybridization: the G protein-coupled receptor protein superfamily, BIOINFORMATICS, 1998, vol. 14, No. 3, pp. 259-270.

European Search Report dated Feb. 14, 2003 from related European Application No. 00 909 922.7-2201.

* cited by examiner

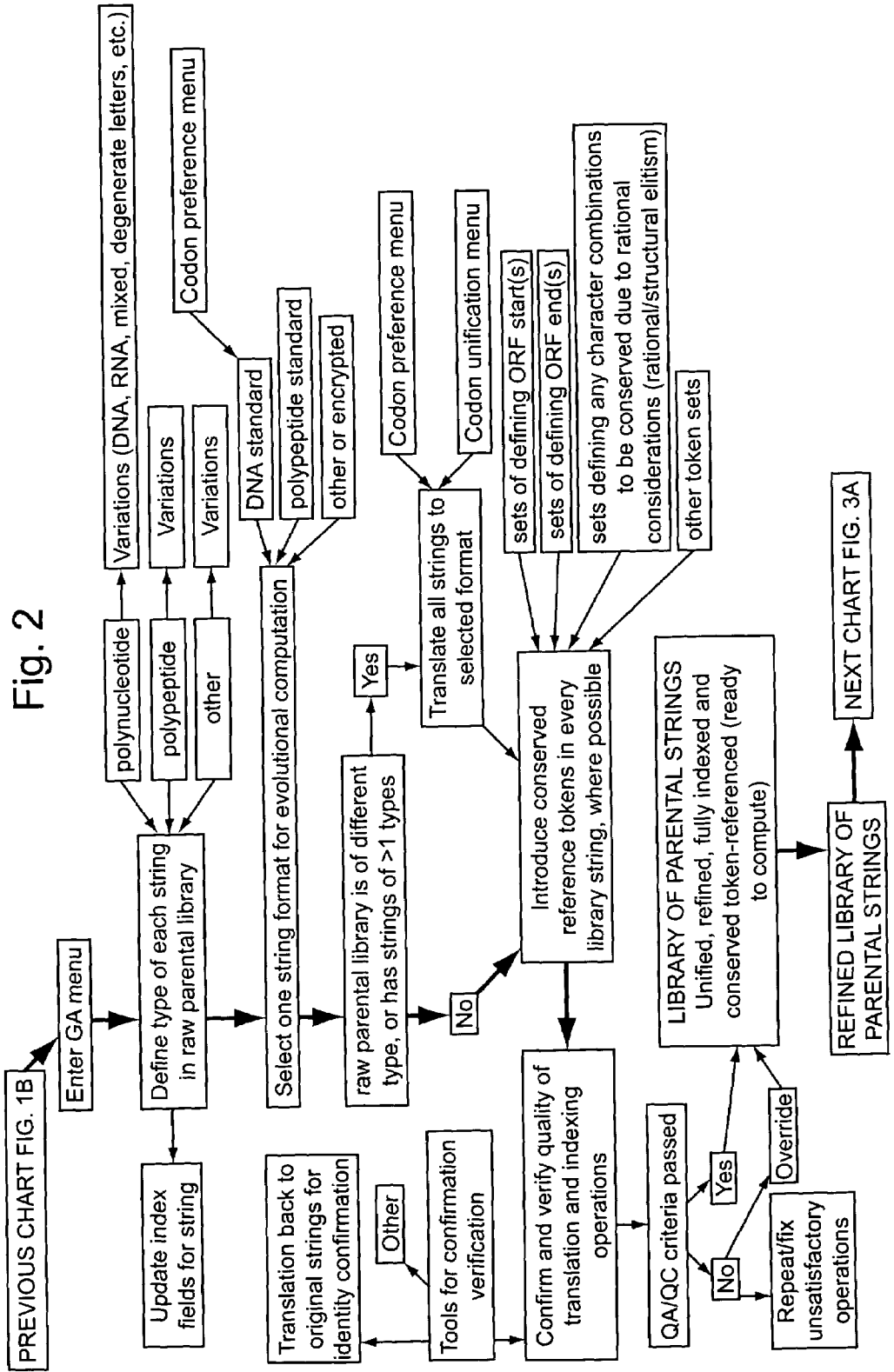

Percent Similarity

|   | 1 | 2 | 3 | 4 | 5 | 6 | 7 |   |                        |
|---|---|---|---|---|---|---|---|---|------------------------|
| 1 |   | 62.1 | 81.4 | 57.6 | 81.8 | 56.1 | 59.1 | 1 | A27211 synthetic 309.PM |
| 2 | 50.5 |   | 61.0 | 54.9 | 59.5 | 58.2 | 60.8 | 2 | BACAPRQ subtilisin.PM |
| 3 | 21.0 | 52.0 |   | 54.6 | 78.4 | 50.6 | 53.2 | 3 | BACAPRS subtilisin.PM |
| 4 | 54.4 | 63.3 | 62.3 |   | 52.0 | 64.6 | 67.9 | 4 | BACSBTL subtilisin.PM |
| 5 | 20.5 | 54.9 | 25.1 | 65.6 |   | 53.9 | 56.5 | 5 | BACYAB subtilisin alk.PM |
| 6 | 58.6 | 56.6 | 72.2 | 44.2 | 63.4 |   | 94.9 | 6 | BLSC11594 subtilisin.PM |
| 7 | 52.5 | 51.4 | 66.0 | 38.5 | 57.8 | 4.9 |   | 7 | I82494 keratinase.PM |
|   | 1 | 2 | 3 | 4 | 5 | 6 | 7 |   |                        |

Introducing indexed crossover points marker into sequence of each of the parents
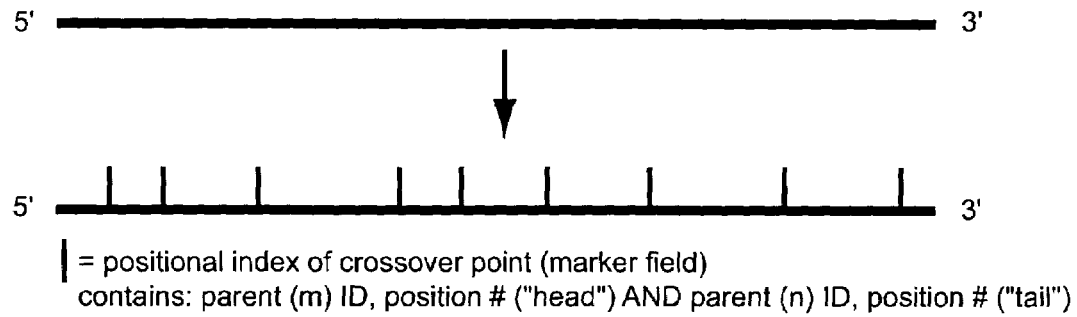
| = positional index of crossover point (marker field)
contains: parent (m) ID, position # ("head") AND parent (n) ID, position # ("tail")
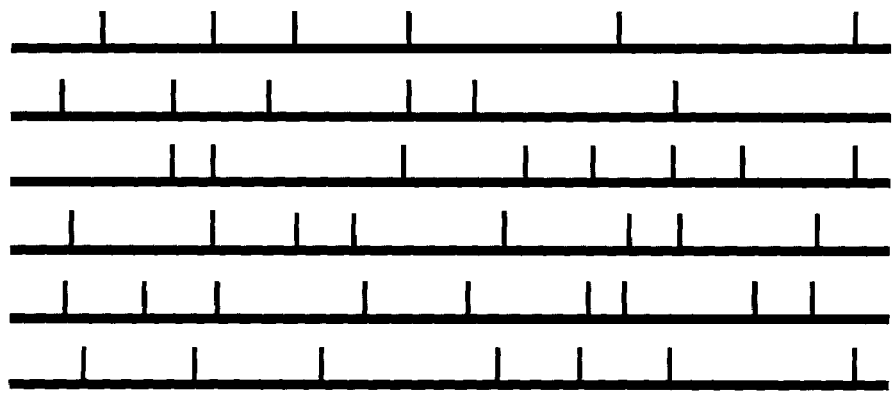
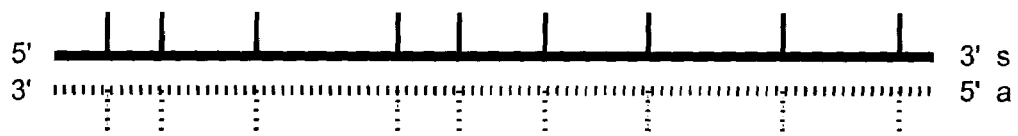
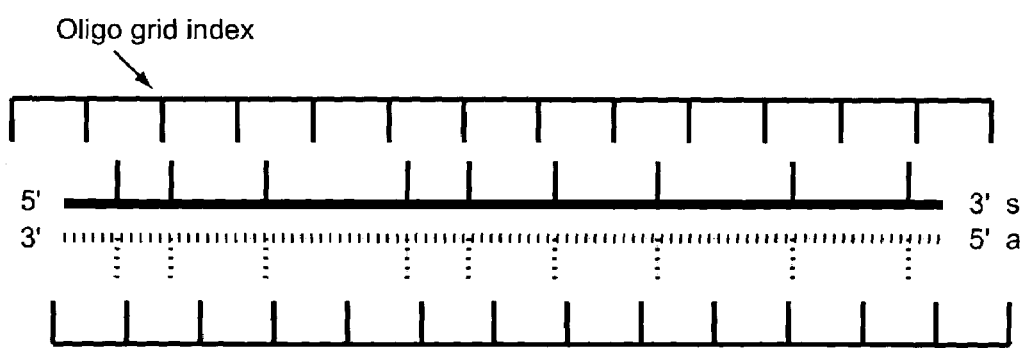
Fig. 9

Percent Similarity

| | 1 | 2 | 3 | |
|---|---|---|---|---|
| 1 | | 87.1 | 79.1 | 1 |
| 2 | 13.0 | | 83.3 | 2 |
| 3 | 21.7 | 17.9 | | 3 |
| | 1 | 2 | 3 | |

1  24DNT-45DO.ISP-L.prot
2  2NT-23DO.ISP-L.prot
3  NDO-PpG7.ISP-L.prot

Geometric representation
Equal distance between
each nucleotide

| A | −1 −1 +1 |
| C | +1 −1 −1 |
| G | −1 +1 −1 |
| T | +1 +1 +1 |

Numeric representation

METHODS FOR MAKING CHARACTER STRINGS, POLYNUCLEOTIDES AND POLYPEPTIDES HAVING DESIRED CHARACTERISTICS

CROSS-REFERENCE TO RELATED APPLICATIONS

This application is a continuation-in-part of "METHODS FOR MAKING CHARACTER STRINGS, POLYNUCLEOTIDES AND POLYPEPTIDES HAVING DESIRED CHARACTERISTICS" by Selifonov et al., U.S. Ser. No. 09/539,486 Filed Mar. 30, 2000, which is a continuation-in-part of "METHODS FOR MAKING CHARACTER STRINGS, POLYNUCLEOTIDES AND POLYPEPTIDES HAVING DESIRED CHARACTERISTICS" by Selifonov et al., filed Jan. 18, 2000, U.S. Ser. No. 09/494,282, and "METHODS FOR MAKING CHARACTER STRINGS, POLYNUCLEOTIDES AND POLYPEPTIDES HAVING DESIRED CHARACTERISTICS" by Selifonov et al., filed Jan. 18, 2000, USSN PCT/US00/01202; which are continuation-in-part applications of "METHODS FOR MAKING CHARACTER STRINGS, POLYNUCLEOTIDES AND POLYPEPTIDES HAVING DESIRED CHARACTERISTICS" by Selifonov et al., U.S. Ser. No. 09/416,375, filed Oct. 12, 1999, now ABN which is a non provisional of "METHODS FOR MAKING CHARACTER STRINGS, POLYNUCLEOTIDES AND POLYPEPTIDES HAVING DESIRED CHARACTERISTICS" by Selifonov and Stemmer, U.S. Ser. No. 60/116,447, filed Jan. 19, 1999 and a non-provisional of "METHODS FOR MAKING CHARACTER STRINGS, POLYNUCLEOTIDES AND POLYPEPTIDES HAVING DESIRED CHARACTERISTICS" by Selifonov and Stemmer, U.S. Ser. No. 60/118,854, filed Feb. 5, 1999.

This application is also a continuation-in-part of "OLIGONUCLEOTIDE MEDIATED NUCLEIC ACID RECOMBINATION" by Crameri et al., Filed Jan. 18, 2000, U.S. Ser. No. 09/484,850 now U.S. Pat. No. 6,368,861 and of "OLIGONUCLEOTIDE MEDIATED NUCLEIC ACID RECOMBINATION" by Crameri et al., Filed Jan. 18, 2000, USSN PCT/US00/01203, which are continuation-in-part applications of "OLIGONUCLEOTIDE MEDIATED NUCLEIC ACID RECOMBINATION" by Crameri et al., U.S. Ser. No. 09/408,392, filed Sep. 28, 1999, now U.S. Pat. No. 6,376,246 which is a non-provisional of "OLIGONUCLEOTIDE MEDIATED NUCLEIC ACID RECOMBINATION" by Crameri et al., U.S. Ser. No. 60/118,813, filed Feb. 5, 1999 and a non-provisional of "OLIGONUCLEOTIDE MEDIATED NUCLEIC ACID RECOMBINATION" by Crameri et al., U.S. Ser. No. 60/141,049, filed Jun. 24, 1999.

This application is also a continuation-in-part of "METHODS OF POPULATING DATA STRUCTURES FOR USE IN EVOLUTIONARY SIMULATIONS" by Selifonov and Stemmer, USSN PCT/US00/01138, filed Jan. 18, 2000 which is a continuation-in-part of "METHODS OF POPULATING DATA STRUCTURES FOR USE IN EVOLUTIONARY SIMULATIONS" by Selifonov and Stemmer, U.S. Ser. No. 09/416,837, filed Oct. 12, 1999.

This application is also related to "USE OF CODON VARIED OLIGONUCLEOTIDE SYNTHESIS FOR SYNTHETIC SHUFFLING" by Welch et al., U.S. Ser. No. 09/408,393, filed Sep. 28, 1999.

The present application claims priority to and benefit of each of the applications listed in this section, as provided for under 35 U.S.C. §119(e) and/or 35 U.S.C. §120, as well as any other applicable statue or rule, as appropriate. All of the preceding applications are incorporated herein by reference.

COPYRIGHT NOTIFICATION

Pursuant to 37 C.F.R. 1.71(e), Applicants note that a portion of this disclosure contains material which is subject to copyright protection. The copyright owner has no objection to the facsimile reproduction by anyone of the patent document or patent disclosure, as it appears in the Patent and Trademark Office patent file or records, but otherwise reserves all copyright rights whatsoever.

FIELD OF THE INVENTION

This invention is in the field of genetic algorithms and the application of genetic algorithms to nucleic acid shuffling methods.

BACKGROUND OF THE INVENTION

Recursive nucleic acid recombination ("shuffling") provides for the rapid evolution of nucleic acids, in vitro and in vivo. This rapid evolution provides for the generation of encoded molecules (e.g., nucleic acids and proteins) with new and/or improved properties. Proteins and nucleic acids of industrial, agricultural and therapeutic importance can be created or improved through DNA shuffling procedures.

A number of publications by the inventors and their co-workers describe DNA shuffling. For example, Stemmer et al. (1994) "Rapid Evolution of a Protein" *Nature* 370: 389–391; Stemmer (1994) "DNA Shuffling by Random Fragmentation and Reassembly: in vitro Recombination for Molecular Evolution," *Proc. Natl. Acad. USA* 91:10747–10751; Stemmer, U.S. Pat. No. 5,603,793 "METHODS FOR IN VITRO RECOMBINATION;" Stemmer et al., U.S. Pat. No. 5,830,721, "DNA MUTAGENESIS BY RANDOM FRAGMENTATION AND REASSEMBLY;" and Stemmer et al., U.S. Pat. No. 5,811,238 "METHODS FOR GENERATING POLYNUCLEOTIDES HAVING DESIRED CHARACTERISTICS BY ITERATIVE SELECTION AND RECOMBINATION" describe, e.g., a variety of shuffling techniques.

Many applications of DNA shuffling technology have also been developed by the inventors and their co-workers. In addition to the publications noted above, Minshull et al., U.S. Pat. No. 5,837,458 METHODS AND COMPOSITIONS FOR CELLULAR AND METABOLIC ENGINEERING provides for the evolution of new metabolic pathways and the enhancement of bio-processing through recursive shuffling techniques. Crameri et al. (1996), "Construction And Evolution Of Antibody-Phage Libraries By DNA Shuffling" *Nature Medicine* 2(1):100–103 describe, e.g., antibody shuffling for antibody phage libraries. Additional details regarding DNA shuffling can also be found in various published applications, such as WO95/22625, WO97/20078, WO96/33207, WO97/33957, WO98/27230, WO97/35966, WO98/31837, WO98/13487, WO98/13485 and WO989/42832.

A number of the publications of the inventors and their co-workers, as well as other investigators in the art also describe techniques which facilitate DNA shuffling, e.g., by providing for reassembly of genes from small fragments of genes, or even oligonucleotides encoding gene fragments. In addition to the publications noted above, Stemmer et al. (1998) U.S. Pat. No. 5,834,252 "END COMPLEMENTARY POLYMERASE REACTION" describe processes for amplifying and detecting a target sequence (e.g., in a mixture of nucleic acids), as well as for assembling large polynucleotides from fragments.

Review of the foregoing publications reveals that DNA shuffling is an important new technique with many practical applications. Thus, new techniques which facilitate DNA shuffling are highly desirable. In particular, techniques which reduce the number of physical manipulations needed for shuffling procedures would be particularly useful. The present invention provides significant new DNA shuffling protocols, as well as other features which will be apparent upon complete review of this disclosure.

SUMMARY OF THE INVENTION

The present invention provides new "in silico" DNA shuffling techniques, in which part, or all, of a DNA shuffling procedure is performed or modeled in a computer system, avoiding (partly or entirely) the need for physical manipulation of nucleic acids. These approaches are collectively termed Genetic Algorithm Guided Gene Synthesis or "GAGGS."

In a first aspect, the invention provides methods for obtaining a "chimeric" or "recombinant" polynucleotide or polypeptide (or other bio-polymer) having a desired characteristic. In the methods, at least two parental character strings encoding sequence information for one or more polypeptides and/or for one or more single-stranded or double-stranded polynucleotides are provided. All or a part of the sequences (i.e., one or more subsequence regions) contain areas of identity and areas of heterology. A set of character strings of a pre-defined or selected length is provided that encodes single-stranded oligonucleotide sequences which include overlapping sequence fragments of at least a part of each of the parental character strings, and/or at least a part of polynucleotide strands complementary to the parental character strings.

In one class of embodiments, the invention provides methods of generating libraries of biological polymers. The method include generating diverse population of character strings in a computer, where the character strings are generated by alteration (recombination, mutagenesis, etc.) of pre-existing character strings. The diverse population of character strings is then synthesized to comprise the library of biological polymers (nucleic acids, polypeptides, peptide nucleic acids, etc.). Typically, the members of the library of biological polymers are selected for one or more activity. In one recursive aspect of the invention, an additional library or an additional set of character strings is filtered by subtracting the additional library or the additional set of character strings with members of the library of biological polymers which display activity below a desired threshold. In an additional or complementary recursive aspect of the invention, the additional library or additional set of character strings is filtered by biasing the additional library, or the additional set of character strings, with members of the library of biological polymers which display activity above a desired threshold.

A set of single-stranded oligonucleotides made according to the set of sequences defined in the character strings is provided. Part or all of the single stranded nucleotides produced are pooled under denaturing or annealing conditions, where at least two single-stranded oligonucleotides represent parts of two different parental sequences. The resultant population of the single-stranded oligonucleotides is incubated with a polymerase under conditions which result in annealing of the single-stranded fragments at areas of identity to form pairs of annealed fragments. These areas of identity are sufficient for one member of the pair to prime replication of the other, resulting in an increase in the length of the oligonucleotides. The resulting mixture of double- and single-stranded oligonucleotides are denatured into single-stranded fragments. These steps are repeated, such that at least a part of the resultant mixture of single-stranded chimeric and mutagenized polynucleotides are used in the steps of subsequent cycles. Recombinant polynucleotides having evolved toward a desired property are selected or screened for.

In another aspect, the invention provides for the use of genetic operators, e.g., in a computer. In these methods, sequence strings corresponding to the oligonucleotides noted above are selected by the computer from sequence strings corresponding to one or more of the following sets of single-stranded oligonucleotides:

a) oligonucleotides synthesized to contain randomly or non-randomly pre-selected mutations of the parental sequences according to modified sequences including replacement of one or more characters with another character, or deletion or insertion of one or more characters;

b) oligonucleotide sequences synthesized to contain degenerate, mixed or unnatural nucleotides, at one or more randomly or non-randomly pre-selected positions; and, c) chimeric oligonucleotides synthesized according to artificial sequences of character substrings designed to contain joined partial sequences of at least two parental sequences.

In certain embodiments, oligonucleotides of set (c) contain one or more mutated or degenerate positions defined in sets (a) and (b). The oligonucleotides of set (c) are optionally chimeric nucleotides with crossover points selected according to a method allowing identification of a plurality of character substrings displaying pairwise identity (homology) between any or all of the string pairs comprising sequences of different parental character strings.

Crossover points for making chimeric oligonucleotide sequences are optionally selected randomly, or approximately in the middle of each or a part of the identified pairwise identity (homology) areas, or by any other set of selection criteria.

In one aspect, at least one crossover point for at least one chimeric oligonucleotide sequence is selected from those not within detected identity areas.

In one aspect, the mixtures of single stranded oligonucleotides described above are pooled at least once with an additional set of polynucleotides comprising one or more double-stranded or single-stranded polynucleotide encoded by a part and/or by an entire character string of any of the parental sequences provided, and/or by another character string(s) which contains areas of identity and areas of heterology with any of the parental character strings provided.

The polynucleotides from the additional set of polynucleotides can be obtained by oligonucleotide synthesis of oligonucleotides corresponding to any parental character string (or homolog thereof), or by random fragmentation (e.g., by enzymatic cleavage e.g., by a DNAse, or by chemical cleavage of the polynucleotide) and/or by a restriction-enzyme fragmentation of polynucleotides encoded by character strings defined above, and/or by another character string(s) which contains areas of identity and areas of heterology with any of the parental character strings provided. That is, any nucleic acid generated by GAGGS can be further modified by any available method to produce additionally diversified nucleic acids. Furthermore, any diversified nucleic acid can serve as a substrate for further rounds of GAGGS.

The above methods are suitably adapted to a wide range of lengths for synthetic oligos (e.g., 10–20 nucleotides or more, 20–40 nucleotides or more, 40–60 nucleotides or more, 60–100 nucleotides or more, 100–150 nucleotides or more, etc.), a wide variety of types of parental sequences (e.g., for therapeutic proteins such as EPO, insulin, growth hormones, antibodies or the like; agricultural proteins such as plant hormones, disease resistance factors, herbicide resistance factors (e.g., p450s,) industrial proteins (e.g., those involved in bacterial oil desulfurization, synthesis of polymers, detoxification proteins and complexes, fermentation or the like)) and for a wide variety in the number of selection/screening cycles (e.g., 1 or more cycle, 2 or more cycle, 3–4 or more cycles, 10 or more cycles, 10–50 or more cycles, 50–100 or more cycles, or more than 100 cycles). Rounds of GAGGS evolution can be alternated with rounds of physical nucleic acid shuffling and/or selection assays under various formats (in vivo, or in vitro). Selected nucleic acids (i.e., those with desirable properties) can be deconvoluted by sequencing or other procedures such as restriction enzyme analysis, real-time PCR analysis or the like, so that the processes can be started over using the sequence information to guide gene synthesis, e.g., without any physical manipulation of DNA obtained from previous GAGGS rounds.

Typically in the methods above, synthesis of polynucleotides from single-stranded oligonucleotides is performed by assembly PCR. Other options for making nucleic acids include ligation reactions, cloning and the like.

In typical embodiments, the sets of character strings, encoding single-strand oligonucleotides comprising fragments of parental strings, including chimeric and mutated/degenerate fragments of a pre-defined length, are generated using a device comprising a processing element, such as a computer with software for sequence string manipulation.

In one aspect, the invention provides for single parent GAGGS. These methods are set forth in more detail in the examples herein.

The invention also provides methods of producing recombinant nucleic acids using bridging oligonucleotide selection strategies. In the methods, two or more parental nucleic acid sequences are provided. Cross-over sites are selected for recombination between the two or more parental nucleic acid sequences, thereby defining one or more recombinant nucleic acids that result from a cross-over between at least two of the two or more parental nucleic acids. Corresponding bridging oligonucleotides are defined. A recombinant sequence for at least one of the one or more recombinant nucleic acids is determined. The at least one recombinant sequence is selected in silico for one or more expected activity and the at least one recombinant sequence is synthesized. The synthetic step is typically performed by providing fragments of the two or more parental nucleic acids and at least one of corresponding bridge oligonucleotides, hybridizing the fragments and the bridge oligonucleotides and elongating the hybridized fragments with a polymerase or a ligase. This dramatically simplifies the overall synthesis strategy for creating recombinant nucleic acids between two or more parental sequences, including sequences which display low levels of sequence similarity.

The present invention further provides methods of producing one or more recombinant nucleic acids or encoded polypeptides. In the methods, a plurality of first nucleic acid or first polypeptide sequences are provided. The first nucleic acid or polypeptide sequences optionally comprise homologous or non-homologous sequences, and the sequences can comprise artificial or natural sequences. Cross-over sequences are selected between the plurality of first nucleic acid or first polypeptide sequences by defining structural, statistical, or logical criteria for the cross-over sequences in silico. 104. Defining the structural logical or statistical criteria can include any of a variety of methods set for the herein, including performing structural modeling of at least one of the first polypeptide sequences to define one or more region of structural interest in the at least one first polypeptide sequence and selecting one or more cross-over sequence to preserve or disrupt the region of structural interest; defining a structural or sequence-based motif in at least one of the first polynucleotide or polypeptide sequences to define one or more conserved region in the at least one first polynucleotide or polypeptide sequence and selecting one or more cross-over sequence to preserve or disrupt the motif; identifying one or more nucleotides or amino acids within at least one of the first polynucleotide or polypeptide sequences which shows activity or structural co-variance for one or more desired activities or structural features of the first polynucleotide or polypeptide sequence and selecting one or more cross-over sequence to preserve or disrupt the co-variance; performing an energy minimization analysis of the first polynucleotide or polypeptide sequence and selecting one or more cross-over sequence to preserve or disrupt energy minimization of the first polynucleotide or polypeptide sequence; performing a stability analysis of the first polynucleotide or polypeptide sequence and selecting one or more cross-over sequence to preserve or disrupt stability of the of the first polynucleotide or polypeptide sequence at least one recombinant sequence; comparing an energy minimized model of the first polynucleotide or polypeptide sequence to an energy minimized model of one or more parental nucleic acid from which the first polynucleotide or polypeptide sequence was derived and selecting one or more cross-over sequence to preserve or alter energy minimization of the first polynucleotide or polypeptide sequence; performing protein threading on one or more first polypeptide sequence and selecting the cross-over sequences to maintain or disrupt protein threading; performing one or more of: PDA, a branch-and-terminate combinatorial optimization analysis, a dead end elimination, a genetic or mean-field analysis, or analysis of protein folding by threading, of the least one of the first polynucleotide or polypeptide sequence, or the like.

Generally, a plurality of recombinant nucleic acids comprising or encoding the cross-over sequences are synthesized. This can include, for example, artificially synthesizing a plurality of recombinant nucleic acids comprising or encoding the cross-over sequences comprises synthesizing a plurality or oligonucleotides, one or more of which encodes part or all of one or more of the cross-over sequences. The plurality of oligonucleotides are typically incubated with a polymerase or a ligase (or both a polymerase and a ligase).

BRIEF DESCRIPTION OF THE FIGURES

FIG. 2 is a flow chart describing a portion of directed evolution by GAGGS. The flow chart of FIG. 2 is optionally contiguous from FIG. 1.

FIG. 9 is a chart showing introducing indexed crossover points marker into the sequence of each parent.

DETAILED DESCRIPTION

Figure 1A:
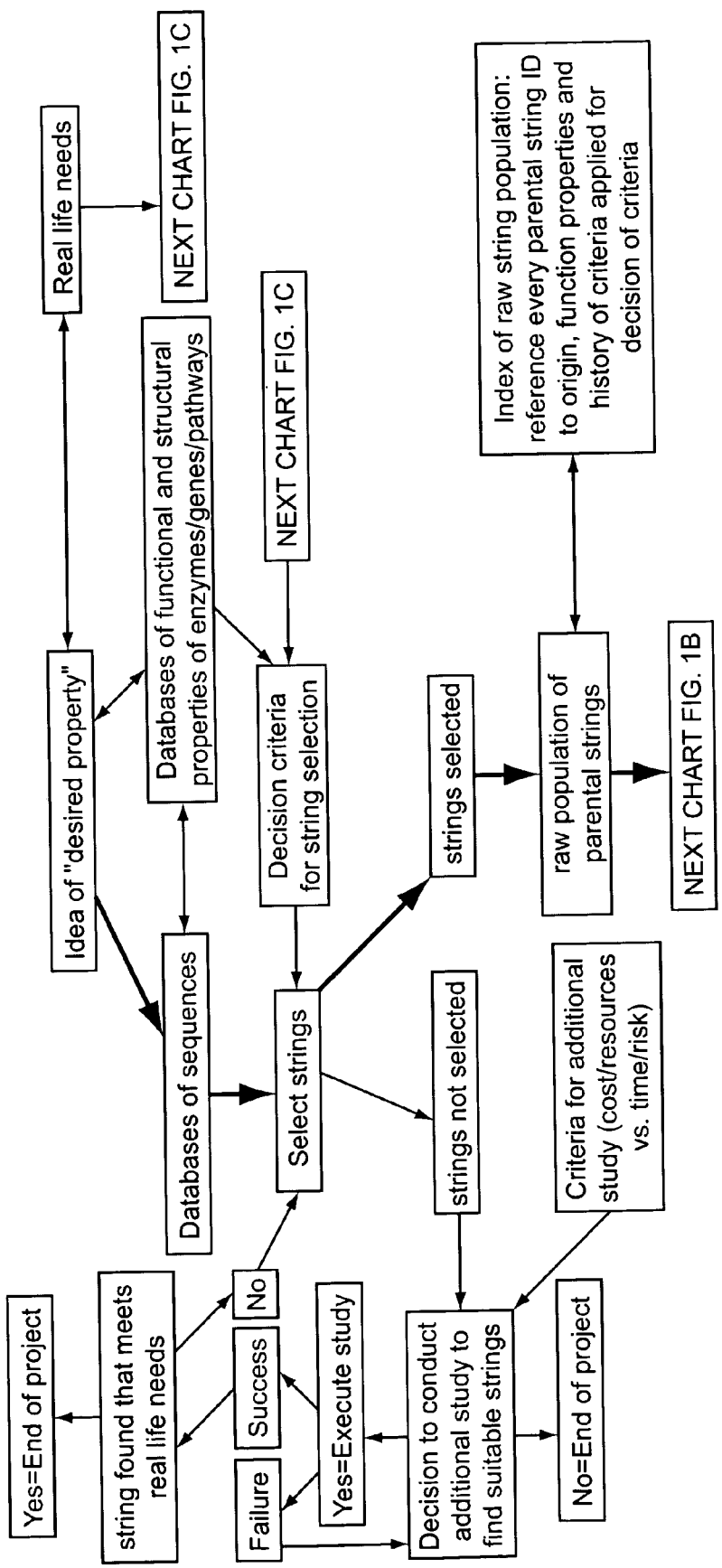
FIG. 1 is a flow chart describing a portion of directed evolution by GAGGS.

In the methods of the invention, "genetic" or "evolutionary" algorithms are used to produce sequence strings which can be converted into physical molecules, shuffled and tested for a desired property. This greatly expedites forced evolution procedures, as the ability to pre-select substrates for shuffling reduces actual physical manipulation of nucleic acids in shuffling protocols. In addition, the use of character strings as "virtual substrates" for shuffling protocols, when coupled with gene reconstruction methods, eliminates the need to obtain parental physical molecules encoding genes.

Genetic algorithms (GAs) are used in a wide variety of fields to solve problems which are not fully characterized or which are too complex to allow for full characterization, but for which some analytical evaluation is available. That is, GAs are used to solve problems which can be evaluated by some quantifiable measure for the relative value of a solution (or at least the relative value of one potential solution in comparison to another). The basic concept of a genetic algorithm is to encode a potential solution to a problem as a series of parameters. A single set of parameter values is treated as the "genome" or genetic material of an individual solution. A large population of candidate solutions are created. These solutions can be bred with each other for one or more simulated generations under the principle of survival of the fittest, meaning the probability that an individual solution will pass on some of its parameter values to subsequent solution sets is directly related to the fitness of the individual (i.e., how good that solution is relative to the others in the population for the selected parameter). Breeding takes place through use of operators such as crossovers which simulate basic biological recombination, and mutation. The simple application of these operators with reasonable selection mechanisms has produced startlingly good results over a wide range of problems.

An introduction to genetic algorithms can be found in David E. Goldberg (1989) *Genetic Algorithms in Search, Optimization and Machine Learning* Addison-Wesley Pub Co; ISBN: 0201157675 and in Timothy Masters (1993) *Practical Neural Network Recipes in C++* (Book&Disk edition) Academic Pr; ISBN: 0124790402. A variety of more recent references discuss the use of genetic algorithms used to solve a variety of difficult problems. See, e.g., garage.cse.msu.edu/papers/papers-index.html (on the world wide web) and the references cited therein; gaslab.cs.unr.edu/ (on the world wide web) and the references cited therein; aic.nrl.navy.mil/(on the world wide web) and the references cited therein; cs.gmu.edu/research/gag/ (on the world wide web) and the references cited therein and cs.gmu.edu/research/gag/pubs.html (on the world wide web) and the references cited therein.

In the present invention, a genetic algorithm (GA) is used to provide a character string-based representation of the process of generating biopolymer diversity (computational evolution of character strings by application of one or more genetic operators to a provided population (e.g., a parent library) of character strings, e.g. gene sequences).

A representation of a GA-generated character string population (or "derivative library") is used as a sequence instruction set in a form suitable to control polynucleotide synthesis (e.g. via non-error-prone synthesis, error-prone synthesis, parallel synthesis, pooled synthesis, chemical synthesis, chemoenzymatic synthesis, (including assembly PCR of synthetic oligonucleotides), and the like). Synthesis of polynucleotides is conducted with sequences encoded by a character string in the derivative library. This creates a physical representation (a library of polynucleotides) of the computation-generated "gene" (or any other character string) diversity.

Physical selection of the polynucleotides having desired characteristics is also optionally (and typically) conducted. Such selection is based on results of physical assays of properties of polynucleotides, or polypeptides, whether translated in-vitro, or expressed in-vivo.

Sequences of those polynucleotides found to have desired characteristics are deconvoluted (e.g., sequenced, or, when positional information is available, by noting the position of the polynucleotide). This is performed by DNA sequencing, by reading a position on an array, real time PCR (e.g., TaqMan), restriction enzyme digestion, or any other method noted herein, or currently available.

These steps are optionally repeated, e.g., for 1–4 or more cycles, each time optionally using the deconvoluted sequences as an information source to generate a new, modified set of character strings to start the procedure with. Of course, any nucleic acid which is generated in silico can be synthesized and shuffled by any known DNA shuffling method, including those taught in the references by the inventors and their co-workers cited herein. Such synthesized DNAs can also be mutagenized or otherwise modified according to existing techniques.

In summary, GAGGS is an evolutionary process which includes an information manipulation step (application of a genetic algorithm to a character string representing a biopolymer such as a nucleic acid or protein), to create a set of defined information elements (e.g., character strings) which serve as templates for synthesizing physical nucleic acids. The information elements can be placed into a database or otherwise manipulated in silico, e.g., by the recursive application of a GA to the sequences which are produced. Corresponding physical nucleic acids can be subjected to recombination/selection or other diversity generating procedures, with the nucleic acids being deconvoluted (e.g., sequenced or otherwise analyzed) and the overall process repeated, as appropriate, to achieve a desired nucleic acid.

Example Advantages of GAGGS

There are a variety of advantages to GAGGS as compared to the prior art. For example, physical access to genes/organisms is not required for GAGGS, as sequence information is used for oligo design and selection. A variety of public databases provide extensive sequence information, including, e.g., Genbank™ and those noted supra. Additional sequence databases are available on a contract basis from a variety of companies specializing in genomic information generation and storage.

Similarly, sequences from inaccessible, non-cultivable organisms can be used for GAGGS. For example, sequences from pathogenic organisms can be used without actual handling of the pathogens. All of the sequence types suitable for physical DNA shuffling, including damaged and incomplete genes (e.g., pseudo genes), are amenable to GAGGS.

All genetic operators, including different types of mutagenesis and crossovers can be fully and independently controlled in a reproducible fashion, removing human error and variability from physical experiments with DNA manipulations. GAGGS has applicability to the self-learning capability of artificial intelligence (optimization algorithm output parameter profiles based on feedback entry of yields, success rates and failures of physical screens, etc.).

In GAGGS procedures, sequences with frame-shift mutations (which are generally undesirable) are eliminated or fixed (discarded from the character set, or repaired, in silico). Similarly, entries with premature terminations are discarded or repaired and entries with loss of sequence features known to be important for display of a desired property (e.g. conservative ligands for metal binding) are discarded or repaired.

Furthermore, wild-type parents do not contaminate derivative libraries with multiple redundant parental molecules, as, in one preferred embodiment, only a priori modified genes are subjected to physical shuffling and/or screening (which, in some cases can be expensive, or low throughput, or otherwise less than ideal, depending on the assay available).

In addition, because no actual physical recombination is required, protein sequences can be shuffled in the same way in silico as nucleic acid sequences, and retrotranslation of the resulting shuffled sequences can be used to alleviate codon usage problems and to minimize the number of oligos needed to build one or more library of coding nucleic acids. In this regard, protein sequences can be shuffled in silico using genetic operators that are based on recognition of structural domains and folding motifs, rather than being bound by annealing-based homology criteria of DNA sequences, or simple homology of AA sequences. Furthermore, rational structure-based biases are easily incorporated in library construction, when such information is available.

The only significant operational costs of running GAGGS is the cost of synthesis of large libraries of genes represented in silico. Synthetic assembly of genes can be done, e.g., by assembly PCR from 40–60 bp oligos, which can be synthesized inexpensively by current techniques.

Directed Evolution by GAGGS:

All changes in any DNA sequence during any evolutionary process can be described by a finite number of events, each resulting from action of an elementary genetic operator. In any given parental sequence subspace, these changes can accurately be accounted for and simulated in a physical representation of an evolutionary process aimed to generate sequence diversity for subsequent physical screening for desired characteristics. Physical double stranded polynucleotides are not required for starting GAGGS processes; instead, they are generated following initial GAGGS processes with the purpose of physical screening and/or selection, and/or as a result of this screening or selection. Generating very large libraries for screening/selection is not required.

Genetic Algorithms (GA).

CHARACTER STRINGS: in general, a character string can be any representation of an array of characters (e.g., a linear array of characters provides "words" while a non-linear array can be used as a code to generate a linear array of characters). For practicing GAGGS, character strings are preferably those which encode polynucleotide or polypeptide strings, directly or indirectly, including any encrypted strings, or images, or arrangements of objects which can be transformed unambiguously to character strings representing sequences of monomers or multimers in polynucleotides, polypeptides or the like (whether made of natural or artificial monomers).

GENETIC ALGORITHM: Genetic algorithms generally are processes which mimic evolutionary processes. Genetic algorithms (GAs) are used in a wide variety of fields to solve problems which are not fully characterized or too complex to allow full characterization, but for which some analytical evaluation is available. That is, GAs are used to solve problems which can be evaluated by some quantifiable measure for the relative value of a solution (or at least the relative value of one potential solution in comparison to another). In the context of the present invention, a genetic algorithm is a process for selecting or manipulating character strings in a computer, typically where the character string can be corresponded to one or more biological polymer (e.g., a nucleic acid, protein, PNA, or the like). A biological polymer is any polymer which shares some structural features with naturally occurring polymers such as an RNAs, DNAs and polypeptides, including, e.g., RNAs, RNA analogues, DNAs, DNA analogues, polypeptides, polypeptide analogues, peptide nucleic acids, etc.

Directed Evolution of Character Strings or Objects:

A process of artificially changing a character string by artificial selection, i.e., which occurs in a reproductive population in which there are (1) varieties of individuals, with some varieties being (2) heritable, of which some varieties (3) differ in fitness (reproductive success determined by outcome of selection for a predetermined property (desired characteristic).

The reproductive population can be, e.g., a physical population or a virtual population in a computer system.

GENETIC OPERATORS (GOs): user-defined operations, or sets of operations, each comprising a set of logical instructions for manipulations of character strings. Genetic operators are applied to cause changes in populations of individuals in order to find interesting (useful) regions of the search space (populations of individuals with predetermined desired properties) by predetermined means of selection. Predetermined (or partially predetermined) means of selection include computational tools (operators comprising logical steps guided by analysis of information describing libraries of character strings), and physical tools for analysis of physical properties of physical objects, which can be built (synthesized) from matter with the purpose of physically creating a representation of information describing libraries of character strings. In a preferred embodiment, some or all of the logical operations are performed in a computer.

Genetic Operators

All changes in any population of any type of character strings (and thus in any physical properties of physical objects encoded by such strings) can be described as a result of random and/or predetermined application of a finite set of logical algebraic functions comprising various types of genetic operators.

In its mathematical nature, this statement is not a postulated abstract axiom. In fact, this statement is a derivative theorem with stringent formal proof readily derived from Wiles' proof of Fermat's last theorem. The fundamental implication of the Wiles' Proof for evolutionary molecular biology is in the proof of the central conjecture stating that all elliptic curves are in essence modular forms. Particularly, all of the diversity and evolution of living matter in the universe (i.e., the plurality of objects whose properties can be described by a finite number of elliptical curves) can be described in the language of five basic arithmetic operations: addition, subtraction, multiplication, division and modular forms (i.e., evolution of life can be effectively described by a finite combination of simple changes of information in a finite population of character strings, e.g. all DNA in the universe). This being the case, it is possible to determine the language of nucleic acid-based forms of life, and to define all basic types of genetic operators which apply to nucleic acids under evolutionary selection.

Mathematical modeling of certain genetic operations have been proposed, e.g., in Sun (1999) "Modeling DNA Shuffling" *Journal of Computational Biology* 6(1):77–90; Kelly et al. (1994) "A test of the Markovian model of DNA evolution" *Biometrics* 50(3):653–64; Boehnke et al. (1991) "Statistical methods for multipoint radiation hybrid mapping" *Am. J. Hum. Genet.* 49:1174–1188; Irvine et al. (1991) "SELEXION: systematic evolution of ligands by exponential enrichment with integrated optimization by non-linear analysis" *J. Mol. Biol.* 222:739–761; Lander and Waterman (1988) Genomic mapping by fingerprinting random clones: a mathematical analysis" *Genomics* 2:231–239; Lange (1997) *Mathematical and Statistical Methods for Genetic Analysis* Springer Verlag, N.Y.; Sun and Waterman (1996) "A mathematical analysis of in vitro molecular selection-amplification" *J. Mol. Biol.* 258:650–660; Waterman (1995) *Introduction to Computational Biology* Chapman and Hall, London, UK.

The following provides a description of certain basic genetic operations applicable to the present invention.

MULTIPLICATION (including duplication and replication) is a form of reproduction of character strings, producing additional copies of character strings comprising parental population/library of strings. Multiplication operators can have many variations. They can be applied to individual strings or to groups of identical or non-identical strings. Selecting groups of strings for multiplication can be random or biased.

MUTATION: all mutation types in each member of a set of strings can be described by several simple operations which can be reduced to elements comprising replacement of one set of the characters with another set of characters. One or more characters can be mutated in a single operation. When more than one character is mutated, the set of characters may or may not be continuous over an entire string length (a feature useful to simulate closely clustered mutations by certain chemical mutagens). A Single point mutation operator replaces a single character with another single character. The nature of the new characters can vary, and they can be from the same set of characters making up parental strings, or from different, (e.g., to represent degenerate nucleobases, unnatural nucleobases or amino acids, etc). A Deletion mutation is a more complex operator which removes one or more characters from strings. Individual single point deletions in nucleic acid-encoding strings may be not desirable for manipulating strings representing polynucleotide sequences; however, 3× clustered (continuous or dispersed) deletions may be acceptable ("triple deletion frameshifts"). Single point deletions, though, are useful and acceptable for evolutionary computation of strings encoding polypeptides. Insertion mutations are operationally similar to deletions, except that one or more new characters are inserted. The nature of the added characters optionally vary, and they can be from the same set of characters making up parental strings, or from different, (e.g., to represent degenerate nucleobases, unnatural nucleobases or amino acids, etc). Death can simply be defined as a variation of the deletion operator. It takes place when the result of an application of a genetic operator (or combinations thereof) yields a deletion of an entire individual character string, or entire (sub) population of character strings. Death can also be defined as a variation of an elitism-prone multiplication operator (multiplication of values defining abundance level of one or more strings by zero). Death can also be defined as a default non-selection action in operators, effecting selections of sub-populations of string and transfer manipulations with various sorting and indexing operations of indexed libraries of strings (all non-transferred strings can be considered as dead or non-existent for subsequent computations).

FRAGMENTATION OF STRINGS are an important class of non-elemental (complex) optional operators which can have advantages for simulating evolution of strings in various formats of DNA shuffling. Operationally, fragmentation can be described as a formal variation of a combination of a deletion operator and a multiplication operator. One of skill will appreciate, however, that there are many other simple algorithmic operations which allow any given character string be fragmented to give a progeny of shorter strings. Fragmentation operations may be random or biased. Different ranges of fragment sizes can be predetermined. String fragments may be left in the same population with parental stings, or they may be transferred to different population. Strings fragments from various population strings can be pooled to from new populations.

CROSSOVER (RECOMBINATION)— This operator formally comprises joining a continuous part of one string with a continuous part of another string in such a way that one or two hybrid strings are formed (chimeras), where each of the chimeras contain at least two connected continuous string areas each comprising partial sequence of two different recombining strings. The area/point where sequence characters from different parental strings, is termed the crossover/recombination area/point. Crossover operations can be combined with mutation operations affecting one or more characters of the recombined strings in a proximity of the crossover area/point of joining. When applied recursively to a population of character strings, complex chimeras comprising consequently connected partial sequences of more than two parental strings can be formed.

LIGATION is a variation of an insertion mutation operator where essentially the entire content of one string is combined with the entire content of another string in a way that the last character of one string is followed by the first character of another string. Ligation operation can be combined with mutation operation affecting one or more characters of the ligated strings in a proximity of the point of joining. Ligation can also be viewed as a means of forming chimeras.

ELITISM is a concept that provides a useful form of bias which imposes discriminating criteria for use of any of the genetic operators, and various types of positive and negative biases can be designed and implemented. The rational for the design of elitist operators is based on the concept of fitness. Fitness can be determined using string analysis tools which recognize various sequence-specific features (GC— content, frameshifts, terminations, sequence length, specific substrings, homology properties, ligand-binding and folding motifs, etc) and/or indexed correlated parameters acquired from physical selection of physical representations of character strings (enzyme activity, stability, ligand binding, etc.). It is understood that different elitism criteria can be applied separately to any of the above described genetic operators, or combinations of operators. It is also possible to use elitism, in the same evolutionary computation process, with several operators of the same type, where input/output parameters of each of the similar operators can be controlled independently (or interdependently). Different elitism criteria can be used to control changes in the string character populations caused by action of each of the individual operators.

SEQUENCE HOMOLOGY or SEQUENCE SIMILARITY is an especially important form of sequence-specific elitism useful for controlling changes in populations of character strings caused by crossover/recombination operators in those genetic algorithms used to evolve character strings encoding polynucleotide and polypeptide sequences.

Various approaches, methods and algorithms known in the art can be used to detect homology or similarity between different character strings. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by even by visual inspection (see generally, Ausubel et al., infra).

One example algorithm that is suitable for determining percent sequence identity and sequence similarity is the BLAST algorithm, which is described in Altschul et al., *J. Mol. Biol.* 215:403–410 (1990). Software for performing BLAST analyses is publicly available through the National Center for Biotechnology Information (ncbi.nlm.nih.gov/ on the world wide web). This algorithm involves first identifying high scoring sequence pairs (HSPs) by identifying short words of length W in the query sequence, which either match or satisfy some positive-valued threshold score when aligned with a word of the same length in a database sequence. T is referred to as the neighborhood word score threshold (Altschul et al., supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff (1989) *Proc. Natl. Acad. Sci. USA* 89:10915).

In addition to calculating percent sequence identity, the BLAST algorithm also performs a statistical analysis of the similarity between two sequences (see, e.g., Karlin & Altschul (1993) *Proc. Nat'l. Acad. Sci. USA* 90:5873–5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence (and, therefore, homologous) if the smallest sum probability in a comparison of the test nucleic acid to the reference nucleic acid is less than about 0.1, or less than about 0.01, and or even less than about 0.001.

An additional example of a useful sequence alignment algorithm is PILEUP. PILEUP creates a multiple sequence alignment from a group of related sequences using progressive, pairwise alignments. It can also plot a tree showing the clustering relationships used to create the alignment. PILEUP uses a simplification of the progressive alignment method of Feng & Doolittle, *J. Mol. Evol.* 35:351–360 (1987). The method used is similar to the method described by Higgins & Sharp, CABIOS5:151–153 (1989). The program can align, e.g., up to 300 sequences of a maximum length of 5,000 letters. The multiple alignment procedure begins with the pairwise alignment of the two most similar sequences, producing a cluster of two aligned sequences. This cluster can then be aligned to the next most related sequence or cluster of aligned sequences. Two clusters of sequences can be aligned by a simple extension of the pairwise alignment of two individual sequences. The final alignment is achieved by a series of progressive, pairwise alignments. The program can also be used to plot a dendogram or tree representation of clustering relationships. The program is run by designating specific sequences and their amino acid or nucleotide coordinates for regions of sequence comparison.

Thus, different types of similarity of with various levels of identity and length can be detected and recognized. For example, many homology determination methods have been designed for comparative analysis of sequences of biopolymers, for spell-checking in word processing, and for data retrieval from various databases. With an understanding of double-helix pair-wise complement interactions among 4 principal nucleobases in natural polynucleotides, models that simulate annealing of complementary homologous polynucleotide strings can also be used as a foundation of sequence-specific elitism useful for controlling crossover operators.

Homology-based elitism of crossover operators can thus be used (a) to find suitable recombination pairs of strings in a population of strings, and/or (b) to find/predetermine particularly suitable/desired areas/points of recombination over lengths of character strings selected for recombination.

Setting predetermined types and stringency of similarity/homology as a condition for crossover to occur is a form of elitism for control of formation of chimeras between representative parental character strings of various degree of homology.

RECURSIVE USE OF GENETIC OPERATORS FOR EVOLUTION OF CHARACTER STRINGS. All of the described genetic operators can be applied in a recursive mode, and specific parameters for each application occurrence can remain the same or can be systematically or randomly varied.

RANDOMNESS IN THE APPLICATION OF GENETIC OPERATORS FOR EVOLUTION OF CHARACTER STRINGS. Each genetic operator can be applied to randomly selected strings and/or to randomly selected positions over one or more string's length, with occurrence frequencies randomly selected within a range.

ARRANGEMENT OF GOS IN GAS. Order determining applications of individual GOs to product derivative libraries of character strings may be different and may depend on the composition of a particular set of individual GOs selected for practicing various formats of GAGGS. The order may be linear, cyclic, parallel, or a combination of the three and can typically be represented by a graph. Many GO arrangements can be used to simulate natural sexual and mutagenic processes for generating genetic diversity, or artificial protocols, such as single-parent or family DNA shuffling. However, the purpose of GA is not in limited to simulation of some known physical DNA manipulation methods. Its main aim is in the provision of a formal and intelligent tool, based on understanding natural and artificial evolution processes, for creation and optimization of evolutionary protocols of practical utility which may provide effective advantages over currently practiced methods.

Gene Synthesis.

The physical synthesis of genes encoded by derivative libraries of character strings, obtained by operation of genetic algorithms, is the primary means to create a physical representation of matter that is amenable to a physical assay for a desired property or to produce substrates that are further evolved in physical diversity generation procedures. Thus, one aspect of the present invention relates to the synthesis of genes with sequences selected following one or more computer shuffling procedure as set forth herein.

For GAGGS to be a time and resource effective technology, gene synthesis technology is used, typically to construct libraries of genes in a consistent manner, and in close adherence to the sequence representations produced by GA manipulations. GAGGS typically uses gene synthesis methods which allow for rapid construction of libraries of $10^4$–$10^9$ "gene" variations. This is typically adequate for screening/selection protocols, as larger libraries are more difficult to make and maintain and sometimes cannot be as completely sampled by a physical assay or selection method. For example, existing physical assay methods in the art (including, e.g., "life-and-death" selection methods) generally allow sampling of about 109 variations or less by a particular screen of a particular library, and many assays are effectively limited to sampling of $10^4$–$10^5$ members. Thus, building several smaller libraries is a preferred method, as large libraries cannot easily be completely sampled. However, larger libraries can also be made and sampled, e.g., using high-throughput screening methods.

Gene Synthesis Technologies

There are many methods which can be used to synthesize genes with well-defined sequences. Solely for the purpose of clarity of illustration, this section focuses on one of the many possible and available types of known methods for synthesis of genes and polynucleotides.

Current art in polynucleotide synthesis is best represented by well-known and mature phosphoramidite chemistry which permits effective oligo perparation. It is possible, but somewhat impractical, to use this chemistry for routine synthesis of oligos significantly longer than 100 bp, as the quality of sequence deteriorates for longer oligos, with longer synthetic oligos generally being purified before use. Oligos of a "typical" 40–80 bp size can be obtained routinely and directly with very high purity, and without substantial sequence deterioration.

For example, oligonucleotides e.g., for use in in vitro amplification/gene reconstruction methods, for use as gene probes, or as shuffling targets (e.g., synthetic genes or gene segments) are typically synthesized chemically according to the solid phase phosphoramidite triester method described by Beaucage and Caruthers (1981), *Tetrahedron Letts.*, 22(20):1859–1862, e.g., using an automated synthesizer, as described in Needham-VanDevanter et al. (1984) *Nucleic Acids Res.*, 12:6159–6168. Oligonucleotides can also be custom made and ordered from a variety of commercial sources known to persons of skill. There are many commercial providers of oligo synthesis services, and thus this is a broadly accessible technology. Any nucleic acid can be custom ordered from any of a variety of commercial sources, such as The Midland Certified Reagent Company (mcrc@oligos.com), The Great American Gene Company (genco.com, on the world wide web), ExpressGen Inc. (expressgen.com, on the world wide web), Operon Technologies Inc. (Alameda, Calif.) and many others. Similarly, peptides and antibodies can be custom ordered from any of a variety of sources, such as PeptidoGenic (pkim@ccnet.com), HTI Bio-products, inc. (htibio.com, on the world wide web), BMA Biomedicals Ltd (U.K.), Bio-Synthesis, Inc., and many others.

As described herein, synthetic shuffling using nucleic acid ligases or polymerases allows great freedom of oligo design and generation of relevant mixtures. Further, synthetic and assembly parameters permits considerable control over library design. Whether polymerase mediated or ligase mediated assembly methods (or a combination thereof) are used, oligos for libraries assembled by DNA ligase are synthesized, e.g., by conventional chemistry, by split-pool synthesis, or use of trinucleotide phosphoramidites, as described herein. See also, "OLIGONUCLEOTIDE MEDIATED NUCLEIC ACID RECOMBINATION" by Crameri et al., Filed Jan. 18, 2000, USSN PCT/US00/01203 and "USE OF CODON VARIED OLIGONUCLEOTIDE SYNTHESIS FOR SYNTHETIC SHUFFLING" by Welch et al., U.S. Ser. No. 09/408,393, filed Sep. 28, 1999. The oligos are then assembled into full-length sequences of interest. Oligo mixtures can be spiked with partial or full-length homologous sequences (e.g., single or double-stranded sequences) e.g., from naturally occurring, synthetic or cloned sequences, to facilitate gene reassmbly methods.

In any case, polymerase mediated, ligation-mediated and combination ligation/polymerase mediated assembly methods are suitable for construction of individual sequences and/or synthetic libraries (see also, "OLIGONUCLEOTIDE MEDIATED NUCLEIC ACID RECOMBINATION" by Crameri et al., Filed Jan. 18, 2000, USSN PCT/US00/01203). For example, in certain ligation mediated methods, top and bottom strand oligos can be designed to be overlapping, but with the oligos for each strand being abutting, rather than overlapping, as in typical polymerase-mediated assembly reactions. To facilitate ligation-mediated reactions, oligos are optionally phosphorylated, e.g., with a phosphorylase or a kinase enzyme, or by chemical addition of a phosphate during or following oligonucleotide synthesis. Phosphorylated oligos are assembled with a DNA ligase, e.g., $T_4$ DNA ligase or another available DNA ligase. Either thermostable or thermolabile ligases can be used.

In one gene assembly embodiment, a ligation chain reaction (LCR) can be performed to achieve assembly, e.g., where a thermostable ligase is used for assembly. An example of an LCR-mediated gene synthesis approach is described by Au et al. (1998) "Gene Synthesis by a LCR-Based Approach: High level Production of Leptin-L54 Using Synthetic Gene in *Escheria coli*" *Biochemical and Biophysical Research Communications* 248:200–203. The gene synthetic strategies described supra and in "OLIGO-NUCLEOTIDE MEDIATED NUCLEIC ACID RECOMBINATION" by Crameri et al., *Filed Jan.* 18, 2000, USSN PCT/US00/01203 are generally applicable to both ligation and polymerase-mediated synthetic methods.

Another relevant demonstration of total gene synthesis from small fragments which is readily amenable to optimization, parallelism and high throughout is set forth in Dillon and Rosen (*Biotechniques*, 1990, 9(3)298–300). Simple and rapid PCR-based assembly process of a gene from a set of partially overlapping single-strand oligonucleotides, with or without use of ligase, can be performed. Several groups have also described successful applications of variations the same PCR-based gene assembly approach to the synthesis of various genes of increasing size, thus demonstrating its general applicability and its combinatorial nature for synthesis of libraries of mutated genes. Useful references include Sandhu, et al. (*Biotechniques*, 1992, 12(1)15–16), (220 bp gene from 3 oligos of 77–86 bp); Prodromou and Pearl (*Protein Engineering*, 1992, 5(8)827–829 (522 bp gene, from 10 oligos of 54–86 bp); Chen et al, 1994 (*JACS*, 1194(11):8799–8800), (779 bp gene); Hayashi et al, 1994 (*Biotechniques*, 1994, 17:310–314) and others.

More recently Stemmer et al (*Gene*, 1995, 164:49–53) showed that, e.g., PCR-based assembly methods are effectively useful to build larger genes of up to at least 2.7 kb from dozens or even hundreds of synthetic 40 bp oligos. These authors also demonstrated that, from four basic steps comprising PCR-based gene synthesis protocols (oligo synthesis, gene assembly, gene amplification, and, optionally, cloning) the gene amplification step can be omitted, if a 'circular' assembly PCR is used.

A number of the publications of the inventors and their co-workers, as well as other investigators in the art also describe techniques which facilitate DNA shuffling, e.g., by providing for reassembly of genes from small fragments, or even oligonucleotides. One aspect of the present invention is the ability to use family shuffling oligonucleotides and cross over oligonucleotides as recombination templates/intermediates in various DNA shuffling methods.

Indeed, a number of the publications by the inventors and their co-workers, as well as other investigators in the art also describe techniques which facilitate reassembly of genes from small fragments, including oligonucleotides. In addition to the publications noted above, Stemmer et al. (1998) U.S. Pat. No. 5,834,252 END COMPLEMENTARY POLYMERASE REACTION describe processes for amplifying and detecting a target sequence (e.g., in a mixture of nucleic acids), as well as for assembling large polynucleotides from fragments. Crameri et al. (1998) *Nature* 391: 288–291 provides basic methodologies for gene reassembly, as does Crameri et al. (1998) *Bio techniques* 18(2): 194–196.

More recently, a number of gene reassembly protocols which simultaneously recombine and reconstruct genes have been described in several applications of the inventors and their co-workers, such as "OLIGONUCLEOTIDE MEDIATED NUCLEIC ACID RECOMBINATION" by Crameri et al., filed Feb. 5, 1999 (U.S. Ser. No. 60/118,813) and filed Jun. 24, 1999 (U.S. Ser. No. 60/141,049) and filed Sep. 28, 1999 (U.S. Ser. No. 09/408,392) and "USE OF CODON-BASED OLIGONUCLEOTIDE SYNTHESIS FOR SYNTHETIC SHUFFLING" by Welch et al., filed Sep. 28, 1999 (U.S. Ser. No. 09/408,393). In these embodiments, synthetic recombination methods are used, in which oligonucleotides corresponding to different homologues are synthesized and reassembled in PCR or ligation reactions which include oligonucleotides which correspond to more than one parental nucleic acid, thereby generating new recombined nucleic acids.

One advantage of oligonucleotide-mediated recombination is the ability to recombine homologous nucleic acids with low sequence similarity, or even to recombine non-homologous nucleic acids. In these low-homology oligonucleotide shuffling methods, one or more set of fragmented nucleic acids is recombined, e.g., with a set of crossover family diversity oligonucleotides. Each of these crossover oligonucleotides have a plurality of sequence diversity domains corresponding to a plurality of sequence diversity domains from homologous or non-homologous nucleic acids with low sequence similarity. The fragmented oligonucleotides, which are derived by comparison to one or more homologous or non-homologous nucleic acids, can hybridize to one or more region of the crossover oligos, facilitating recombination. Such oligonucleotide sets are selected in silico according to the methods herein.

When recombining homologous nucleic acids, sets of overlapping family gene shuffling oligonucleotides (which are derived by comparison of homologous nucleic acids and synthesis of oligonucleotide fragment sets, which correspond to regions of similarity and regions of diversity derived from the comparison) are hybridized and elongated (e.g., by reassembly PCR), providing a population of recombined nucleic acids, which can be selected for a desired trait or property. Typically, the set of overlapping family shuffling gene oligonucleotides include a plurality of oligonucleotide member types which have consensus region subsequences derived from a plurality of homologous target nucleic acids.

Typically, family gene shuffling oligonucleotide are provided by aligning homologous nucleic acid sequences to select conserved regions of sequence identity and regions of sequence diversity. A plurality of family gene shuffling oligonucleotides are synthesized (serially or in parallel) which correspond to at least one region of sequence diversity. Further details regarding family shuffling is found in U.S. Ser. No. 09/408,392, cited above.

Sets of fragments, or subsets of fragments used in oligonucleotide shuffling approaches can be provided by cleaving one or more homologous nucleic acids (e.g., with a DNase), or, more commonly, by synthesizing a set of oligonucleotides corresponding to a plurality of regions of at least one nucleic acid (typically oligonucleotides corresponding to a full-length nucleic acid are provided as members of a set of nucleic acid fragments). In the shuffling procedures herein, these cleavage fragments can be used in conjunction with family gene shuffling oligonucleotides, e.g., in one or more recombination reaction to produce recombinant nucleic acids.

Gene assembly by PCR from single-strand complementary overlapping synthetic oligos is a method of choice for practicing in GAGGS. Optimization of this method can be performed e.g., including varying oligo length, the number of oligos in the recombination reaction, the degree of oligonucleotide overlap, levels and nature of sequence degeneracy, specific reaction conditions and particular polymerase enzymes used in the reassembly, and in controlling the stringency of gene assembly to decrease or increase the number of sequence deviations during gene synthesis.

The method can also be practiced in a parallel mode where each of the individual library members, including a plurality of the genes intended for subsequent physical screening, are synthesized in spatially separated vessels, or arrays of vessels, or in a poolwise fashion, where all, or part, of the desired plurality of genes are synthesized in a single vessel. Many other synthesis methods for making synthetic nucleotides are also known, and specific advantages of use of one vs. another for practicing GAGGS may be readily determined by one skilled in the art.

Sequence Deconvolution.

Sequence deconvolution is performed on those variants of polynucleotides which are found to have desired properties, in order to confirm changes in corresponding character strings (i.e., corresponding to physical sequences for biopolymers) yielding desired changes in the relevant composition of matter (e.g., a polynucleotide, polypeptide, or the like).

Sequencing and other standard recombinant techniques useful for the present invention, including for sequence deconvolution are found, e.g., in Berger and Kimmel, *Guide to Molecular Cloning Techniques*, Methods in Enzymology volume 152 Academic Press, Inc., San Diego, Calif. (Berger); Sambrook et al., *Molecular Cloning—A Laboratory Manual* (2nd Ed.), Vol. 1–3, Cold Spring Harbor Laboratory, Cold Spring Harbor, N.Y., 1989 ("Sambrook") and *Current Protocols in Molecular Biology*, F. M. Ausubel et al., eds., Current Protocols, a joint venture between Greene Publishing Associates, Inc. and John Wiley & Sons, Inc., (supplemented through 1999) ("Ausubel")). In addition to sequencing GAGGS products, unique restriction sites can also be used for detecting particular sequences. Sufficient information to guide one of skill through restriction enzyme digestion is also found in Sambrook, Berger and Ausubel, id.

Methods of transducing cells, including plant and animal cells, with GAGGS generated nucleic acids, e.g., for cloning and sequencing and/or for expression and selection of encoded molecules are generally available, as are methods of expressing proteins encoded by such nucleic acids. In addition to Berger, Ausubel and Sambrook, useful general references for culture of animal cells include Freshney (*Culture of Animal Cells, a Manual of Basic Technique*, third edition Wiley-Liss, New York (1994)) and the references cited therein, Humason (*Animal Tissue Techniques*, fourth edition W.H. Freeman and Company (1979)) and Ricciardelli, et al., *In Vitro Cell Dev. Biol.* 25:1016–1024 (1989). References for plant cell cloning, culture and regeneration include Payne et al. (1992) *Plant Cell and Tissue Culture in Liquid Systems* John Wiley & Sons, Inc. New York, N.Y. (Payne); and Gamborg and Phillips (eds) (1995) *Plant Cell, Tissue and Organ Culture; Fundamental Methods* Springer Lab Manual, Springer-Verlag (Berlin Heidelberg N.Y.) (Gamborg). A variety of Cell culture media are described in Atlas and Parks (eds) The Handbook of Microbiological Media (1993) CRC Press, Boca Raton, Fla. (Atlas). Additional information for plant cell culture is found in available commercial literature such as the *Life Science Research Cell Culture Catalogue* (1998) from Sigma-Aldrich, Inc (St Louis, Mo.) (Sigma-LSRCCC) and, e.g., the *Plant Culture Catalogue* and supplement (1997) also from Sigma-Aldrich, Inc (St Louis, Mo.) (Sigma-PCCS).

In vitro amplification methods can also be used to amplify and/or sequence GAGGS generated nucleic acids, e.g., for cloning, and selection. Examples of techniques sufficient to direct persons of skill through typical in vitro amplification and sequencing methods, including the polymerase chain reaction (PCR) the ligase chain reaction (LCR), Qβ-replicase amplification and other RNA polymerase mediated techniques (e.g., NASBA) are found in Berger, Sambrook, and Ausubel, id., as well as in Mullis et al., (1987) U.S. Pat. No. 4,683,202; *PCR Protocols A Guide to Methods and Applications* (Innis et al. eds) Academic Press Inc. San Diego, Calif. (1990) (Innis); Arnheim & Levinson (Oct. 1, 1990) *C&EN* 3647; *The Journal Of NIH Research* (1991) 3, 81–94; Kwoh et al. (1989) *Proc. Natl. Acad. Sci. USA* 86, 1173; Guatelli et al. (1990) *Proc. Natl. Acad. Sci. USA* 87, 1874; Lomell et al. (1989) *J. Clin. Chem* 35, 1826; Landegren et al., (1988) *Science* 241, 1077–1080; Van Brunt (1990) *Biotechnology* 8, 291–294; Wu and Wallace, (1989) *Gene* 4, 560; Barringer et al. (1990) *Gene* 89, 117, and Sooknanan and Malek (1995) *Biotechnology* 13: 563–564. Improved methods of cloning in vitro amplified nucleic acids are described in Wallace et al., U.S. Pat. No. 5,426,039. Improved methods of amplifying large nucleic acids by PCR are summarized in Cheng et al. (1994) *Nature* 369: 684–685 and the references therein, in which PCR amplicons of up to 40 kb are generated. PCR reassembly techniques are discussed supra. One of skill will appreciate that essentially any RNA can be converted into a double stranded DNA suitable for restriction digestion, PCR expansion and sequencing using reverse transcriptase and a polymerase. See, Ausbel, Sambrook and Berger, all supra.

If gene synthesis is essentially error-free (stringent), and, e.g., performed in a parallel mode where each of the individual members of library was originally synthesized in spatially separated areas or containers (vessels), then deconvolution is performed by referencing the positional encoding index for each intended sequence of all library members. If the synthesis is performed in a poolwise fashion (or if library members were pooled during selection), then one of the many known polynucleotide sequencing techniques is used.

Recursive GAGGS Processes.

The recursive nature of directed evolution methods, aimed at stepwise/roundwise improvement of desired properties of polynucleotides and polypeptides, is well understood. In directed evolution (DE) by GAGGS, one or more deconvoluted character string(s), encoding sequences of those variants displaying certain changes in level of desired properties (where the level is arbitrarily defined by increase/decrease/ratios between measures of several properties), can be used to comprise a new library of character strings for a new round of GAGGS. Recursive GAGGS, unlike typical DNA shuffling, does not use physical manipulation of the polynucleotides in order to produce subsequent generations of gene diversity. Instead, GAGGS simply uses sequence information describing acquired beneficial changes as a foundation for generating additional changes leading to subsequent changes (improvements) in the desired properties of molecules encoded by the character strings. Recursive GAGGS can be performed until strings of characters are evolved to the point when the encoded polynucleotides and polypeptides attain arbitrarily set levels of desired characteristics or until further changes in characteristics cannot be obtained (e.g., enzyme turnover reached theoretical diffusion rate limit under conditions of a physical assay). Genetic algorithm parameters, gene synthesis methods and schemes, as well as physical assays and sequence deconvolution methods can vary in each of the different rounds/cycles of directed evolution by recursive GAGGS.).

One particular advantage of this approach is that an initially random or pseudo random approach to library generation can become progressively more directed as information on activity levels becomes available. For example, any heuristic learning approach or neural network approach gradually becomes more efficient at selecting "correct" (active) sequences. A variety of such approaches are set forth below, including principle component analysis, use of negative data, data parameterization and the like.

Integration of GAGGS, DNA Shuffling and other Directed Evolution Technologies.

GAGGS constitutes a self-sufficient and independent technology which can be practiced regardless of DNA shuffling or any other available directed evolution methods. However, one or more rounds of GAGGS can be, and often is, practiced in combination with physical shuffling of nucleic acids, and/or in combination with site directed mutagenesis, or error-prone PCR (e.g. as alternating cycles of a directed evolution process) or other diversity generation methods. GAGGS-generated libraries of polynucleotides can be subjected to nucleic acid shuffling, and polynucleotides found to have desired characteristics following rounds of in silico and/or physical shuffling can be selected and sequenced to provide character strings to evaluate GAGGS processes or to form character strings for further GAGGS operations. Thus, GAGGS can be performed as a stand-alone technology, or can be followed by shuffling, mutagenesis, random priming PCR, etc.

Where the methods of the invention entail performing physical recombination ("shuffling") and screening or selection to evolve individual genes, whole plasmids, viruses, multigene clusters, or even whole genomes, the techniques of the inventors and their co-workers are particularly useful. For example, reiterative cycles of recombination and screening/selection can be performed to further evolve the nucleic acids of interest which are generated by performing a GO on a character string (e.g., followed by synthesis of corresponding oligonucleotides, and gene generation/regeneration, e.g., by assembly PCR).

The following publications describe a variety of recursive recombination procedures and/or related diversity generation methods which can be practiced in conjunction with the in silico processes of the invention: Stemmer, et al., (1999) "Molecular breeding of viruses for targeting and other clinical properties. Tumor Targeting" 4:1–4; Ness et al. (1999) "DNA Shuffling of subgenomic sequences of subtilisin" *Nature Biotechnology* 17:893–896; Chang et al. (1999) "Evolution of a cytokine using DNA family shuffling" *Nature Biotechnology* 17:793–797; Minshull and Stemmer (1999) "Protein evolution by molecular breeding" *Current Opinion in Chemical Biology* 3:284–290; Christians et al. (1999) "Directed evolution of thymidine kinase for AZT phosphorylation using DNA family shuffling" *Nature Biotechnology* 17:259–264; Crameri et al. (1998) "DNA shuffling of a family of genes from diverse species accelerates directed evolution" *Nature* 391:288–291; Crameri et al. (1997) "Molecular evolution of an arsenate detoxification pathway by DNA shuffling," *Nature Biotechnology* 15:436–438; Zhang et al. (1997) "Directed evolution of an effective fucosidase from a galactosidase by DNA shuffling and screening" *Proceedings of the National Academy of Sciences, U.S.A.* 94:4504–4509; Patten et al. (1997) "Applications of DNA Shuffling to Pharmaceuticals and Vaccines" *Current Opinion in Biotechnology* 8:724–733; Crameri et al. (1996) "Construction and evolution of antibody-phage libraries by DNA shuffling" *Nature Medicine* 2:100–103; Crameri et al. (1996) "Improved green fluorescent protein by molecular evolution using DNA shuffling" *Nature Biotechnology* 14:315–319; Gates et al. (1996) "Affinity selective isolation of ligands from peptide libraries through display on a lac repressor 'headpiece dimer'"*Journal of Molecular Biology* 255:373–386; Stemmer (1996) "Sexual PCR and Assembly PCR" In: The Encyclopedia of Molecular Biology. VCH Publishers, New York. pp. 447–457; Crameri and Stemmer (1995) "Combinatorial multiple cassette mutagenesis creates all the permutations of mutant and wildtype cassettes" *BioTechniques* 18:194–195; Stemmer et al., (1995) "Single-step assembly of a gene and entire plasmid form large numbers of oligodeoxyribonucleotides" *Gene,* 164:49–53; Stemmer (1995) "The Evolution of Molecular Computation" *Science* 270: 1510; Stemmer (1995) "Searching Sequence Space" *Bio/Technology* 13:549–553; Stemmer (1994) "Rapid evolution of a protein in vitro by DNA shuffling" *Nature* 370:389–391; and Stemmer (1994) "DNA shuffling by random fragmentation and reassembly: In vitro recombination for molecular evolution." *Proceedings of the National Academy of Sciences, U.S.A.* 91:10747–10751.

Additional details regarding DNA shuffling methods are found in U.S. Patents by the inventors and their co-workers, including: U.S. Pat. No. 5,605,793 to Stemmer (Feb. 25, 1997), "METHODS FOR IN VITRO RECOMBINATION;" U.S. Pat. No. 5,811,238 to Stemmer et al. (Sep. 22, 1998) "METHODS FOR GENERATING POLYNUCLEOTIDES HAVING DESIRED CHARACTERISTICS BY ITERATIVE SELECTION AND RECOMBINATION;" U.S. Pat. No. 5,830,721 to Stemmer et al. (Nov. 3, 1998), "DNA MUTAGENESIS BY RANDOM FRAGMENTATION AND REASSEMBLY;" U.S. Pat. No. 5,834,252 to Stemmer, et al. (Nov. 10, 1998) "END-COMPLEMENTARY POLYMERASE REACTION," and U.S. Pat. No. 5,837,458 to Minshull, et al. (Nov. 17, 1998), "METHODS AND COMPOSITIONS FOR CELLULAR AND METABOLIC ENGINEERING."

In addition, details and formats for nucleic acid shuffling are found in a variety of PCT and foreign patent application publications, including: Stemmer and Crameri, "DNA MUTAGENESIS BY RANDOM FRAGMENTATION AND REASEMBLY" WO 95/22625; Stemmer and Lipschutz "END COMPLEMENTARY POLYMERASE CHAIN REACTION" WO 96/33207; Stemmer and Crameri "METHODS FOR GENERATING POLYNUCLEOTIDES HAVING DESIRED CHARACTERISTICS BY ITERATIVE SELECTION AND RECOMBINATION" WO 97/0078; Minshul and Stemmer, "METHODS AND COMPOSITIONS FOR CELLULAR AND METABOLIC ENGINEERING" WO 97/35966; Punnonen et al. "TARGETING OF GENETIC VACCINE VECTORS" WO 99/41402; Punnonen et al. "ANTIGEN LIBRARY IMMUNIZATION" WO 99/41383; Punnonen et al. "GENETIC VACCINE VECTOR ENGINEERING" WO 99/41369; Punnonen et al. OPTIMIZATION OF IMMUNOMODULATORY PROPERTIES OF GENETIC VACCINES WO 9941368; Stemmer and Crameri, "DNA MUTAGENESIS BY RANDOM FRAGMENTATION AND REASSEMBLY" EP 0934999; Stemmer "EVOLVING CELLULAR DNA UPTAKE BY RECURSIVE SEQUENCE RECOMBINATION" EP 0932670; Stemmer et al., "MODIFICATION OF VIRUS TROPISM AND HOST RANGE BY VIRAL GENOME SHUFFLING" WO 9923107; Apt et al., "HUMAN PAPILLOMAVIRUS VECTORS" WO 9921979; Del Cardayre et al. "EVOLUTION OF WHOLE CELLS AND ORGAN- ISMS BY RECURSIVE SEQUENCE RECOMBINATION" WO 9831837; Patten and Stemmer, "METHODS AND COMPOSITIONS FOR POLYPEPTIDE ENGINEERING" WO 9827230; Stemmer et al., and "METHODS FOR OPTIMIZATION OF GENE THERAPY BY RECURSIVE SEQUENCE SHUFFLING AND SELECTION" WO9813487.

Certain U.S. Applications provide additional details regarding DNA shuffling and related techniques, including "SHUFFLING OF CODON ALTERED GENES" by Patten et al. filed Sep. 29, 1998, (U.S. Ser. No. 60/102,362), Jan. 29, 1999 (U.S. Ser. No. 60/117,729), and Sep. 28, 1999, USSN PCT/US99/22588; "EVOLUTION OF WHOLE CELLS AND ORGANISMS BY RECURSIVE SEQUENCE RECOMBINATION", by del Cardyre et al. filed Jul. 15, 1999 (U.S. Ser. No. 09/354,922); "OLIGONUCLEOTIDE MEDIATED NUCLEIC ACID RECOMBINATION" by Crameri et al., filed Feb. 5, 1999 (U.S. Ser. No. 60/118,813) and filed Jun. 24, 1999 (U.S. Ser. No. 60/141,049) and filed Sep. 28, 1999 (U.S. Ser. No. 09/408,392), and "USE OF CODON-BASED OLIGONUCLEOTIDE SYNTHESIS FOR SYNTHETIC SHUFFLING" by Welch et al., filed Sep. 28, 1999 (U.S. Ser. No. 09/408,393).

As review of the foregoing publications, patents, published applications and U.S. patent applications reveals, shuffling (or "recursive recombination") of nucleic acids to provide new nucleic acids with desired properties can be carried out by a number of established methods. Any of these methods are integrated with those of the present invention by incorporating nucleic acids corresponding to character strings produced by performing one or more GO on one or more selected parental character string. Any of these methods can be adapted to the present invention to evolve GAGGS produced nucleic acids as discussed herein to produce new nucleic acids with improved properties. Both the methods of making such nucleic acids and the nucleic acids produced by these methods are a feature of the invention.

In brief, at least 5 different general classes of recombination methods can be performed (separately or in combination) in accordance with the present invention. First, nucleic acids such as those produced by synthesis of sets of nucleic acids corresponding to character strings produced by GO manipulation of character strings, or available homologues of such sets, or both, can be recombined in vitro by any of a variety of techniques discussed in the references above, including e.g., DNAse digestion of nucleic acids to be recombined followed by ligation and/or PCR reassembly of the nucleic acids. Second, sets of nucleic acids corresponding to character strings produced by GO manipulation of character strings, and/or available homologues of such sets, can be recursively recombined in vivo, e.g., by allowing recombination to occur between the nucleic acids while in cells. Third, whole cell genome recombination methods can be used in which whole genomes of cells are recombined, optionally including spiking of the genomic recombination mixtures with desired library components such as with sets of nucleic acids corresponding to character strings produced by GO manipulation of character strings, or available homologues of such sets. Fourth, synthetic recombination methods can be used, in which oligonucleotides corresponding to different homologues are synthesized and reassembled in PCR or ligation reactions which include oligonucleotides which correspond to more than one parental nucleic acid, thereby generating new recombined nucleic acids. Oligonucleotides can be made by standard nucleotide addition methods, or can be made by tri-nucleotide synthetic approaches. Fifth, purely in silico methods of recombination can be effected in which GOs are used in a computer to recombine sequence strings which correspond to nucleic acid or proteins homologues. The resulting recombined sequence strings are optionally converted into nucleic acids by synthesis of nucleic acids which correspond to the recombined sequences, e.g., in concert with oligonucleotide synthesis/gene reassembly techniques. Any of the preceding general recombination formats, separately or together, can be practiced in a reiterative fashion to generate a diverse set of recombinant nucleic acids.

The above references in conjunction with the present disclosure provide these and other basic recombination formats as well as many modifications of these formats. Regardless of the format which is used, the nucleic acids of the invention can be recombined (with each other or with related (or even unrelated) nucleic acids to produce a diverse set of recombinant nucleic acids, including homologous nucleic acids.

Other diversity generating approaches can also be used to modify character strings or nucleic acids. Additional diversity can be introduced into input or output nucleic acids by methods which result in the alteration of individual nucleotides or groups of contiguous or non-contiguous nucleotides, i.e., mutagenesis methods. Mutagenesis methods include, for example, recombination (PCT/US98/05223; Publ. No. WO98/42727); oligonucleotide-directed mutagenesis (for review see, Smith, *Ann. Rev. Genet.* 19: 423–462 (1985); Botstein and Shortle, *Science* 229: 1193–1201 (1985); Carter, *Biochem. J.* 237: 1–7 (1986); Kunkel, "The efficiency of oligonucleotide directed mutagenesis" in *Nucleic acids &Molecular Biology*, Eckstein and Lilley, eds., Springer Verlag, Berlin (1987)). Included among these methods are oligonucleotide-directed mutagenesis (Zoller and Smith, *Nucl. Acids Res.* 10: 6487–6500 (1982), *Methods in Enzymol.* 100: 468–500 (1983), and Methods in Enzymol. 154: 329–350 (1987)) phosphothioate-modified DNA mutagenesis (Taylor et al., *Nucl. Acids Res.* 13: 8749–8764 (1985); Taylor et al., *Nucl. Acids Res.* 13: 8765–8787 (1985); Nakamaye and Eckstein, *Nucl. Acids Res.* 14: 9679–9698 (1986); Sayers et al., *Nucl. Acids Res.* 16:791–802 (1988); Sayers et al., *Nucl. Acids Res.* 16: 803–814 (1988)), mutagenesis using uracil-containing templates (Kunkel, *Proc. Nat'l. Acad. Sci. USA* 82: 488–492 (1985) and Kunkel et al., *Methods in Enzymol.* 154:367–382)); mutagenesis using gapped duplex DNA (Kramer et al., *Nucl. Acids Res.* 12: 9441–9456 (1984); Kramer and Fritz, *Methods in Enzymol.* 154:350–367 (1987); Kramer et al., *Nucl. Acids Res.* 16: 7207 (1988)); and Fritz et al., *Nucl. Acids Res.* 16: 6987–6999 (1988)). Additional suitable methods include point mismatch repair (Kramer et al., *Cell* 38: 879–887 (1984)), mutagenesis using repair-deficient host strains (Carter et al., *Nucl. Acids Res.* 13: 4431–4443 (1985); Carter, *Methods in Enzymol.* 154: 382–403 (1987)), deletion mutagenesis (Eghtedarzadeh and Henikoff, *Nucl. Acids Res.* 14: 5115 (1986)), restriction-selection and restriction-purification (Wells et al., *Phil. Trans. R. Soc. Lond. A* 317: 415–423 (1986)), mutagenesis by total gene synthesis (Nambiar et al., *Science* 223: 1299–1301 (1984); Sakamar and Khorana, *Nucl. Acids Res.* 14: 6361–6372 (1988); Wells et al., *Gene* 34:315–323 (1985); and Grundström et al., *Nucl. Acids Res.* 13: 3305–3316 (1985). Kits for mutagenesis are commercially available (e.g., Bio-Rad, Amersham International, Anglian Biotechnology).

Other diversity generation procedures are proposed in U.S. Pat. No. 5,756,316; U.S. Pat. No. 5,965,408; Ostermeier et al. (1999) "A combinatorial approach to hybrid enzymes independent of DNA homology" Nature Biotech 17:1205; U.S. Pat. No. 5,783,431; U.S. Pat. No. 5,824,485; U.S. Pat. No. 5,958,672; Jirholt et al. (1998) "Exploiting sequence space: shuffling in vivo formed complementarity determining regions into a master framework" Gene 215: 471; U.S. Pat. No. 5,939,250; WO 99/10539; WO 98/58085; WO 99/10539 and others. These diversity generating methods can be combined with each other or with shuffling reactions or in silico operations, in any combination selected by the user, to produce nucleic acid diversity, which may be screened for using any available screening method.

Following recombination or other diversification reactions, any nucleic acids which are produced can be selected for a desired activity. In the context of the present invention, this can include testing for and identifying any detectable or assayable activity, by any relevant assay in the art. A variety of related (or even unrelated) properties can be assayed for, using any available assay.

Accordingly, a recombinant nucleic acid produced by recursively recombining one or more polynucleotide of the invention (produced by GAGGS methods) with one or more additional nucleic acid forms a part of the invention. The one or more additional nucleic acid may include another polynucleotide of the invention; optionally, alternatively, or in addition, the one or more additional nucleic acid can include, e.g., a nucleic acid encoding a naturally-occurring sequence or a subsequence, or any homologous sequence or subsequence.

The recombining steps can be performed in vivo, in vitro, or in silico as described in more detail in the references above and herein. Also included in the invention is a cell containing any resulting recombinant nucleic acid, nucleic acid libraries produced by recursive recombination of the nucleic acids set forth herein, and populations of cells, vectors, viruses, plasmids or the like comprising the library or comprising any recombinant nucleic acid resulting from recombination (or recursive recombination) of a nucleic acid as set forth herein with another such nucleic acid, or an additional nucleic acid. Corresponding sequence strings in a database present in a computer system or computer readable medium are a feature of the invention.

By way of example, a typical physical recombination procedure starts with at least two substrates that generally show at least some identity to each other (i.e., at least about 30%, 50%, 70%, 80% or 90% or more sequence identity), but differ from each other at certain positions (however, in purely in silico or cross-over oligonucleotide mediated formats, nucleic acids can show little or no homology). For example, two or more nucleic acids can be recombined herein. The differences between the nucleic acids can be any type of mutation, for example, substitutions, insertions and deletions. Often, different segments differ from each other in about 1–20 positions. For recombination to generate increased diversity relative to the starting materials, the starting materials differ from each other in at least two nucleotide positions. That is, if there are only two substrates, there should be at least two divergent positions. If there are three substrates, for example, one substrate can differ from the second at a single position, and the second can differ from the third at a different single position. Of course, even if only one initial character string is provided, any GO herein can be used to modify the nucleic acid to produce a diverse array of nucleic acids that can be screened for an activity of interest.

In physical shuffling procedures, starting DNA segments can be natural variants of each other, for example, allelic or species variants. More typically, they are derived from one or more homologous nucleic acid sequence. The segments can also be from nonallelic genes showing some degree of structural and usually functional relatedness. The starting DNA segments can also be induced variants of each other. For example, one DNA segment can be produced by error-prone PCR replication of the other, or by substitution of a mutagenic cassette. Induced mutants can also be prepared by propagating one (or both) of the segments in a mutagenic strain. In these situations, strictly speaking, the second DNA segment is not a single segment but a large family of related segments. The different segments forming the starting materials are often the same length or substantially the same length. However, this need not be the case; for example, one segment can be a subsequence of another. The segments can be present as part of larger molecules, such as vectors, or can be in isolated form. In one option, the nucleic acids of interest are derived from DE by GAGGS.

Codon-Varied Oligonucleotide Methods

Codon-varied oligonucleotides are oligonucleotides, similar in sequence but with one or more base variations, where the variations correspond to at least one encoded amino acid difference. They can be synthesized utilizing tri-nucleotide, i.e., codon-based phosphoramidite coupling chemistry, in which tri-nucleotide phosphoramidites representing codons for all 20 amino acids are used to introduce entire codons into oligonucleotide sequences synthesized by this solid-phase technique. Preferably, all of the oligonucleotides of a selected length (e.g., about 20, 30, 40, 50, 60, 70, 80, 90, or 100 or more nucleotides) which incorporate the chosen nucleic acid sequences are synthesized. In the present invention, codon-varied oligonucleotide sequences can be based upon sequences from a selected set of nucleic acids, generated by any of the approaches noted herein. Further details regarding tri-nucleotide synthesis are found in U.S. Ser. No. 09/408,393 "USE OF CODON VARIED OLIGONUCLEOTIDE SYNTHESIS FOR SYNTHETIC SHUFFLING" by Welch, et al., filed Sep. 28, 1999.

Oligonucleotides can be made by standard nucleotide addition methods, or can be made by tri-nucleotide synthetic approaches. An advantage of selecting changes which correspond to encoded amino acid differences is that the modification of triplets of codons results in fewer frameshifts (and, therefore, likely fewer inactive library members). Also, synthesis which focuses on codon modification, rather than simply on base variation, reduces the total number of oligos which are needed for a synthesis protocol.

Oligo Sets

In general, sets of oligos can be combined for assembly in many different formats and different combinations schemes to effect correlation with genetic events and operators at the physical level.

As noted, overlapping sets of oligonucleotides can be synthesized and then hybridized and elongated to form full-length nucleic acids. A full length nucleic acid is any nucleic acid desired by an investigator which is longer than the oligos which are used in the gene reconstruction methods. This can correspond to any percentage of a naturally occurring full length sequence, e.g., 10%, 20%, 30%, 40%, 50%, 60%, 70%, 80%, or 90% or more of the corresponding natural sequence.

Oligo sets often have at least about 5, sometimes about 10, often about 15, generally about 20, or more, nucleotide overlap sequences to facilitate gene reconstruction. Oligo sets are optionally simplified for gene reconstruction purposes where regions of fortuitous overlap are present, i.e., where repetitive sequence elements are present or designed into a gene sequence to be synthesized. Lengths of oligos in a set can be the same or different, as can the regions of sequence overlap. To facilitate hybridization and elongation (e.g., during cycles of PCR), overlap regions are optionally designed with similar melting temperatures.

Parental sequences can be gridded (conceptually or physically) and the common sequences used to select common sequence oligos, thereby combining oligo members into one or more sets to reduce the number of oligos required for making full-length nucleic acids. Similarly, oligonucleotides with some sequence similarity can be generated by pooled and/or split synthesis where pools of oligos under synthesis are split into different pools during the addition of heterologous bases, optionally followed by rejoined synthesis steps (pooling) at subsequent stages where the same additions to the oligos are required. In Oligo shuffling formats, heterologous oligos corresponding to many different parents can be split and rejoined during synthesis. In simple degenerate synthetic approaches, more than one nucleobase can be added during single synthetic steps to produce two or more variations in sequence in two or more resulting oligonucleotides. The relative percentage of nucleobase addition can be controlled to bias synthesis towards one or more parental sequence. Similarly, partial generacy can be practiced to prevent the insertion of stop codons during degenerated oligonucleotide synthesis.

Oligos which correspond to similar subsequences from different parents can be the same length or different, depending on the subsequences. Thus, in split and pooled formats, some oligos are optionally not elongated during every synthetic step (to avoid frame-shifting, some be oligos are not elongated for the steps corresponding to one or more codon).

When constructing oligos, crossover oligos can be constructed at one or more point of difference between two or more parental sequences (a base change or other difference is a genetic locus which can be treated as a point for a crossover event). The crossover oligos have a region of sequence identity to a first parental sequence, followed by a region of identity to a second parental sequence, with crossover point occurring at the locus. For example, every natural mutation can be a cross over point.

Another way of biasing sequence recombination is to spike a mixture of oligonucleotides with fragments of one or more parental nucleic acid (if more than one parental nucleic acid is fragmented, the resulting segments can be spiked into a recombination mixture at different frequencies to bias recombination outcomes towards one or more parent). Recombination events can also be engineered simply by omitting one or more oligonucleotide corresponding to one or more parent from a recombination mixture.

In addition to the use of families of related oligonucleotides, diversity can be modulated by the addition of selected, pseudo-random or random oligos to elongation mixture, which can be used to bias the resulting full-length sequences. Similarly, mutagenic or non-mutagenic conditions can be selected for PCR elongation, resulting in more or less diverse libraries of full length nucleic acids.

In addition to mixing oligo sets which correspond to different parents in the elongation mixture, oligo sets which correspond to just one parent can be elongated to reconstruct that parent. In either case, any resulting full-length sequence can be fragmented and recombined, as in the DNA shuffling methods noted in the references cited herein.

Many other oligonucleotide sets and synthetic variations which can be correlated to genetic events and operators at the physical level are found in "OLIGONUCLEOTIDE MEDIATED NUCLEIC ACID RECOMBINATION" by Crameri et al., filed Feb. 5, 1999 (U.S. Ser. No. 60/118,813) and filed Jun. 24, 1999 (U.S. Ser. No. 60/141,049) and filed Sep. 28, 1999 (U.S. Ser. No. 09/408,392) and "USE OF CODON-BASED OLIGONUCLEOTIDE SYNTHESIS FOR SYNTHETIC SHUFFLING" by Welch et al., filed Sep. 28, 1999 (U.S. Ser. No. 09/408,393).

Targets for Codon Modification and Shuffling

Essentially any nucleic acid can be shuffled using the GAGGS methods herein. No attempt is made herein to identify the hundreds of thousands of known nucleic acids. Common sequence repositories for known proteins include GenBank EMBL, DDBJ and the NCBI. Other repositories can easily be identified by searching the internet.

One class of preferred targets for GAGGS methods includes nucleic acids encoding therapeutic proteins such as erythropoietin (EPO), insulin, peptide hormones such as human growth hormone; growth factors and cytokines such as epithelial Neutrophil Activating Peptide-78, GROα/MGSA, GROP, GROβ, MIP-1a, MIP-1δ, MCP-1, epidermal growth factor, fibroblast growth factor, hepatocyte growth factor, insulin-like growth factor, the interferons, the interleukins, keratinocyte growth factor, leukemia inhibitory factor, oncostatin M, PD-ECSF, PDGF, pleiotropin, SCF, c-kit ligand, VEGEF, G-CSF etc. Many of these proteins and their corresponding coding nucleic acids are commercially available (See, e.g., the Sigma BioSciences 1997 catalogue and price list), and, in any case, the corresponding genes are well-known.

Another class of preferred targets for GAGGS are transcription and expression activators. Example transcriptional and expression activators include genes and proteins that modulate cell growth, differentiation, regulation, or the like. Expression and transcriptional activators are found in prokaryotes, viruses, and eukaryotes, including fungi, plants, and animals, including mammals, providing a wide range of therapeutic targets. It will be appreciated that expression and transcriptional activators regulate transcription by many mechanisms, e.g., by binding to receptors, stimulating a signal transduction cascade, regulating expression of transcription factors, binding to promoters and enhancers, binding to proteins that bind to promoters and enhancers, unwinding DNA, splicing pre-mRNA, polyadenylating RNA, and degrading RNA. Expression activators include cytokines, inflammatory molecules, growth factors, their receptors, and oncogene products, e.g., interleukins (e.g., IL-1, IL-2, IL-8, etc.), interferons, FGF, IGF-I, IGF-II, FGF, PDGF, TNF, TGF-α, TGF-β, EGF, KGF, SCF/c-Kit, CD40UCD40, VLA-4/VCAM-1, ICAM-1/LFA-1, and hyalurin/CD44; signal transduction molecules and corresponding oncogene products, e.g., Mos, Ras, Raf, and Met; and transcriptional activators and suppressors, e.g., p53, Tat, Fos, Myc, Jun, Myb, Rel, and steroid hormone receptors such as those for estrogen, progesterone, testosterone, aldosterone, the LDL receptor ligand and corticosterone.

Similarly, proteins from infectious organisms for possible vaccine applications, described in more detail below, including infectious fungi, e.g., *Aspergillus, Candida* species; bacteria, particularly *E. coli*, which serves a model for pathogenic bacteria, as well as medically important bacteria such as Staphylococci (e.g., *aureus*), Streptococci (e.g., *pneumoniae*), Clostridia (e.g., *perfringens*), Neisseria (e.g., *gonorrhoea*), Enterobacteriaceae (e.g., coli), *Helicobacter* (e.g., *pylori*), *Vibrio* (e.g., *cholerae*), *Capylobacter* (e.g., *jejuni*), *Pseudomonas* (e.g., *aeruginosa*), *Hemeophilus* (e.g., influenzae), Bordetella (e.g., pertussis), Mycoplasma (e.g., pneumoniae), Ureaplasma (e.g., urealyticum), Legionella (e.g., pneumophila), Spirochetes (e.g., Treponema, Leptospira, and Borrelia), Mycobacteria (e.g., tuberculosis, smegmatis), Actinomyces (e.g., israelii), Nocardia (e.g., asteroides), Chlamydia (e.g., trachomatis), Rickettsia, Coxiella, Ehrilichia, Rochalimaea, Brucella, Yersinia, Fracisella, and Pasteurella; protozoa such as sporozoa (e.g., Plasmodia), rhizopods (e.g., Entamoeba) and flagellates (Trypanosoma, Leishmania, Trichomonas, Giardia, etc.); viruses such as (+) RNA viruses (examples include Poxviruses e.g., vaccinia; Picornaviruses, e.g. polio; Togaviruses, e.g., rubella; Flaviviruses, e.g., HCV; and Coronaviruses), (−) RNA viruses (examples include Rhabdoviruses, e.g., VSV; Paramyxovimses, e.g., RSV; Orthomyxovimses, e.g., influenza; Bunyaviruses; and Arenaviruses), dsDNA viruses (Reoviruses, for example), RNA to DNA viruses, i.e., Retroviruses, e.g., especially HIV and HTLV, and certain DNA to RNA viruses such as Hepatitis B virus.

Other nucleic acids encoding proteins relevant to non-medical uses, such as inhibitors of transcription or toxins of crop pests e.g., insects, fungi, weed plants, and the like, are also preferred targets for GAGGS. Industrially important enzymes such as monooxygenases, proteases, nucleases, and lipases are also preferred targets. As an example, subtilisin can be evolved by shuffling selected forms of the gene for subtilisin (von der Osten et al., *J. Biotechnol.* 28:55–68 (1993) provide a subtilisin coding nucleic acid). Proteins which aid in folding such as the chaperonins are also preferred.

Preferred known genes suitable for codon alteration and shuffling also include the following: Alpha-i antitrypsin, Angiostatin, Antihemolytic factor, Apolipoprotein, Apoprotein, Atrial natriuretic factor, Atrial natriuretic polypeptide, Atrial peptides, C—X—C chemokines (e.g., T39765, NAP-2, ENA-78, Gro-a, Gro-b, Gro-c, IP-10, GCP-2, NAP-4, SDF-1, PF4, MIG), Calcitonin, CC chemokines (e.g., Monocyte chemoattractant protein-1, Monocyte chemoattractant protein-2, Monocyte chemoattractant protein-3, Monocyte inflammatory protein-1 alpha, Monocyte inflammatory protein-1beta, RANTES, 1309, R83915, R91733, HCC1, T58847, D31065, T64262), CD40 ligand, Collagen, Colony stimulating factor (CSF), Complement factor Sa, Complement inhibitor, Complement receptor 1, Factor IX, Factor VII, Factor VIII, Factor X, Fibrinogen, Fibronectin, Glucocerebrosidase, Gonadotropin, Hedgehog proteins (e.g., Sonic, Indian, Desert), Hemoglobin (for blood substitute; for radiosensitization), Hirudin, Human serum albumin, Lactoferrin, Luciferase, Neurturin, Neutrophil inhibitory factor (NIF), Osteogenic protein, Parathyroid hormone, Protein A, Protein G, Relaxin, Renin, Salmon calcitonin, Salmon growth hormone, Soluble complement receptor I, Soluble I-CAM 1, Soluble interleukin receptors (IL-1, 2, 3, 4, 5, 6, 7, 9, 10, 11, 12, 13, 14, 15), Soluble TNF receptor, Somatomedin, Somatostatin, Somatotropin, Streptokinase, Superantigens, i.e., Staphylococcal enterotoxins (SEA, SEB, SEC1, SEC2, SEC3, SED, SEE), Toxic shock syndrome toxin (TSST-1), Exfoliating toxins A and B, Pyrogenic exotoxins A, B, and C, and M. arthritides mitogen, Superoxide dismutase, Thymosin alpha 1, Tissue plasminogen activator, Tumor necrosis factor beta (TNF beta), Tumor necrosis factor receptor (TNFR), Tumor necrosis factor-alpha (TNF alpha) and Urokinase.

Other preferred genes for shuffling include p450s (these enzymes represent a very diverse set of natural diversity and catalyze many important reactions); see, e.g., Ortiz de Montellano (ed.) (1995) *Cytochrome P450 Structure Mechanism and Biochemistry, Second Edition* Plenum Press (New York and London) and the references cited therein for an introduction to cytochrome P450. Other monooxygenases, as well as dioxygenases, acyl transferases (cis-diol), halogenated hydrocarbon dehalogenases, methyl transferases, terpene synthetases, and the like, can be shuffled.

The Uses of Consensus Genes in Directed Evolution, Including "Diplomacy"

One of the factors involved in standard family shuffling of parental genes is the extent of identity of the genes to be physically recombined. Genes of limited identity are difficult to recombine without cross-over oligonucleotides, and often result in shuffled libraries having unacceptable knock-out rates, or no chimera formation, no activity, no functional library, etc. In one aspect, the present invention overcomes this difficulty by providing for in silico design of a "diplomat" sequence which has an intermediate level of homology to each of the sequences to be recombined, thereby facilitating cross-over events between the sequences and facilitating chimera formation. This diplomat sequence can be a character string produced by any of a variety of GO to establish intermediate sequence similarity in the diplomat sequence as compared to the sequences to be recombined, including by alignment of the sequences to select a consensus sequence, codon modification to optimize similarity between diverse nucleic acids, or the like.

As noted, one way in which to design a diplomat sequence is simply to select a consensus sequence, e.g., using any of the approaches herein. The consensus sequence is generated by comparison and lining-up/pile-up of a family of genes ([DNA consensus), or of amino acid sequence line-up/pile-up (aa consensus). In the latter case, the amino acid consensus sequence are optionally back-translated using a desirable codon bias to further enhance homology, or to enhance host organism for expression, or to select for alternate codon usages in order to enable access to alternative sets of amino acid codons. One can also use different subsets of gene families to generate consensus sequences.

Furthermore, the consensus sequence itself may encode an improved enzyme. This has been observed elsewhere (e.g. presentation at International Conference "Enzyme Opportunities on the Next Millenium", Chicago, Ill., May 5–7, by Dr. Luis Pasamontes, Roche Vitamins, Inc., on "Development of Heat Stable Phytase"—a consensus phytase had an increase of 16 degrees C. in thermostability). Another example of a consensus protein having improved properties is consensus Interferon (IEFN-con1).

An additional approach is to design consensus sequences to control (minimize, maximize, direct, etc.) construction of cross-over oligonucleotides, e.g., as discussed supra.

Accordingly, separately or in conjunction with any of the techniques herein, diplomat sequences can be designed using selected GO criteria and, optionally, physically synthesized and shuffled using any of the techniques herein.

Example Processing Steps for Reverse Translation and Oligo Design

Automatic processing steps (e.g., performed in a digital system as described herein) that perform the following functions facilitate selection of oligonucleotides in synthetic shuffling techniques herein.

For example, the system can include an instruction set which permits inputting of amino acid sequences of a family of proteins of interest of interest.

These sequences are back-translated with any desired codon usage parameters, e.g., optimal usage parameters for one or more organism to be used for expression, or to optimize sequence alignments to facilitate recombination, or both. For example, codon usage can be selected for multiple expression hosts, e.g. *E. coli* and *S. cerevisiae*. In some cases, simply optimizing codon usage for expression in a host cell will result in making homologous sequences more similar, as they will lose their natural species codon bias.

Sequences are aligned, and a consensus sequence is produced, optionally showing degenerate codons.

Oligonucleotides are designed for synthetic construction of one or more corresponding synthetic nucleic acid for shuffling. Input parameters on oligonucleotide design include minimum and maximum lengths, minimum length of identical sequence at the ends, maximum degeneracy per oligonucleotide, length of oligo overlap, etc.

As noted, an alternative to back-translation to achieve optimal codon usage for expression in a particular organism is to back-translate sequences to optimize nucleotide homology between family members. For example, amino acid sequences are aligned. All possible codons for each amino acid are determined and codons that minimize differences between the family of aligned sequences are chosen at each position.

Use of Family Shuffling to Identify Structural Motifs Conferring Specific Protein Properties It is often of interest to identify regions of a protein that are responsible for specific properties, to facilitate functional manipulation and design of related proteins. This identification is traditionally done using structural information, usually obtained by biophysical techniques such as X-ray crystallography. The present invention provides an alternative method in which variants are obtained and analyzed for specific properties which are then correlated with sequence motifs.

The sequences of naturally occurring enzymes that catalyze similar or even identical reactions can vary widely: sequences may be only 50% identical or less. While a family of such enzymes can each catalyze an essentially identical reaction, other properties of these enzymes may differ significantly. These include physical properties such as stability to temperature and organic solvents, pH optima, solubility, the ability to retain activity when immobilized, ease of expression in different host systems, etc. They also include catalytic properties including activity ($k_{cat}$ and $K_m$), the range of substrates accepted and even the chemistries performed.

The method described here can also be applied to non-catalytic proteins (i.e. ligands such as cytokines) and even nucleic acid sequences (such as promoters that may be inducible by a number of different ligands), wherever multiple functional dimensions are encoded by a family of homologous sequences.

Because of the divergence between enzymes with similar catalytic functions, it is not usually possible to correlate specific properties with individual amino acids at certain positions, as there are simply too many amino acid differences. However, libraries of variants can be prepared from a family of homologous natural sequences by DNA family shuffling. These libraries contain the diversity of the original set of sequences, in a large number of different combinations. If individuals from the library are then tested under a specific set of conditions for a particular property, the optimal combinations of sequences from the parental set for those conditions can be determined.

If the assay conditions are then altered in only one parameter, different individuals from the library will be identified as the best performers. Because the screening conditions are very similar, most amino acids are conserved between the two sets of best performers. Comparisons of the sequences (e.g., in silico) of the best enzymes under the two different conditions identifies the sequence differences responsible for the differences in performance. Principal component analysis is a powerful tool to use for identifying sequences conferring a particular property. For example, Partek Incorporated (St. Peters, Mo.; partek.com, on the world wide web) provides software for pattern recognition (e.g., which provide Partek Pro 2000 Pattern Recognition Software) which can be applied to genetic algorithms for multivariate data analysis, interactive visualization, variable selection, neural & statistical modeling. Relationships can be analyzed, e.g., by Principal Components Analysis (PCA) mapped scatterplots and biplots, Multi-Dimensional Scaling (MDS) mapped scatterplots, Star plots, etc.

Once sequence motifs have been identified, proteins are manipulated in, e.g., any of a number of ways. For example, identified changes are optionally deliberately introduced into other sequence backrounds. Sequences conferring different specific properties can be combined. Identified sequence regions of importance for a specific function can be targeted for more thorough investigation, for example by complete randomization using degenerate oligonucleotides, e.g., selected by in silico processes.

Identification of Parental Contributors to Chimeras Produced by Family Shuffling This example provides a method for the identification of parental contributors to chimeras produced by family shuffling.

The method takes as an input the sequences of parental genes, and the sequences of chimeras, and compares each chimera with each parent. It then builds sequence and graphical maps of each chimera, indicating the parental source of each chimeric fragment. Correlation of this with functional data permits identification of parents that contribute to specific properties and thereby facilitates the selection of parents for new more focused libraries which can be made by any of the methods noted herein, and screened for any desired functional property.

In one simple example, family 3 and 4 genes contribute to an activity at, e.g., pH 5.5, while family 1 and 2 genes are better at pH 10. Thus, for an application at low pH, the parental composition to create a library would be biased towards 3 and 4, while for high pH a predominantly 1 and 2-based library would be appropriate. Thus, a GO can be implemented which selects oligonucleotides for gene reconstruction predominantly from families 3 and 4. Additional details regarding gene blending methods utilized in oligonucleotide shuffling are found in "OLIGONUCLEOTIDE MEDIATED NUCLEIC ACID RECOMBINATION" by Crameri et al., filed Feb. 5, 1999 (U.S. Ser. No. 60/118,813) and filed Jun. 24, 1999 (U.S. Ser. No. 60/141,049) and filed Sep. 28, 1999 (U.S. Ser. No. 09/408,392).

Gene blending is similar to principal component analysis (PCA) for identification of specific sequence motifs. Principal component analysis (PCA) is a mathematical procedure that transforms a number of (possibly) correlated variables into a (smaller) number of uncorrelated variables called "principal components." The first principal component accounts for as much of the variability in the data as possible, and each succeeding component accounts for as much of the remaining variability as possible. Traditionally, principal component analysis is performed on a square symmetric SSCP (pure sums of squares and cross products) matrix, covariance (scaled sums of squares and cross products) matrix, or correlation (sums of squares and cross products from standardized data) matrix. The analysis results for objects of type SSCP and covariance are similar. A correlation object is used when the variances of individual variates differ substantially or the units of measurement of the individual variates differ. Objectives of principal component analysis include, e.g., to discover or to reduce the dimensionality of a data set, to identify new meaningful underlying variables, and the like.

The main difference is that the present operation gives information about which parents to use in a mix (and so directs construction of new natural gene-based libraries), while PCA identifies specific motifs and so is well suited for more general synthetic shuffling, with identified discrete regions being altered in either a directed or randomized way.

Partek (PCA) software discussed above has an "experimental design" component, that identifies variables that appear to have an effect on a specific function. As applied to the present example, this is useful in an iterative process in which a family library is constructed and screened and the resulting chimeras analyzed for functional correlations with sequence variations. This is used to predict sequence regions for a particular function, and a library is selected in silico by any desired GO directed changes of the region which correlates to functional activity. A focused library which has diversity in those regions is constructed, e.g., by oligonucleotide synthetic methods as described herein. The resulting library members (chimeras) are analyzed for functional correlations with sequence variations. This approach focuses the search of variation in sequence space on the most relevant regions of a protein or other relevant molecule.

After sequences which are active are deconvoluted, the resulting sequence information is used to refine further predictions for in silico operations, e.g., in a neural net training approach.

For example, neural net approaches can be coupled to genetic algorithm-type programming for example, NNUGA (Neural Network Using Genetic Algorithms) is an available program (cs.bgu.ac.il/~omri/NNUGA/, on the world wide web) which couples neural networks and genetic algorithms. An introduction to neural networks can be found, e.g., in Kevin Gurney (1999) *An Introduction to Neural Networks*, UCL Press, 1 Gunpowder Square, London EC4A 3DE, UK. and at shef.ac.uk/psychology/gurney/notes/index.html (on the world wide web) additional useful neural network references include those noted above in regard to genetic algorithms and, e.g., Christopher M. Bishop (1995) *Neural Networks for Pattern Recognition* Oxford Univ Press; ISBN: 0198538642; Brian D. Ripley, N. L. Hjort (Contributor) (1995) *Pattern Recognition and Neural Networks* Cambridge Univ Pr (Short); ISBN: 0521460867.

In Silico Shuffling Incorporating Rational and/or Statistical Methods

One aspect of the present invention is the coupling of logical filtering mechanisms to nucleic acid or polypeptide sequences in silico and, e.g., random physical shuffling of logically "filtered" nucleic acids or polypeptides. As discussed throughout, in silico approaches can be used to apply any desired criteria to selection of recombination events, which are optionally coupled to physical shuffling processes to generate selected, random or pseudo-random recombined physical sequences for subsequent activity selection. Three basic logical GO filters are discussed herein in detail, though others will be apparent to one of skill.

First, structural considerations can be used to design logical filters which preserve or eliminate any structural feature of interest in a nucleic acid or encoded protein (as discussed herein, direct design and synthesis of recombinant proteins without nucleic acid intermediates can be performed, but, for simplicity of illustration, the following discussion generally describes the use of nucleic acids to generate proteins). Such structural criteria include e.g., energy minimization calculations, combinatorial automated protein design algorithms, sequence motifs, application of GAs or GOs to structural and/or sequence criteria, and, e.g., structural information based upon any available structural or modeling data. For example, structural data is provided, e.g., as derived from physical protein (or nucleic acid) analysis (e.g., crystal structure, nmr, epr, circular dichrosim, intrinsic fluorescence, mass spectrometry, and any of the myriad other available structural analysis methods) or by any structural modeling method. It will also be appreciated that modeling and physical structure information are optionally used in conjunction and that cycles of physical information analysis, modeling and application of this information in one or more GO in silico can be performed in conjunction. Indeed, certain combinatorial protein design algorithms themselves rely on cycles of experimentation and design (such approaches are discussed in more detail below).

Structural considerations can include, e.g., a logical filter (e.g., as part of any GO) which maintains or disrupts any interaction of two or more amino acids in a protein sequence. Where the filter is set to maintain structural features, the two or more amino acids will be selected to maintain their physical relationship and will, therefore, show co-variance in subsequent recombinants. That is, crossovers or other GOs are selected by the filter such that the physical-structural relationship of the two or more amino acids is linked or maintained (or disrupted, if desired). Generally, physical linkages can include any sort of structural element maintenance or disruption, including maintaining or disrupting physical distance relationships, energy minimization relationships, etc. It is, of course, useful to maintain or disrupt particular structures to derive similar or fundamentally different nucleic acids or proteins from a set of parental nucleic acids or proteins.

Another aspect that is related to function is the constraint to fold. Several experimental studies have focused on understanding intermediates in the folding pathway (e.g., Bai et.al, *Science* 1995 269:192–197). Thus, not only the structural considerations of the final native structure can be used to provide logical filters, but also intermediates during the folding pathway can be used for this purpose. This information can be used to make sure that any residue that may be important for the folding pathway can be retained.

Second, statistical considerations can be applied to provide any of a variety of filters for identifying relationships between nucleic acid or protein sequences. Many approaches are set forth herein, e.g., which determine which nucleic acids or amino acids are useful for activity criteria, e.g., based upon consideration of evolutionary algorithms that examine evolutionary relationships; for example, sequence conservation, homoplasy (independent convergent evolution that retains similarity between sequences), as well as learning algorithms that examine the effects of sequence alterations over one or more design cycles, Markov modeling, principle component analysis and the like can be used. For example, independent convergent evolution that retains similarity between sequences is called homoplasy. Statistical methods can identify homoplasic sites in a protein which can extend understanding of the protein structure by separating residues that are evolving to retain parent property. (See, e.g., Meyer. A *Novartis Found Symp* 1999, 222:141–153).

Third, combinations of structural and statistical approaches can be used. These can either constitute separate filters, or can be applied in a single complex logical filter. That is, it will be appreciated that many statistical observations are, ultimately, derived from structural relationships. Thus, algorithms that take account of both structural information and empirical statistical observations can be used as logical filters. Here again, complex cycles of protein structural analysis, modeling, GO application to design sequences in silico, recombinant nucleic acid/protein generation, screening and statistical analysis can be performed recursively, with each step in the process providing information that is useful in subsequent steps. For example, statistical analysis of empirical results can suggest that certain structural events or features are relevant, and can be used to refine modeling prediction and to elucidate structural analysis, and this information can be applied to the next cycle of GO application in silico to select additional crossover points or to apply any other GO of interest.

Several of the preceding and following sections give details on these various filtering approaches for the coupling of rational or semi-rational design criteria to random or semi-random recombination methods.

Coupling of Rational Protein Design and Shuffling

As noted, one aspect of the present invention is the use of any form of structural information in applying a logical filter to design cross-over points, or, for that matter, to design or modify any other GO as noted herein. These GOs include, without limitation, mutation of one or more parental character strings or one or more character string subsequences, multiplication of one or more parental character strings or one or more character string subsequences, fragmentation of one or more parental character strings or one or more character string subsequences, crossover between any of the one or more parental character strings or one or more character string subsequences or an additional character string, ligation of the one or more parental character strings or one or more character string subsequences, an elitism calculation, a calculation of sequence homology or sequence similarity of aligned strings, a recursive use of one or more genetic operator for evolution of character strings, application of a randomness operator to the one or more parental character strings or the one or more character string subsequences, a deletion mutation of the one or more parental character strings or one or more character string subsequences, an insertion mutation into the one or more parental character strings or one or more of character string subsequences, subtraction of the of the one or more parental character strings or one or more character string subsequences with an inactive sequence, selection of the of the one or more parental character strings or one or more character string subsequences with an active sequence, and death of the one or more parental character strings or one or more of character string subsequences. That is, any GO can include a component which maintains, removes, modifies, or in any way modulates one or more structural relationship during application of the GO in a GA.

Protein design cycles, involving cycling between theory and experiment, has led to recent advances in rational protein design (reviewed, e.g., in Street and Mayo (1999) "Computational Protein Design" *Structure with Folding and Design* 7(5):R105–R109). As noted above, performing iterative or recursive cycles of design, recombinant generation and screening and statistical analysis can be applied to the present invention (of course, these approaches can be used individually and in a variety of combinations); moreover, the combination of protein design cycles with random or partly random recombination processes can be used not only to produce proteins and nucleic acids of interest, but also in a learning approach to improve the protein design tools themselves.

With respect to modeling and structural analysis, a reductionist approach, in which protein positions are classified by their local environments, has aided development of appropriate energy expressions (reviewed in Street and Mayo (1999) "Computational Protein Design" *Structure with Folding and Design* 7(5):R105–R109). For examples of cycles of modeling and structural analysis, See, e.g., mayo.caltech.edu/ (on the world wide web); Gordon and Mayo (1999) "Branch-and-Terminate: A Combinatorial Optimization Algorithm for Protein Design" *Structure with Folding and Design* 7(9):1089–1098; Street and Mayo (1999) "Intrinsic B-sheet Propensities Result from van der Waals Interactions Between Side Chains and the Local Backbone" *Proc. Natl. Acad. Sci. USA*, 96, 9074–9076; Gordon et al. (1999) "Energy Functions for Protein Design" *Current Opinion in Structural Biology* 9(4):509–513; Street and Mayo (1999) "Computational Protein Design" *Structure with Folding and Design* 7(5):R105–R109; Strop and Mayo (1999) "Rubredoxin Variant Folds Without Iron" *J. Am. Chem. Soc.* 121(11):2341–2345; Gordon and Mayo (1998) "Radical Performance Enhancements for Combinatorial Optimization Algorithms based on the Dead-End Elimination Theorem" *J. Comp. Chem* 19:1505–1514; Malakauskas and Mayo (1998) "Design, Structure, and Stability of a Hyperthermophilic Protein Variant" *Nature Struct. Biol.* 5:470; Street and Mayo (1998) "Pairwise Calculation of Protein Solvent-Accessible Surface Areas" *Folding & Design* 3: 253–258. Dahiyat and Mayo (1997) "De Novo Protein Design: Fully Automated Sequence Selection" *Science* 278:82–87; Dahiyat and Mayo (1997) "Probing the Role of Packing Specificity in Protein Design" *Proc. Natl. Acad. Sci. USA* 94:10172–10177; Haney et al. (1997) "Structural basis for thermostability and identification of potential active site residues for adenylate kinases from the archaeal genus *Methanococcus*" *Proteins* 28(1): 117–30; and, Dahiyat et al. (1997) "Automated Design of the Surface Positions of Protein Helices" *Prot. Sci.* 6:1333–1337; Dahiyat et al. (1997) "De Novo Protein Design: Towards Fully Automated Sequence Selection" *J. Mol. Biol.* 273: 789–796. Protein design programs can be used to build or modify proteins with any selected set of design criteria and these design criteria can be used as filters for any GO as noted herein, and/or in recursive cycles of design (by modeling or structural analysis), in silico GO or GA application, and/or physical recombination of nucleic acids of interest.

For example, in Street and Mayo (1999) "Intrinsic B-sheet Propensities Result from van der Waals Interactions Between Side Chains and the Local Backbone" *Proc. Natl. Acad. Sci. USA*, 96, 9074–9076, the intrinsic secondary structure-forming propensities of naturally occurring amino acids were measured experimentally in host-guest studies and statistically by examination of a protein structure databank. As described, the linkage between dipeptides was modeled using a van der Waals energy function and derived Ramachandran plots for each of the amino acids. These data were used to determine the entropy and Helmholtz free-energy region of $\Phi$-$\Psi$ space. A cause of intrinsic $\beta$-sheet propensity was found to be the avoidance of steric clashes between an amino acid side chain and its local backbone.

Standard implementations of coulombic and salvation effects were determined to be of less significance. Thus, in addition to assigning linkages between amino acids or nucleotides in secondary and tertiary structures of proteins, linkages can be assigned e.g., at the dipeptide level (or any other level) to provide structure/design criteria. Again, these linkages can be selected for or disrupted, depending on the desired outcome, in selection of cross-over events or other GOs, e.g., in silico, according to the present invention. After application of the relevant GO, physical synthesis/recombination of relevant nucleic acids is optionally performed, as discussed herein. This process can be repeated recursively to improve both the nucleic acids/proteins of interest and to improve the relevant design or GO tools, e.g., by applying a learning heuristic to the analysis of results.

In a similar fashion, the design of surface positions of proteins (e.g., external helicies) has been considered (Dahiyat et al. (1997) "Automated Design of the Surface Positions of Protein Helices" *Prot. Sci.* 6:1333–1337) using an algorithm that considered side chain interactions. Similarly, the internal features of proteins for design criteria have been considered. For example, Dahiyat and Mayo (1997) "Probing the Role of Packing Specificity in Protein Design" *Proc. Natl. Acad. Sci. USA* 94:10172–10177, used a protein design algorithm (using a dead-end elimination theorem) that quantitatively considered side-chain packing to consider steric constraints on protein design. Penalization for exposed hydrophobic surface structures also improved design performance. More recently, pairwise expressions with one scalable parameter have been used that reproduce true buried and true solvent-accessible areas (Street and Mayo (1998) "Pairwise Calculation of Protein Solvent-Accessible Surface Areas" *Folding & Design* 3: 253–258).

As applied to the present invention, steric and other constraints can be used to consider structural linkages between amino acids (and in protein structures generally) and these linkages can be used to set filtering criteria for any GO or GA of interest, e.g., to select appropriate cross-over points between sequences of interest. As has already been mentioned, a feature of the invention optionally uses recursive cycles of design and experimentation, with observed results being used to improve both the activity of any protein of interest and the modeling tools used to predict cross-overs and to perform other GOs.

While amino acid linkages, motif maintenance and other structural/design criteria provide one basis for selecting cross-over points and performing other GOs, other approaches such as automated sequence selection can also be used. For example, in Dahiyat et al. (1997) "De Novo Protein Design: Towards Fully Automated Sequence Selection" *J. Mol. Biol.* 273:789–796, a quantitative design algorithm using a combined experimental and computational (e.g., the dead-end elimination theorem) approach was used to generate a ββα motif which had 20 out of 28 residues determined by modeling. Similarly, in Dahiyat and Mayo (1997) "De Novo Protein Design: Fully Automated Sequence Selection" *Science* 278:82–87 a novel sequence for an entire protein having a ββα structure was produced. Thus, in the context of the present invention, automated sequence selection and quantitative protein design is used both to provide sequences for in silico manipulation and recombination (i.e., as provided by any design process) and to make structure or activity predictions that can be used to modulate cross-over selection and other GOs, e.g., in silico. Again, these processes can include statistical as well as structure modeling approaches, in any combination, to provide complex cycles of design, testing and prediction. Essentially any linkage between structural elements, activity and statistically derived parameters can be maintained during cycles of in silico operations and physical recombination and/or selection.

As described by Malakauskas and Mayo (1998) "Design, Structure, and Stability of a Hyperthermophilic Protein Variant" *Nature Struct. Biol.* 5:470, design cycles can be used to improve protein activity as well. In this example, the stability of a thermophillic protein was increased by selecting residues for mutation based upon design algorithms. The combinatorial algorithm that was used simultaneously accounted for complex contributions of helix dipole interactions, improvement of secondary structure propensity, optimized core packing, increased burial of hydrophobic residues, and the like. In the context of the present invention, such combinatorial algorithms can be used to select desired improvements, e.g., based upon the functions of the algorithms and these desired improvements can be incorporated into one or more in silico sequence string to be recombined with any other sequence string, physically or by in silico methods. For example, residues which the algorithm indicates as targets for mutation are modified in silico, and cross-overs between the resulting modified sequence(s) and any other sequence(s) are designed to maintain or disrupt the modifications in any subsequent recombination steps.

An example of protein modification to maintain activity using a modified structure is found in Strop and Mayo (1999) "Rubredoxin Variant Folds Without Iron" *J. Am. Chem. Soc.* 121(11):2341–2345. As described, iron binding was eliminated from PFRD, while maintaining folding (including re-folding) and activity. One feature of the present invention is the modeling of proteins to perform such modifications, followed by in silico GOs and/or physical recombination to provide shuffled variants of proteins which are modeled to have particular activities. In addition to being valuable for the production of new proteins of interest, this recursive cycling process can be used as a learning heuristic to improve the predictive value of the modeling system.

Many design methods rely generally on energy expressions to evaluate the quality of different amino acid sequences for target protein structures (reviewed, e.g., in Gordon et al. (1999) "Energy Functions for Protein Design" *Current Opinion in Structural Biology* 9(4):509–513). For example, force fields tailored to protein design have been used, e.g., which consider van der Waals, packing specificity, hydrogen bonding, electrostatics, internal coordinate terms, salvation, entropy and the like, e.g., in an essentially simultaneous fashion (See also, Gordon et al., id and Malakauskas and Mayo (1998) "Design, Structure, and Stability of a Hyperthermophilic Protein Variant" *Nature Struct. Biol.* 5:470). Methods of implementing these algorithms in a combinatorial fashion (e.g., "branch and terminate" algorithms, "dead end elimination" algorithms and other approaches in the references herein) have been described (Gordon and Mayo (1999) "Branch-and-Terminate: A Combinatorial Optimization Algorithm for Protein Design" *Structure with Folding and Design* 7(9):1089–1098; Gordon and Mayo (1998) "Radical Performance Enhancements for Combinatorial Optimization Algorithms based on the Dead-End Elimination Theorem" *J. Comp. Chem* 19:1505–1514). In general, these methods can be used to bias or modulate any GO (e.g., cross-over selection) to maintain or alter any such force field or, more simply, to maintain or alter residue any sequence which the algorithms indicate to be of interest. That is, residues which the algorithm(s) indicates as targets for maintenance or mutation are modified or maintained in silico, as noted herein. Cross-overs between the resulting sequence(s) and any other sequence(s), or any other GO of interest, are designed to maintain or to disrupt the sequences of interest in any subsequent recombination step(s).

In any case, designed or modified proteins or character strings corresponding to proteins can be directly shuffled in silico, or, e.g., reverse translated and shuffled in silico and/or by physical shuffling (that is, many design algorithms apply primarily to proteins, while recombination is conveniently performed between coding nucleic acids-though as noted herein, direct recombination between proteins, particularly in silico, can also be performed). Thus, one aspect of the invention is the coupling of high-throughput rational design and in silico or physical shuffling and screening of genes to produce activities of interest. It is possible, using the present methods, to couple high-throughput rational design and random or semi-random recombination methods.

Similarly, molecular dynamic simulations such as those above and, e.g., Ornstein et al. (emsl.pnl.gov:2080/homes/tms/bms.html (on the world wide web); *Curr Opin Struct Biol* (1999) 9(4):509–13) provide for "rational" enzyme redesign by biomolecular modeling & simulation to find new enzymatic forms that would otherwise have a low probability of evolving biologically. For example, rational redesign of p450 cytochromes and alkane dehalogenase enzymes are a target of current rational design efforts. Any rationally designed protein (e.g., new p450 homologues or new alkaline dehydrogenase proteins) can be evolved by reverse translation and shuffling against either other designed proteins or against related natural homologous enzymes. Details on p450s can be found in Ortiz de Montellano (ed.) 1995, *Cytochrome P450 Structure and Mechanism and Biochemistry, Second Edition* Plenum Press (New York and London). Furthermore, the dynamic simulations can be used as predictors of residues of interest and coupling or linkages between residues of interest and cross-over selection (or other GOs) can be performed to specifically maintain or eliminate such linkages in silico.

In addition to the above approaches, homology modeling can also be used to provide structural predictors and to identify which residues are relevant to activity. See, Haney et al. (1997) "Structural basis for thermostability and identification of potential active site residues for adenylate kinases from the archaeal genus *Methanococcus*" *Proteins* 28(1):117–30. As applied to the present invention, this combination of structure and sequence analysis can be used to identify putative relationships between amino acids in a structure and can, accordingly, be used in cycles of design, in silico GO application, recombination, etc. Here again, cross-over selection or other GOs of interest can be maintained or eliminated in silico.

In addition to utilizing complex design algorithms, any structural information can be used to select cross-over sequences between nucleic acids (or to perform any other GO of interest). For example, comparison of protein crystal structures to predict crossover points based on structural rather than sequence homology considerations can be conducted and crossover can be effected by oligos to direct chimerization as discussed herein. This can be performed with or without the use of protein design algorithms, i.e., even simple inspection of crystal structure can provide a basis for selecting or eliminating particular residues. Thus, with knowledge about structure, either complex design algorithms or simple structural analysis can be used to select residues, secondary structures, tertiary structures, or the like, to be maintained or disrupted in any recombed coding nucleic acids.

Multivariate Sequence-Activity Modeling of Proteins; Optimization of Enzymatic activity by Rational Statistics.

As noted, statistical considerations can be applied to provide any of a variety of filters for identifying relationships between nucleic acid or protein sequences. This section describes how to analyze a large number of related protein sequences using modern statistical tools and how to derive novel protein sequences with desirable features using rational statistics and multivariate analysis.

Background Multivariate Data Analysis

Multivariate data analysis and experimental design is widely applied in industry, government and research centers. It is typically used for things like formulating gasoline, or optimizing a chemical process. In the classic example of gasoline formulation, there may be more than 25 different additives that can be added in different amounts and in different combinations. The output of the final product is also multifactorial (energy level, degree of pollution, stability etc. etc.). By using experimental design, a limited number of test formulations can be made where the presence and amounts of all additives are altered in a non-random fashion in order to maximally explore the relevant "formulation space." The appropriate measurements of the different formulations are subsequently analyzed. By plotting the datapoints in a multivariate (multidimensional) fashion, the formulation space can be graphically envisioned and the ideal combination of additives can be extracted. One of the most commonly used statistical tools for this type of analysis is Principal Component Analysis (PCA).

In this example, this type of matrix is used to correlate each multidimensional datapoint with a specific output vector in order to identify the relationship between a matrix of dependant variables Y and a matrix of predictor variables X. A common analytical tool for this type of analysis is Partial Least Square Projections to Latent Structures (PLS). This, for instance, is often used in investment banker's analysis of fluctuating stock prices, or in material science predictions of properties of novel compounds. Each datapoint can consist of hundreds of different parameters that are plotted against each other in an n-dimensional hyperspace (one dimension for each parameter). Manipulations are done in a computer system, which adds whatever number of dimensions are needed to be able to handle the input data. There are previously mentioned methods (PCA, PLS and others) that can assist in finding projections and planes so that hyperspace can be properly analyzed.

Background Sequence Analysis

Nucleotide or amino acid sequence analysis has traditionally been concentrated on qualitative pattern recognition (e.g., sequence classification). This mainly involves identifying sequences based on similarity. This works well for predictions or identifications of classification, but does not always correlate with quantitative values. For instance, a consensus transcriptional promoter may not be a good promoter in a particular application, but is, instead, the average promoter among an aligned group of related sequences.

To access the quantitative features of related biological sequences (DNA/RNA or amino acids) one can analyze the systematic variations (i.e. systematic absence of similarity) among aligned sequences with related biological activity. By applying different multivariate analysis tools (such as PLS) to protein sequences, it is possible to predict a sequence that generates better catalytic activity than the best one present in the analyzed set. Experimental data showing the success of the general method is described below.

Background Promoter Activity Multivariate Analysis

One, of the few references where multivariate data analysis has been applied to biological sequences was focused on analyzing a set of defined transcriptional promoters in order to see if one could predict a stronger promoter than any of those found in the training set (Jonssonet al. (1993) *Nucleic Acids Res.* 21:733–739).

In this example, promoter sequences were parametrizised. For simplicity, the physical-chemical differences between the respective nucleotides (A,C,G,T) were selected as equal, i.e. no nucleotide was considered more closely related to any other nucleotide. They were represented as four diametrically opposed corners of a cube forming a perfect tetrahedron. By assigning an origin to the center, each corner can be represented by a numerical coordinate, reflecting the numeric representation. Since the descriptors solely represents equal distribution of properties, any nucleoside can be positioned at any corner. See, FIG. 17.

Previous studies (Brunner and Bujard (1987) *EMBO J.* 6;3139–3144; Knaus and Bujard (1988) *EMBO J.* 7:2919–2923; Lanzer and Bujard (1988) *Proc. Natl. Acad. Sci.* 85:8973–8977) analyzed a set of 28 promoters that had been studied in detail in the identical context. The promoters included *E. coli* promoters, T5 phage promoters and a number of chimeric and synthetic promoters. They were all cloned as 68 bases (−49 to +19) inserted in front of a DHFR coding region. Relative transcriptional level was measured by dot-blot using the vector derived β-lactamase gene as internal standard.

Figures 14A, 14B:
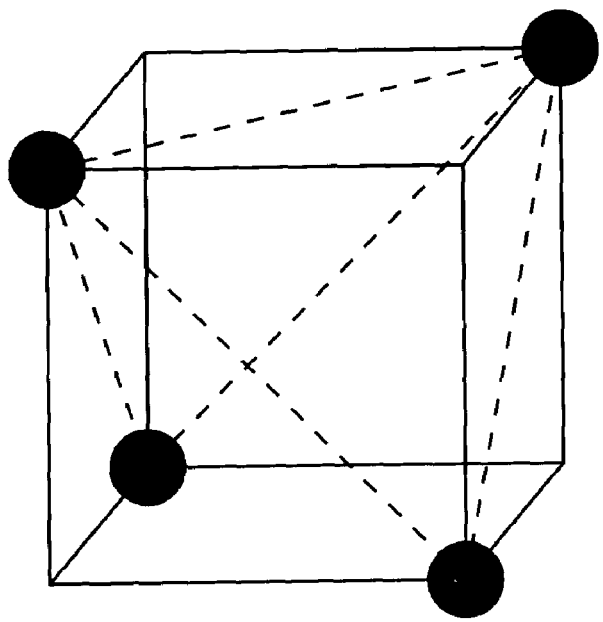
FIG. 14 is a schematic showing a geometric relationship between nucleotides.

In this example, when the 28 promoters, each with 68 nucleotides, were parameterized with the three descriptors as defined in FIG. 14, the result is a 28×204 matrix (28 promoters×68 nucleotides×3 parameters (steric bulk, hydrophobicity and polarizability)). The unique sequence of each promoter can be represented as a single point in a 204-dimensional hyperspace. This compilation of 28 promoters thus formed a cluster of 28 points in this space. The experimental data from previous studies noted above was repeated and the generated transcription levels plotted against the cluster of 28 points generated in the 204 dimensional hyperspace using PLS. Half of the promoters (14) were subsequently used to build a statistical model and the other half to test it. This was showed to generate a good correlation for calculated vs. observed promoter strength.

Two new promoters were constructed based on extrapolations of the generated model, and in both cases were shown to be significantly better than the best promoter present among the 28 initial promoters.

Multivariate Analysis And Protein Sequence

The same analytical methods can be applied to protein sequences. Signal peptides have been characterized using multivariate analysis showing good correlation between location in hyperspace and final physical localization (Sjóstróm et al. (1987) *EMBO J.* 6:823–831). The main difference between nucleotides and amino acids being that instead of qualitative descriptors of the nucleotides (see FIG. 14), quantitative descriptors have to be used to parameterize amino acids. The relevant features of the amino acids (steric bulk, hydrophobicity and polarizability) have been determined and can be extracted from the literature (Hellberg et al. (1986) *Acta Chem. Scand.* B40:135–140; Jonsson et al., (1989) *Quant. Struct.—Act. Relat.* 8:204–209).

Following shuffling and characterization of shuffled proteins, the mutated proteins are analyzed, both those that are "better" and those that are "worse" than the initial sequences. Statistical tools (such as PLS) can be used to extrapolate novel sequences that are likely to be better than the best sequence present in the analyzed set. Cross-overs can be selected (or other GOs performed) that provide for generation of the extrapolated sequences.

Modelling Protein Sequence Space

As described above, any protein encoded by a DNA sequence can be plotted as a distinct point in multidimensional space using statistical tools. A "normal" 1 kb gene can constitute, e.g., about 330 amino acids. Each amino acid can be described by, e.g., three major 2]physico-chemical quantitative descriptors (steric bulk, hydrophobicity and polarizability) for each amino acid (other descriptors for proteins are largely dependent on these three major descriptors). See also, Jonsson et al. (1989) *Quant. Struct.—Act. Relat.* 8:204–209. Thus, a 1 kb gene is modeled in 330 (number of amino acids)×20 (possible amino acids at each position)×3 (the three main descriptors noted above, for each amino acid)=19,800 dimensions. Because of the extended nature of sequence space, a number of shuffled sequences are used to validate sequence activity related predictions. The closer the surrounding sequences are in space (percent similarity), the higher the likelihood that predictive value can be extracted. Alternatively, the more sequence space which is analyzed, the more accurate predictions become. This modeling strategy can be applied to any available sequence. As described above, cycles of design and experimentation can be used to refine the model.

Alternatively, neural networks can be used to learn a type of pattern and predict the generated outcome of given variations. Examples of such neural networks include Schneider and Wrede (1998) "Artificial neural networks for computer-based molecular design" *Prog Biophys Mol Biol* 1998;70(3):175–222; Schneider et al. (1998) "Peptide design by artificial neural networks and computer-based evolutionary search" *Proc Natl Acad Sci USA* 95(21)-12179–84; and Wrede et al. (1998) "Peptide design aided by neural networks: biological activity of artificial signal peptidase I cleavage sites" *Biochemistry* 37(11):3588–93.

The prognostic value of plotting a large number of shuffled sequences is described above. Two additional approaches can also be used. First, plotting as many chimeric progeny in a library as possible vs. an enzymatic activity using, for example, PLS (partial least square projections to latent structures) can be performed. If enough data is available, the sequence-activity plot forms a function that can be extrapolated outside of the experimental data to produce an in-silico sequence corresponding to an activity higher than the best training set. Second, all related sequences can be plotted and certain sequences grouped with given related activities. Using this matrix, subsequent genes can immediately be grouped with appropriate activity or new related activities can be directly screened for by a subset of the sequenced clones. Cross-overs can be selected to produce any desired recombinants generated by the set.

An overall issue for the above strategy is the availability of enough related sequences generated through shuffling to provide useful information. An alternative to shuffling sequences is to apply the modeling tools to all available sequences, e.g., the GenBank database and other public sources. Although this entails massive computational power, current technologies make the approach feasible. Mapping all available sequences provides an indication of sequence space regions of interest. In addition, the information can be used as a filter which is applied to in silico shuffling events to determine which virtual progeny are preferred candidates for physical implementation (e.g., synthesis and/or recombination as noted herein). Thus, cross-overs and other GOs are selected to provide preferred recombinants and/or substrates for shuffling.

Identifying Crossover Sites for Synthetic Shuffling

As discussed herein and, e.g., in "OLIGONUCLEOTIDE MEDIATED NUCLEIC ACID RECOMBINATION" by Crameri et al., Filed Jan. 18, 2000, U.S. Ser. No. 09/484, 850, Synthetic shuffling optionally uses bridging oligos to force crossovers at defined location(s) in order to generate chimeric progeny. The general concept of defining the location for forced crossover on certain primary, secondary and tertiary sequence based considerations is discussed herein. Alternatively statistical matrixes such as Markov chains can be used to pinpoint ideal crossover locations. This example presents two alternative criteria for defining crossover locations based on statistical considerations.

Co-variation of amino acids during evolution allows proteins to retain a given fold or function while altering other traits, such as specificity. The co-variation identified in a large dataset can be useful in addressing possible crossover locations as it identifies co-evolving amino acids in a given family and allows bridging oligos to be engineered so that such functional constraints are retained.

The difficulty with this type of analysis has been that the signal from structurally/functionally constrained amino acids are masked by a much larger set of amino acids that show covariance due to phylogenetic relationship. Separating the functional from the phylogenetic covariance has been typically performed by consideration of high quality crystal structure information. However, other approaches are feasible.

Approach 1

For example, as described by Wollenberg and Atchley (2000) *Proc. Natl. Acad. Sci. USA* 97; 3288–3291, a statistical approach is used to separate phylogenetic association vs. functional association of a given amino acid covariance. This approach uses a parametric bootstrap algorithm to construct a statistical distribution that reflects the association between amino acids exclusively resulting from common ancestry (and chance) and subtracts those positions from all the positions showing covariance.

Intersite association is determined using Mutual Information (MI) statistics (Shannon & Weaver (1949) *The mathematical theory of information.* Univ. Illinois Press, Urbana, Ill.; Applebaum (1996) *Probability and information: An integrated approach* Cambridge Univ. Press, New York). MI measures the extent of association between two positions in a sequence beyond that expected from chance. The mutual information MIXY between sites X and Y is calculated as:

$$MI_{XY} = \sum_i \sum_j P(X_i, Y_j) \log_n \frac{P(X_i, Y_j)}{P(X_i)P(Y_j)},$$

where $P(X_i)$ is the probability of I at site X, $P(Y_j)$ is the probability of j at site Y, and $P(X_i,Y_j)$ is the joint probability of i at site X and j at site Y ($X \neq Y$). The maximum MI value occurs when the variation at two sites is perfectly correlated. The data presented by Wollenberg and Atchley uses the sequence elements as symbol variables with no underlying metric. The same statistical correlation can be done using the principal components for each amino acid. Replacing the symbols with true physicochemical properties can improve the significance of the MI relationship.

Setting a statistical acceptability threshold permits the identification, within a quantifiable error, of those intersite associations most probably arising from structural/functional causes. The reminder of the intersite associations can be deemed originating from phylogenetic resemblance. Cross-overs or other GOs are selected to produce the intersite associations of interest.

Approach Two

Pollock et al. (1999) *J. Mol. Biol.* 287:187–198 present a maximum likelihood method to identify coevolving protein residues. The data is reduced to a two-state system at each site using size and charge as amino acids characteristics. This reduces the complexity of coevolutionary relationships and aids in identifying the primary component of pairwise coevolution. The same method can be used with the principal components of each amino acid, ensuring a gradual nomination of entities, instead of simple binary nomination, resulting in significantly higher resolution and lower noise levels.

In short, by binary characterization of each position and comparison of all of the nodes in a matrix of all amino acids in all proteins present in the homology-cluster, correlations are scored (maximum likelihood) and related to the phylogentic dendrogram generated for the same cluster. A covariance correlation can be used to identify which residues are functionally/structurally linked. See also, Pollock et al. (1999), id. Cross-overs are selected to maintain these relationships.

Shuffling of Cladistic Intermediates

The present invention provides for the shuffling of "evolutionary intermediates." In the context of the present invention, evolutionary intermediates are artificial constructs which are intermediate in character between two or more homologous sequences, e.g., when the sequences are grouped into an evolutionary dendogram.

Nucleic acids are often classified into evolutionary dendograms (or "trees") showing evolutionary branch points and, optionally, relatedness. For example, cladistic analysis is a classification method in which organisms or traits (including nucleic acid or polypeptide sequences) are ordered and ranked on a basis that reflects origin from a postulated common ancestor (an intermediate form of the divergent traits or organisms). Cladistic analysis is primarily concerned with the branching of relatedness trees (or "dendograms") which shows relatedness, although the degree of difference can also be assessed (a distinction is sometimes made between evolutionary taxomomists who consider degrees of difference and those who simply determine branch points in an evolutionary dendogram (classical cladistic analysis); for purposes of the present invention, however, relatedness trees produced by either method can produce evolutionary intermediates).

Cladistic or other evolutionary intermediates can be determined by selecting nucleic acids which are intermediate in sequence between two or more extant nucleic acids. Although the sequence may not exist in nature, it still represents a sequence which is similar to a sequence in nature which had been selected for, i.e., an intermediate of two or more sequences represents a sequence similar to the postulated common ancestor of the two or more extant nucleic acids. Thus, evolutionary intermediates are one preferred shuffling substrate, as they represent "pseudo selected" sequences, which are more likely than randomly selected sequences to have LO activity.

One benefit of using evolutionary intermediates as substrates for shuffling (or of a using oligonucleotides which correspond to such sequences) is that considerable sequence diversity can be represented in fewer starting substrates (i.e., if starting with parents A and B, a single intermediate "C" has at least a partial representation of both A and B). This simplifies the oligonucleotide synthesis scheme for gene reconstruction/recombination methods, improving the efficiency of the procedure. Further, searching sequence databases with evolutionary intermediates increases the chances of identifying related nucleic acids using standard search programs such as BLAST.

Intermediate sequences can also be selected between two or more synthetic sequences which are not represented in nature, simply by starting from two synthetic sequences. Such synthetic sequences can include evolutionary intermediates, proposed gene sequences, or other sequences of interest that are related by sequence. These "artificial intermediates" are also useful in reducing the complexity of gene reconstruction methods and for improving the ability to search evolutionary databases.

Accordingly, in one significant embodiment of the invention, character strings representing evolutionary or artificial intermediates are first determined using alignment and sequence relationship software and then synthesized using oligonucleotide reconstruction methods. Alternately, the intermediates can form the basis for selection of oligonucleotides used in the gene reconstruction methods herein.

Several of the following sections describe implementations of this approach using hidden Markov model threading and other approaches.

In Silico Shuffling Using Hidden Markov Model Threading

A concern with synthetic shuffling is the assumption that each amino acid present among the parents is an independent entity and add (or does not add) function in a given functional dimension by itself. When shuffling using DNAse I based methods, this problem is avoided because recombination during assembly occurs as 20–200 bp fragments and, thus, each amino acid exists in its evolutionary context among other amino acids that have co-evolved in a given direction due to selective pressure of the functional unit (gene or promoter or other biological entity). By capturing the co-variance normally existing within a family of genes, either wild type or generated through regular shuffling, a significant number of biologically inactive progeny are avoided, improving the quality of the generated library. Artificially generated progeny may be inactive due to structural, modular or other subtle inconsistencies between the active parents and the progeny.

One way of weeding out unwanted non co-variance progeny is to apply a statistical profile such as Hidden Markov Model (HMM) on the parental sequences. An HMM matrix generated (e.g., as in FIG. 15) can capture the complete variation among the family as probabilities between all possible states (i.e. all possible combinations of amino acids, deletions and insertion). The matrix resulting from the analyzed family is used to search assorted databases for additional members of the family that are not similar enough to be identified by standard BLAST algorithms of any one particular sequence, but which are similar enough to be identified when probing using a probabilistic distribution pattern based on the original family.

Figure 15:
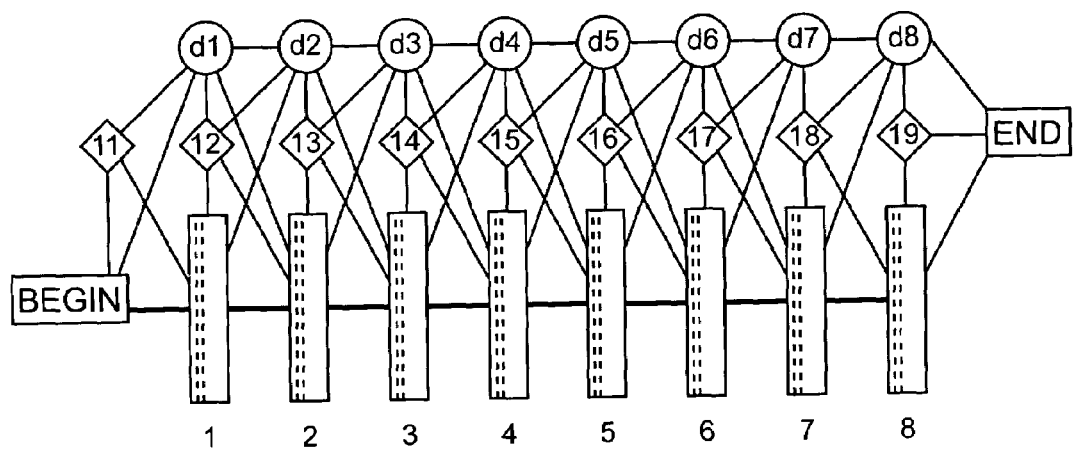
FIG. 15 is a schematic of an HMM matrix.

The HMM matrix shown in FIG. 15 exemplifies a family of 8 amino acid peptides. In each position, the peptide can be a specific amino acid (one of the 20 present in the boxes), an insertion (diamonds), or a deletion (circles). The probability for each to occur is dependent on how often it occurs among the compiled parents. Any given parent can subsequently be 'threaded' through the profile in such way that all allowed paths are given a probability factor.

HMM can be used in other ways as well. Instead of applying the generated profile to identify previously unidentified family members, the HMM profile can be used as a template to generate de novo family members (e.g., intermediate members of a cladistic tree of nucleic acids). For example, the program, HMMER is available (hmmer.wustl.edu/, on the world wide web). This program builds a HMM profile on a defined set of family members. A subprogram, HMMEMIT, reads the profile and constructs de novo sequences based on that. The original purpose of HMMEMIT is to generate positive controls for the search pattern, but the program can be adapted to the present invention by using the output as in silico generated progeny of a HMM profile defined shuffling. According to the present invention, oligonucleotides corresponding to these nucleic acids are generated for recombination, gene reconstruction and screening.

As the sequence context of each position is accounted for in a probabilistic fashion, the number of non-active progeny is significantly lower than a shuffling reaction that simply randomly selects such progeny. Crossover between genetic modules (structural, functional, or non-defined) occur where they occur in nature (i.e. among the parents) and co-evolution of point mutations or structural elements is retained throughout the shuffling process.

Example Alogrithm for Generating Sequence Intermediates from Sequence Alignments The following is an outline for a program for generating sequence intermediates from alignments of related parental nucleic acids.

```
Given an alignment of sequences which code for the parents, and an alignment which codes for
the children
for each child sequence
    for each parent sequence
        for each window
            if the parent sequence and child sequence match for this window
                If this window not already covered by sequences in segment list
                    Try to expand window, 5' and 3' until too many mismatches
                    Add final expanded segment to segment list for this sequence
for each child sequence
    set position to start of sequence
    do the following until the end of the child sequence is reached
        Search through segments finding a segment that extends the longest from a point
before position (this is most like the parent segment)
        If one is found add to optimal path list and set position to end of found segment
        if one is not found increment current position
    display segments from optimal path list
```

Normalization of Libraries—Use of Positive or Negative Activity Data

One aspect of the present invention is to use positive or negative data in sequence design and selection methods, either in silico, or in physical processing steps, or both. The use of positive or negative data can be in the context of a learning heuristic, a neural network or by simply using positive or negative data to provide logical or physical filters in design and library synthesis processes. Learning networks are described supra. and provide one convenient way of using positive or negative data to increase the chances that additional sequences which are subsequently generated will have a desired activity. The ability to use negative data to reduce the %, size of libraries to be screened provides a considerable advantage, as screening is often a limiting step in generating improved genes and proteins by forced evolution methods. Similarly, the use of positive data to bias libraries towards sequences of interest is another way of focusing libraries.

For example, as noted, in addition to a neural net learning approach, positive or negative data can be used to provide a physical or logical "filter" for any system of interest. That is, sequences which are shown to be inactive provide useful information about the likelihood that closely related sequences will also prove to be inactive, particularly where active sequences are also identified. Similarly, sequences which are active provide useful information about the likelihood that closely related sequences will also prove to be active, particularly where inactive sequences are also identified. These active or inactive sequences can be used to provide a virtual or physical filter to bias libraries (physical or virtual) toward production of more active members.

For example, when using negative data, physical subtraction methods use hybridization to inactive members under selected stringency conditions (often high stringency, as many libraries produced by the methods herein comprise homologous members) to remove similar nucleic acids from libraries which are generated. Similarly, hybridization rules or other parameters can be used to select against members that are likely to be similar to inactive sequences. For example, oligonucleotides used in gene reconstruction methods can be biased against sequences which have been shown to be inactive. Thus, in certain methods, libraries or character strings are filtered by subtracting the library or set of character strings with members of an initial library of biological polymers which display activity below a desired threshold.

When using positive data, physical enrichment methods use hybridization to active members under selected stringency conditions (often high stringency, as many libraries produced by the methods herein comprise homologous members) to isolate similar nucleic acids which comprise the members of libraries to be produced. Similarly, hybridization rules or other parameters can be used to select for members that are likely to be similar to active sequences. For example, oligonucleotides used in gene reconstruction methods can be biased towards sequences which have been shown to be active. Thus, in certain methods, libraries or character strings are filtered by biasing the library or set of character strings with members of an initial library of biological polymers which display activity above a desired threshold.

Similarly, in silico approaches can be used to produce libraries of inactive sequences, rather than active sequences. That is, inactive sequences can be shuffled in silico to produce libraries of clones that are less likely to be active. These inactive sequences can be physically generated and used to subtract libraries (typically through hybridization to library members) generated by other methods. This subtraction reduces the size of the library to be screened, primarily through the elimination of members that are likely to be inactive.

Example—Motif Filtering

Selections or screens often yield too many "positive" clones to cost-effectively sequence all of the positive or negative clones. However, if sequence motifs are identified that are enriched or depopulated in either the positive or the negative clones, then this bias is used in the construction of synthetic libraries that are biased toward "good" motifs and biased away from "bad" motifs.

If each contiguous selected region or motif (e.g., the selected window can be, e.g., a 20 base region) is thought of as a separate gene or gene element, one can measure the change in gene frequencies before and after a selection or screen. Motifs that increase in frequency in the positive clones are characterized as "good" and motifs whose frequency is reduced in the positive clones are characterized as "bad." Second generation libraries are synthesized in which the library is selected to be enriched for good motifs and depopulated with bad motifs, using any filtering or learning process as set forth herein.

A variety of methods for measuring frequencies of motifs in populations of genes are available. For example, one can hybridize analyte sequences to a gene chip or other array of nucleic acids with the motifs of interest encoded in a spatially addressable fashion, e.g., using gene chips as provided by Affymetrix (Santa Clara, Calif.), or other gene chip manufacturers. Similarly, hybridization to membranes containing spatially addressable motifs and measuring relative signal intensities for probe before and after selection can also be performed in an essentially similar fashion, e.g., using standard Southern or northern blot methods. Relative ratios of identified desirable/undesirable features on the chips also provides an indication of overall library quality. Similarly, phage display or other expression libraries can be used to assess library features, i.e., by evaluating expression products.

Alternatively, real time quantitative PCR (e.g., TaqMan) can be performed where PCR oligos are highly discriminating for the feature of interest. This can be done by, for example, having a polymorphism unique to the motif present at or near the 3' end of an oligo such that it will only prime the PCR efficiently if there is a perfect match. Real time PCR product analysis by, e.g., FRET or TaqMan (and related real time reverse-transcription PCR) is a family of known techniques for real time PCR monitoring that has been used in a variety of contexts (see, Laurendeau et al. (1999) "TaqMan PCR-based gene dosage assay for predictive testing in individuals from a cancer family with INK4 locus haploinsufficiency" Clin Chem 45(7):982–6; Laurendeau et al. (1999) "Quantitation of MYC gene expression in sporadic breast tumors with a real-time reverse transcription-PCR assay" Clin Chem 59(12):2759–65; and Kreuzer et al. (1999) "LightCycler technology for the quantitation of bcr/ab1 fusion transcripts" *Cancer Research* 59(13):3171–4.

If the gene family of interest is highly similar to begin with (for example, over 90% sequence identity), then one can simply sequence the population of genes before and after selection. If several sequencing primers up and down the gene are used, then one can look at the sequences in parallel on a sequencing gel. The sequence polymorphisms near the primer can be read out to see the relative ratio of bases at any given site. For example, if the population starts out with 50% T and 50% C at a given position, but 90% T and 10% after selection, one could easily quantitate this base ratio from a sequencing run that originates near the polymorphism. This method is limited, because as one gets further from the primer and reads through more polymorphisms, the mobilities of the various sequences gets increasingly variable and the traces begin to run together. However, as the cost of sequencing continues to decline and the cost of oligos continues to decrease, one solution is simply to sequence with many different oligos up and down the gene.

Example: Fractional Distillation of Sequence Space

Typical sequence spaces are very large compared to the number of sequences that can be physically cloned and characterized. Computational tools exist with which to describe subsets of sequence space which are predicted to be enriched for clones with properties of interest (see, supra). However, there are assumptions and computational limitations inherent to these models. Methods for fractionating sequence space such that it is enriched for molecules which are predicted by a given model to have greater or lesser fitness with respect to a phenotype of interest would be useful for testing such predictive models.

A simple example of how this would work is as follows. There are about 1027 possible shuffled IFNs (a fairly typical protein in terms of size) based on the naturally occurring human IFN gene family. This is larger than the number that can be easily screened. If one's goal is to evolve shuffled human IFNs that are active, e.g., on mouse cells, then one could use the information in the literature that shows that residues 121 and 125 from human IFN alpha 1 confer improved activity when transplanted onto other human IFNs such as IFN-$\alpha$2a. If one assumes that this motif confers improved activity in many different contexts, then one can create a large pool of shuffled IFN genes (typically on the order of $10^{9}$–$10^{12}$), convert them to ssDNA, pass them over an affinity column consisting of an oligonucleotide complementary human IFN alpha1 over these residues, wash under appropriate stringency, elute the bound molecules, PCR amplify the eluted genes, clone the material, and perform functional tests on the expressed clones. This protocol allows one to physically bias a library of shuffled genes strongly in favor of containing this motif which is predicted by this very simple model to confer an improvement in the desired activity.

Ideally, one takes populations that are enriched for the motif and populations that are depopulated with the motif. Both populations are analyzed (say 1000 clones from each population). The hypothesis is then "tested" asking whether this fractionation of sequence space biased the average fitness in the predicted way. If it did, then one could "accept" the hypothesis and scale up the screen of that library. One could also test a number of design algorithms by affinity based fractionation, accept the ones that are supported by the results of the experiment, and then perform the affinity selections in series so that one enriches for clones that meet the design criteria of multiple algorithms.

In this model, shuffling, such as family shuffling, is used as the first order design algorithm. However, additional design algorithms are integrated downstream of the shuffling to further fractionate a sequence space based on simple design heuristics. The method can be performed at the nucleic acid level with any design algorithm that can be translated into a nucleic acid selection scheme.

A number of variations on this example are useful for reducing the size of libraries that are produced by physical or virtual filtering processes.

For example, affinity electing oligonucleotides that encode motifs of interest prior to gene recombination/resynthesis (either physically or in silico) reduces the diversity of populations of nucleic acids that are produced in gene recombination/resynthesis methods as noted herein.

Similarly, oligonucleotides encoding motifs can be selected by enzymatically degrading molecules that are not perfectly matched with the oligos, e.g., again prior to gene recombination/resynthesis methods. Alternately, genes that match imperfectly with the oligonucleotides can be selected for, e.g., by binding to mutS or other DNA mismatch repair proteins.

Polymerization events during recombination/gene synthesis protocols can be primed using one or more oligos encoding the motif(s) of interest. That is, mismatches at or near the 3' end of hybridized nucleic acids reduce or block elongation. In this variation, only newly polymerized molecules are allowed to survive (used in subsequent library construction/selection steps). This can be done, for example, by priming reverse transcription of RNA and then degrading the RNA.

Another approach is to make the template specifically degradeable. For example, DNA with a high frequency of uracil incorporation can be synthesized. Polymerase-based synthesis is primed with oligos and extended with dNTPs containing no uracil. The resulting products are treated with uracil glycosylase and a nuclease that cleaves at apurinic sites, and the degraded template removed. Similarly, RNA nucleotides can be incorporated into DNA chains (synthetically or via enzymatic incorporation); these nucleotides then serve as targets for cleavage via RNA endonucleases. A variety of other cleavable residues are known, including certain residues which are targets for enzymes or other residues and which serve as cleaveage points in response to light, heat or the like. Where polymerases are currently not available with activity permitting incorporation of a desired cleavage target, such polymerases can be produced using shuffling methods to modify the activity of existing polymerases, or to acquire new polymerase activities.

Localized motifs can easily be translated into affinity selection procedures. However, one sometimes wants to impose a rule that molecules have multiple sequence features that are separated in space in the gene (e.g., 2, 3, 4, 5, 6, etc. sequence features). This can be timed into a selection by making a nucleic acid template that contains all motifs of interest separated by a flexible linker. The $T_m$ for molecules having all motifs is greater than for molecules having only one or two of the motifs. It is, therefore, possible to enrich for molecules having all motifs by selecting for molecules with high $T_m$s for the selecting oligo(s).

A "gene" of many such motifs strung together can be synthesized separated by flexible linkers or by bases such as inosine that can base pair promiscuously. One would then select for genes with high $T_m$s for the selecting nucleic acid. Careful design of the selecting nucleic acid template allows one to enrich for genes having a large number of sequence motifs that are predicted to bias genes containing them toward having a phenotype of interest.

If there is little information about whether any given motif is predicted to favorably bias the library, the technique can still be used. A set of motifs is defined, e.g., based upon sequence conservation between different homologs, or the motifs can even be randomly selected motifs. As long as the sequence space is not isotropic (equally dense with good members in all directions), then one can simply fractionate the sequence space based on a designed or on a random set of motifs, measure the average fitness of clones in the region of sequence space of interest, and then prospect more heavily in the regions that give the highest fitness.

In addition to simple sequence alignment methods, there are more sophisticated approaches available for identifying regions of interest such as macromolecule binding sites. Fork example, U.S. Pat. No. 5,867,402 to Schneider, et al (1999) "COMPUTATIONAL ANALYSIS OF NUCLEIC ACID INFORMATION DEFINES BIDING SITES" proposes methods in which binding sites are defined based upon the individual information content of a particular site of interest. Substitutions within the binding site sequences can be analyzed to determine whether the substitution causes a deleterious mutation or a benign polymorphism. Methods of identifying new binding sites using individual information content are also proposed. This approach can be used in the context of the present invention as one way of identifying sequences of interest for in silico manipulation of the sequences.

Motif Breeding

Rational design can be used to produce desired motifs in sequences or sequence spaces of interest. However, it is often difficult to predict whether a given designed motif will be expressed in a functional form, or whether its presence will affect another property of interest. An example of this is the process of designing glycosylation sites into proteins such that they are accessible to cellular glycosylation machinery and such that they do not negatively affect other properties of the protein such as blocking binding to another protein by virtue of steric hindrance by the attached polysaccaride groups.

One way of addressing these issues is to design motifs or multiple variations of motifs into multiple candidate sites within the target gene. The sequence space is then screened or selected for the phenotype(s) of interest. Molecules that meet the specified design criterion threshold are shuffled together, recursively, to optimize properties of interest.

Motifs can be built into any gene. Exemplary protein motifs include: N-linked glycosylation sites (i.e. Asn-X-Ser), O-linked glycosylation sites (i.e. Ser or Thr), protease sensitive sites (i.e. cleavage by collagenase after X in P-X-G-P) Rho-dependent transcriptional termination sites for bacteria, RNA secondary structure elements that affect the efficiency of translation, transcriptional enhancer elements, transcriptional promoter elements, transcriptional silencing motifs, etc.

High Throughput Rational Design

In addition to, or in conjunction with the rational design approaches described supra, high throughput rational design methods are also useful. In particular, high throughput rational design methods can be used to modify any given sequence in silico, e.g., before recombination/synthesis. For example, Protein Design Automation (PDA) is one computationally driven system for the design and optimization of proteins and peptides, as well as for the design of proteins and peptides.

Typically, PDA starts with a protein backbone structure and designs the amino acid sequence to modify the protein's properties, while maintaining it's three dimensional folding properties. Large numbers of sequences can be manipulated using PDA, allowing for the design of protein structures (sequences, subsequences, etc.). PDA is described in a number of publications, including, e.g., Malakauskas and Mayo (1998) "Design, Structure and Stability of a Hyperthermophilic Protein Variant" *Nature Struc. Biol.* 5:470; Dahiyat and Mayo (1997) "De Novo Protein Design: Fully Automated Sequence Selection" *Science,* 278, 82–87. DeGrado, (1997) "Proteins from Scratch" *Science,* 278: 80–81; Dahiyat, Sarisky and Mayo (1997) "De Novo Protein Design: Towards Fully Automated Sequence Selection" *J. Mol. Biol.* 273:789–796; Dahiyat and Mayo (1997) "Probing the Role of Packing Specificity in Protein Design" *Proc. Natl. Acad. Sci. USA,* 94:10172–10177; Hellinga (1997) "Rational Protein Design—Combining Theory and Experiment" *Proc. Natl. Acad. Sci. USA,* 94:10015–10017; Su and Mayo (1997) "Coupling Backbone Flexibility and Amino Acid Sequence Selection in Protein Design" *Prot. Sci.* 6:1701–1707; Dahiyat, Gordon and Mayo (1997) "Automated Design of the Surface Positions of Protein Helices" *Prot. Sci.,* 6:1333–1337; Dahiyat and Mayo (1996) "Protein Design Automation" *Prot. Sci.,* 5:895–903. Additional details regarding PDA are available, e.g., at xencor.com (on the world wide web).

In the context of the present invention, PDA and other design methods can be used to modify sequences in silico, which can be synthesized/recombined in shuffling protocols as set forth herein. Similarly, PDA and other design methods can be used to manipulate nucleic acid sequences derived following selection methods. Thus, design methods can be used recursively in recursive shuffling processes.

1N Silico Shuffling: Computational Methods for Designing Useful Bridging Oligonucleotides to Facilitate Low Homology Recombination Physically shuffling sequences that are less than about 50% identical at the DNA level often results in a low number of recombination sites between the sequences to be shuffled. A number of approaches to solving this problem are described herein, including design and construction of "cross-over" or "bridging" oligonucleotides, the use of intermediate "diplomat" sequences and the like.

In one general approach, as noted herein, one way to increase the number of crossover sites is to build "bridging" or "cross-over" oligonucleotides that have some number of bases (e.g., sufficient to mediate hybridization, typically, e.g., about 20 or more, though fewer can also be used) identical to one parent, then some number (typically, e.g., also about 20 or more bases) identical to the second parent.

In the context of the present invention, there are at least four basic ways of providing bridging oligos, i.e., 1) arbitrarily choosing bridging oligos; 2) making all possible bridging oligos; 3) making a subset of possible bridging oligonucleotides based upon known features of the sequences to be shuffled (e.g., to permit particular domains or subdomains to be recombined or disrupted, e.g., to account for 3-D or empirically derived considerations), and 4) using computational methods to optimize bridging oligonucleotide selection and design. This last option is especially useful in the context of the present invention, although the first three approaches can also be applicable.

As noted above, computational methods exist to examine a protein sequence to assess the structural stability of variants, based on either an available crystal structure, or energy minimization mapping to the crystal structure of a homologous sequence (see, e.g., references cited in previous section). Although the number of variants that can be screened in this way are large (e.g., on the order of $10^{80}$ or more) this is still only a very small fraction of the total possible sequence space even for a single small protein (with 20 variants in a 300 amino acid protein, $10^{80}$ represents one variant out of every $2^{300} \times 10^{220}$.) These methods are, therefore, currently limited in the way in which variants are chosen. Further, because only a fraction of sequence space is analyzed, variants are often selected to be close to the active site.

For convenience and clarity of illustration, this section uses shuffling of p450 super family members to illustrate certain methods of performing relevant steps of the invention; however, the steps are universally applicable to other systems. For example, the methods are applicable to any set or sets of proteins for which more than one sequence is available and for which at least one structure is either known or can be calculated/estimated.

In brief, desirable crossover points can be selected between two or more sequences, e.g., following an approximate sequence alignment, performing Markov chain modeling, or any other desired selection method. This desirable subset of all possible crossover points is smaller than all possible crossover points, and all possible recombinants between two or more low homology sequences using these reasonable crossover points can be computationally generated. These recombinants are analyzed for their ability to fit one or more of the possible structures that are either known or calculated for one or more of the selected parental sequences. In this way, it is possible to identify particularly productive crossover points, and thus to again reduce the total number of bridging oligonucleotides, this time to a number which can actually be synthesized to provide a useful number of bridging oligonucleotides to facilitate low homology shuffling reactions. This bridging oligonucleotide selection method also greatly expands the effective sequence space that can be analysed computationally.

Description of the Basic Method

In summary, the following steps are performed in bridging oligonucleotide design and selection, as noted above.

1. Identify proteins from which chimeric recombinants are desireable. These optionally encode actual or putative homologous structures. (Steps 2–5 below are optionally omitted and only bridging oligoucleotides fulfilling given criteria (retaining certain substructures, statistical considerations, etc.) are used for subsequent library generation).

2. Computationally generate all possible single crossover events between each pair of sequences (or a pre-selected subset of these, e.g., designed to provide crossover points in regions of low, but existing, homology). For two 1000 amino acid proteins, all possible cross-over points is, roughly, 2×1000×1000 crossover points (2×10$^6$) (the number can vary somewhat, depending on how the sequences are aligned). For ten 1000 amino acid proteins this number is 45 (number of possible pairwise combinations)×2×1000×1000 (9×10$^7$).

3. Calculate the structures of all parents ("template structures"), either from direct measurement (i.e., crystallography, NMR etc.), or by energy minimization to the known structure of a related protein. As noted above, PDA is one particularly useful computationally driven system for the design and optimization of proteins and peptides, as well as for the design of proteins and peptides.

Many other energy minimization and other protein/ nucleic acid design algorithms are known and available. These include computer search algorithms in protein modification and design (Desjarlais and Clarke (1999) *Structure Fold Des;*7(9):1089–98), Theoretical and algorithmical optimization of the dead-end elimination theorem (Desmet et al. (1997) *Pac Symp Biocomput* 122–33), fast conformational search strategies for finding low energy structures of model proteins (Beutler (1996) *Protein Sci* 5(10):2037–43), and efficient algorithms for protein sequence design and the analysis of certain evolutionary fitness landscapes (Kleinberg (1999)*J Comput Biol* 6(3–4):387–404). In addition, other evolutionary protein design programs can be used, such as evolutionary algorithms in computer-aided molecular design (Clark and Westhead (1996) *J Comput Aided Mol Des* 10(4):337–58).

Genetic algorithms can be used to solve problems in protein threading, both in this context and generally in relation to the present invention (see also, Yadgari et al. (1998) Ismb 6:193–202). In protein threading approaches, a sequence is aligned and identified to the fold with which it is most compatible (this process is often referred to in the literature as protein "threading"). Genetic algorithms can be used to solve such problems, which are not expected to have simple polynomial solutions. See also, Yadgari et al, id.

4. Use protein design algorithms to assess the ability of each in silico recombinant to fold into structures resembling the template structures.

5. Set a filtering criteria (e.g., stability, structural similarity of one or more region of the putative cross-over construct to one or more parental, desired regions of hydrophobicity or hydrophilicity, the ability of selected regions to form particular secondary, tertiary or even quatranery structures, or any other useful criteria) by which recombinants are selected or rejected depending upon their ability to fit into one or more of the template structures.

6. Identify crossover points allowed by the selected filtering criteria.

7. Design bridging oligonucleotides homologous to each position in each pair of parents where a recombination point is allowed. Oligonucleotide design is optionally further refined, for example, to ensure that a disallowed crossover is not facilitated, or that all crossover oligos have identical melting temperatures to each parent (and to all other crossover oligos generated). For example, desirable primers optionally incorporate any of several useful properties. These include, inter alia, that the hybridization of the primers to their complementary sequences is uniform; that individual primers hybridize only to their complementary regions in the system, and do not significantly cross hybridize with primers complementary to other parental sequence regions; that if there are selected regions associated with the primers that are not complementary to a target (e.g., cloning sites, secondary PCR primer binding sites, etc.) that the selected regions do not hybridize to a corresponding probe set, etc. One available computer program for primer selection is the MacVectorsm program from Kodak. An alternate program is the MFOLD program (Genetics Computer Group, Madison Wis.) which predicts secondary structure of, e.g., single-stranded nucleic acids. In addition to programs for primer selection, one of skill can easily design simple programs for any or all of the preferred primer design steps.

8. Synthesize crossover oligonucleotides.

9. Synthesize, clone or otherwise obtain parental genes, or subsequences thereof.

10. Fragment parental genes or subsequences (either by actual cleavage or by synthetic generation of parental gene fragments, or both).

11. Assemble mixtures of parental gene fragments and crossover oligonucleotides.

12. Express and assay recombinants.

13. Repeat as desired to obtain an activity (new or improved) of interest. Note that in subsequet rounds, sequence information from selected recombinants can be used to provide information for bridging oligonucleotide design for subsequent steps. In addition, any selected recombinant can be used in any diversity generation reaction according to any other protocol herein (e.g., shuffling, mutagenesis, or any in silico procedure herein).

The types of enzymatic activity that arise as a result of this overall process depend upon the recombinants chosen and the template structure screened against. For example, there is putative structural homology between *Bacillus megaterium* P450BM-3 and murine nitric oxide synthase protein (see Degtyarenko, K. N. & Archakov, A. I. (1993) FEBS 332, 1–8.). Novel P450s can be computationally constructed by making all possible recombinants between the nitric oxide synthase N-terminus and the entire P450, following comparison with a P450 template structure to eliminate undesired sequences. Libraries of synthesized variants are constructed that can be tested for alterations in various P450 properties, e.g., substrate range, acceptable electron donors, etc. Alternatively, in this example, novel nitric oxide synthases are computationally constructed by making all possible recombinants between the N-terminal domain of the P450 and the entire nitric oxide synthase and comparing putative recombinants resulting from the cross-overs with a nitric oxide template structure for one or more property (energy minimization, stability, etc., as noted above). Desirable sequences are constructed and functionally screened. For example, in this particular example, a functional screen on these enzymes can screen, e.g., for a different property rate of electron transfer and/or nitric oxide synthesis.

Variations on Methods for Computational Generation of Variants

A number of variations on the basic methods noted above can be performed, including the following specifically enumerated variations.

1. In step 2 above, other ways of computationally generating new protein sequences can be used. For example incremental truncation for the creation of hybrid enzymes 4) (ITCHY), circular permutations (with or without additional protein sequence insertions), sequence duplications, complementation, and many other techniques are applicable. Any approach that takes naturally occurring or artificial sequences and recombines them in silico can be used.

For example, Ostermeier et al. "A combinatorial approach to hybrid enzymes independent of DNA homology" (1999) *Nat Biotechnol* 17(12): 1205–9 describe incremental truncation for the creation of hybrid enzymes (ITCHY), that creates combinatorial fusion libraries between genes in a manner that is independent of DNA homology. The use of ITCHY and DNA shuffling to create interspecies or intraspecies fusion libraries between fragments of genes with little or no homology can identify a more diverse set of active fusion points including those in regions of nonhomology and those with crossover points that diverge from a sequence alignment.

Similarly, a variety of references describe circular permutations (with or without additional protein sequence insertions). These include, e.g., Baird et al. (1999) "Circular permutation and receptor insertion within green fluorescent proteins" *Proc Natl Acad Sci USA* 96(20):11241–6; Topell (1999) "Circularly permuted variants of the green fluorescent protein" *FEBS Lett* 457(2):283–9; Hennecke et al. (1999) "Random circular permutation of DsbA reveals segments that are essential for protein folding and stability" *J Mol Biol* 286(4): 1197–215; Hennecke and Glockshuber (1998) "Conversion of a catalytic into a structural disulfide bond by circular permutation" *Biochemistry* 37(50): 17590–7; Luger (1989) "Correct folding of circularly permuted variants of a beta alpha barrel enzyme in vivo" *Science* 243(4888):206–10; and Zhang and Schachman (1996) "In vivo formation of allosteric aspartate transcarbamoylase containing circularly permuted catalytic polypeptide chains: implications for protein folding and assembly" *Protein Sci* 5(7):1290–300. In brief, genes such as GFP, disulfide oxidoreductase DsbA, aspartate transcarbamoylase (ATCase) and others have been shown to be active even when extensively rearranged. For example, several rearrangements of GFPs, in which the amino and carboxyl portions are interchanged and rejoined with a short spacer connecting the original termini, still become fluorescent. These circular permutations have altered pKa values and orientations of the chromophore with respect to a fusion partner. Furthermore, certain locations within GFP tolerate insertion of entire proteins, and conformational changes in the insert can have profound effects on the fluorescence. For example, insertions of calmodulin or a zinc finger domain in place of Tyr-145 of a yellow mutant (enhanced yellow fluorescent protein) of GFP result in indicator proteins whose fluorescence can be enhanced upon metal binding. The calmodulin graft into enhanced yellow fluorescent protein can monitor cytosolic Ca(2+) in single mammalian cells. The tolerance of proteins for circular permutations and insertions shows that the folding process is robust and offers a general strategy for creating new diversified sequences, including completely non-homologous sequences which are joined by bridging oligonucleotides according to the present invention.

In one aspect, active sequences are produced by complementation. For example, Yang and Schachman (1993) "In vivo formation of active aspartate transcarbamoylase from complementing fragments of the catalytic polypeptide chains" *Protein Sci* 2(6):1013–23 and, e.g., Yang and Schachman (1996) "A bifunctional fusion protein containing the maltose-binding polypeptide and the catalytic chain of aspartate transcarbamoylase: assembly, oligomers, and domains" *Biophys Chem* 59(3):289–97 describe formation of an active stable enzyme in vivo, even with fragmented catalytic chains. Thus, as applied to the present invention, domains or other subsequences can be separately designed and synthesized and tested for complementary effects with one another. Because the domains/sequences are on separate chains, complementation can be used to assess combinatorial effects of the separate domains. This approach can increase the number of sequence combinations that are assessed for activity, without increasing the number of sequences that are actually synthesized.

2. Incomplete protein fragments or putative protein domains (e.g. from ESTs) can also be included in any recombination reaction. Domains can be approximately identified, or even arbitrarily designated, e.g., as described supra. Additional details regarding protein domain designation/identification are found, e.g., in Crameri et al. "OLIGONUCLEOTIDE MEDIATED NUCLEIC ACID RECOMBINATION" Filed Jan. 18, 2000; USSN: PCT/US00/01203.

For example, in the p450 example noted, there are at least 6 different forms of P450 known (see Degtyarenko and Archakov (1993) FEBS 332, 1–8; see also, Ortiz de Montellano (ed.) (1995) *Cytochrome P450 Structure Mechanism and Biochemistry, Second Edition* Plenum Press (New York and London) and the references cited therein). For example, as shown by Degtyarenko and Archakov, the molecular evolution of P450s, in contrast to that of many protein families, does not follow phylogeny. During the evolution of P450s, gene duplications and gene fusions, horizontal gene transfer and intron loss events have occurred. 'Weak' and 'strong' hierarchies in the clustering of P450 sequences can be shown.

The six different forms of p450s include prokaryotic and eukaryotic 3 part systems with separate FAD-containing, Fe—S and P450 (heme-containing) subunits; prokaryotic and eukaryotic 2 part systems with a combined FAD- and FMN-containing subunit and a P450 (heme-containing) subunit; at least one prokaryotic one-component system (*Bacillus megaterium* P450BM-3) with one polypeptide containing FAD- FMN-and heme- group, and at least one eukaryotic one-component system (murine nitric oxide synthase) with one polypeptide containing FAD- FMN-and heme- group.

Thus, the combined FAD- and FMN-containing subunit from either prokaryotic or eukaryotic 2-component systems are optionally computationally recombined with the FAD-FMN-containing domain of either of the one-component systems, and then tested against a one-component template structure. Likewise, the P450 subunits from either the 2 or 3 component systems can be computationally recombined with the heme-containing domain of the one-component system and then tested against a one-component template structure. The converse can also be performed, i.e., a domain from the one-component system can computationally recombined with a subunit from the multi-component systems, and screened in silico for one or more computed property, e.g., against a structure of one of the subunits as a template.

3. Potential sequences for recombination can also be identified by computational methods other than by direct homology or structural information, e.g. by the PRINTS system (Attwood TK, Beck Me., Bleasby AJ, Degtyarenko K, Parry Smith DJ Nucleic Acids Res 1996 Jan. 1;24(1): 182–8), Shotgun (Pegg and Babbitt (1999) *Bioinformatics* 15(9):729–40) independently evolving sequence modules (may correspond to folding units as in MasterCatalog (eragen.com, on the world wide web) and other sequence comparison methods.

For example, Pegg and Babbitt (id.) provide an example of using the Shotgun program to identify both new superfamily members and to reconstruct known enzyme superfamilies, using BLAST database searches. An analysis of the false-positive rates generated in the analysis and other control experiments show that high Shotgun scores indicate evolutionary relationships. Shotgun is also a useful tool for identifying subgroup relationships within superfamilies and for testing hypotheses about related protein families.

Similarly, PRINTS (e.g., Atwood et al., above) is a compendium of protein motif fingerprints derived from the OWL composite sequence database. Fingerprints are groups of motifs within sequence alignments whose conserved nature allows them to be used as signatures of family membership. Fingerprints can provide improved diagnostic reliability over single motif methods by virtue of the mutual context provided by motif neighbors. The database is now accessible via the UCL Bioinformatics Server on biochem.ucl.ac.uk/bsm/dbbrowser/ (on the world wide web). Atwood et al. describe the database, its compilation and interrogation software, and its Web interface. See also, Attwood et al. (1997) "Novel developments with the PRINTS protein fingerprint database" *Nucleic Acids Res* 25(1):212–7.

4. In addition to calculating all possible single crossovers for all pairwise combinations of parental genes, it is also possible to calculate multiple crossovers and compare those with the template structures. In this case it is possible to identify crossover oligos that should be used in combination to provide any computationally selected criteria.

Similarly, it is also possible to take all possible pairwise recombinants which are generated and then run all possible pairwise combinations of those recombinants with each other, or with other parents. This is useful if the program has an output feature where the number of bridging oligos for the different possible combinations of multiple parents are described. For example in a family of proteins A–F, A, B and D may have many productive crossovers with each other, A C, E and F may have many productive crossovers with each other, but there may be few between (B or D) and (C, E and F). This information is helpful in defining which combinations of parents are actually mixed when building the physical libraries.

5. Crossover points can also be "calculated" by simply comparing the structures (either from crystals, nmr, dynamic simulations, or any other available method) of proteins corresponding to nucleic acids to be recombined. All possible pairwise combinations of structures can be overlaid. Amino acids can be identified as possible crossover points when they overlap with each other on the parental structures (this can define closeness of fit; for example, the alpha carbons can be selected to be within 1 angstrom), or when they and their nearest neighbours overlap within similar distance criteria. Bridging oligos can be built for each crossover point. Thus, in this embodiment, in silico selection of recombinants and the step of cross-over selection in parental sequences are combined into a single simultaneous step.

An advantage to this approach is that structural analysis can be bypassed for resulting chimeras. This is because the chimeras have already been "pre-selected" for structural features that correspond to the parental sequences.

Variations on Structural Calculation Methods

Variations on the basic approach noted above can also be performed by varying calculation of structural information. Variations include the following.

1. The entire process can be conducted at the level of sequence domains, e.g., by identifying domains in a structure and then identifying homologous domains for each target domain. Calculations can be made for the ability of in silico recombinants to form a complete folded protein, or for any given domain to form a structural domain.

Using the one-component *Bacillus megaterium* P450BM-3 example, the FAD- and FMN-containing domain and the P450 (heme containing) domain can be treated as structurally separable. Thus the FAD- and FMN-containing domain can be computationally recombined with the FAD- and FMN-containing domain of murine nitric oxide synthase, the FAD- and FMN-containing subunit of 2-component sytems, and the FAD-containing subunit of 3-component systems. These can be fit either to a complete P450BM-3 template structure, or to a template structure that only includes the FAD- and FMN-containing domain and is not constrained by the presence of the heme-containing domain.

In this way all possible computational recombinants can be computed for each domain of a protein, and then these domains can be computationally combined, followed by synthesis of appropriate cross-over oligonucleotides. This reduces the complexity of the overall computational problem of recombining low similarity sequences.

2. Other known structures (e.g., for proteins other than the parental structures) can also be used as template structures. In addition, calculated structures can also be used. This can include, e.g., any of the sequences or sequence intermediates described herein, including evolutionary intermediates, diplomat sequences, and the like.

Formats for Making and Using Bridging Oligonucleotides to Facilitate Low Homology Recombination As noted, this invention provides, inter alia, a process by which variants produced computationally can be synthesized physically, without the need for massive parallel synthesis of each individual calculated gene. Parental genes can be cloned or synthesized and then fragmented (e.g., by the uracil cleavage methods noted supra, e.g., to allow for multi-library formats as noted below), or fragments of the parents can simply be synthesized. The fragments are mixed with the relevant crossover oligos, assembled, expressed and assayed. Instead of individually synthesizing each in silico identified gene, one oligonucleotide is sufficient for each crossover oligonucleotide. Many different progeny can then be synthesized from gene fragments and crossover oligonucleotides simply by assembling different combinations of parents and oligonucleotides. The actual synthesis is performed either as each individual variant synthesized independently, or in increasing pool sizes up to a single library of all variants, e.g., by using a 96-well parallel format (or other common screening format).

For example, the following steps can be used in one basic format of this method.

1. Each variant is synthesized, e.g., in a single microtitre well, e.g., by including two parents and one bridging oligonucleotide.
2. Selected (e.g., calculated to be useful, e.g., according to any selected set of criteria) crossover oligonucleotides are synthesized, representing different pairs of parents. For example, for 5 parents, there are 10 different pairwise combinations of crossover oligonucleotides.
3. Libraries containing all parents but a different oligonucleotide at each position are synthesized.
4. Oligonucleotides are included in the same reaction with all relevant parents to generate all selected crossovers.

Combinations of the above steps can be performed, separately or individually and in different orders.

In the case of permutated or truncated parental sequences, it is useful to synthesize, clone or otherwise construct the truncated or permutated parental sequences, as well as the bridging oligonucleotides.

Iterative Variations

The method can also incorporate a variety of variations to produce an iterative process. The following are example variations.

1. Improved variants from the first round of recombination can be shuffled by any of the processes noted herein, including use of bridging or cross-over oligonucleotides.
2. The computation itself can be iteratively improved. For example, first round improved variants can be computationally fitted to the parental structures used, and the improved structures can then be calculated, e.g., by energy minimization. New structures of the improved variants are, e.g., used as template structures for second round calculated recombinants. In this way it is also possible to gain structural understanding of functional changes which are obtained. Neural net and/or other statistical approaches can be used to further refine second round recombinants.
3. This approach is productively combined with the formats described above that do not produce single pooled libraries. For example, taking, e.g., 5 genes, 10 possible pairwise libraries are synthesized. Each library is separately screened for hits. Picking one or a few hits from each library identifies tens to hundreds of different recombinants (because they come from different libraries). Comparisons of the calculated structures of these recombinants can be used to identify regions of structural constraint and regions where there is more flexibility. The second round of in silico recombinants can then be compared with all of these calculated structures as a second generation of templates. This identifies parts of the structure that are relevant for function, and ensures that recombinants are rejected in silico where the deviate from template structural features that are relevant for the function under consideration. Alternatively, a "consensus" template structure can be built by giving different importance weightings to different parts of the protein, and a single structure used.

Non-Oligonucleotide Dependent in Silico Shuffling

As discussed herein, many of the methods of the invention involve generating diversity in sequence strings in silico, followed by oligonucleotide gene recombination/synthesis methods. However, non-oligonucleotide based recombination methods are also appropriate. For example, instead of generating oligonucleotides, entire genes can be made which correspond to any diversity created in silico, without the use of oligonucleotide intermediates. This is particularly feasible when genes are sufficiently short that direct synthesis is possible.

In addition, it is possible to generate peptide sequences directly from diverse character string populations, rather than going through oligonucleotide intermediates. For example, solid phase polypeptide synthesis can be performed. For example, solid phase peptide arrays can be constructed by standard solid phase peptide synthesis methods, with the members of the arrays being selected to correspond to the in silico generated sequence strings.

In this regard, solid phase synthesis of biological polymers, including peptides has been performed at least since the early "Merrifield" solid phase peptide synthesis methods, described, e.g., in Merrifield (1963) *J. Am. Chem. Soc.* 85:2149–2154 (1963). Solid-phase synthesis techniques are available for the synthesis of several peptide sequences on, for example, a number of "pins." See e.g., Geysen et al. (1987) *J. Immun. Meth.* 102:259–274, incorporated herein by reference for all purposes. Other solid-phase techniques involve, for example, synthesis of various peptide sequences on different cellulose disks supported in a column. See, Frank and Doring (1988) *Tetrahedron* 44:6031–6040. Still other solid-phase techniques are described in U.S. Pat. No. 4,728,502 issued to Hamill and WO 90/00626. Methods of forming large arrays of peptides are also available. For example, Pirrung et al., U.S. Pat. No. 5,143,854 and Fodor et al., PCT Publication No. WO 92/10092, disclose methods of forming arrays of peptides and other polymer sequences using, for example, light-directed synthesis techniques. See also, Stewart and Young, *Solid Phase Peptide Synthesis*, 2d. ed., Pierce Chemical Co. (1984); Atherton et al. (1989) *Solid Phase Peptide Synthesis*, IRL Press, Greene, et al. (1991) *Protective Groups In Organic Chemistry*, 2nd Ed., John Wiley & Sons, New York, N.Y. and Bodanzszyky (1993) *Principles of Peptide Synthesis* second edition Springer Verlag, Inc. NY. Other useful information regarding proteins is found in R. Scopes, *Protein Purification*, Springer-Verlag, N.Y. (1982); Deutscher, *Methods in Enzymology Vol. 182: Guide to Protein Purification*, Academic Press, Inc. N.Y. (1990); Sandana (1997) *Bioseparation of Proteins*, Academic Press, Inc.; Bollag et al. (1996) *Protein Methods, 2$^{nd}$ Edition* Wiley-Liss, NY; Walker (1996) *The Protein Protocols Handbook* Humana Press, NJ, Harris and Angal (1990) *Protein Purification Applications: A Practical Aipproach* IRL Press at Oxford, Oxford, England; Harris and Angal *Protein Purification Methods: A Practical Approach* IRL Press at Oxford, Oxford, England; Scopes (1993) *Protein*

*Purification: Principles and Practice* 3rd *Edition* Springer Verlag, N.Y.; Janson and Ryden (1998) *Protein Purification: Principles High Resolution Methods and Applications, Second Edition* Wiley-VCH, NY; and Walker (1998) *Protein Protocols on CD-ROM* Humana Press, NJ; and the references cited therein.

In addition to proteins and nucleic acids, it should be appreciated that character string diversity generated in silico can be corresponded to other biopolymers. For example, the character strings can be corresponded to peptide nucleic acids (PNAs) which can be synthesized according to available techniques and screened for activity in any appropriate assay. See, e.g., Peter E. Nielsen and Michael Egholm (eds) (1999) *Peptide Nucleic Acids: Protocols and Applications* ISBN 1-898486-16–6 Horizon Scientific Press, Wymondham, Norfolk, U.K for an introduction to PNA synthesis and activity screening.

Assays—Physical Selection.

Directed Evolution by GAGGS, as in DNA shuffling, or classical strain improvement, or any functional genomics technology, can use any physical assays known in the art for detecting polynucleotides encoding desired phenotypes.

Synthetic genes are amenable to conventional cloning and expression approaches; thus, properties of the genes and proteins they encode can readily be examined after their expression in a host cell. Synthetic genes can also be used to generate polypeptide products by in-vitro (cell-free) transcription and translation. Polynucleotides and polypeptides can thus be examined for their ability to bind a variety of predetermined ligands, small molecules and ions, or polymeric and heteropolymeric substances, including other proteins and polypeptide epitopes, as well as microbial cell walls, viral particles, surfaces and membranes.

For example, many physical methods can be used for detecting polynucleotides encoding phenotypes associated with catalysis of chemical reactions by either polynucleotides directly, or by encoded polypeptides. Solely for the purpose of illustration, and depending on specifics of particular pre-determined chemical reactions of interest, these methods may include a multitude of techniques well known in the art which account for a physical difference between substrate(s) and product(s), or for changes in the reaction media associated with chemical reaction (e.g. changes in electromagnetic emissions, adsorption, dissipation, and fluorescence, whether UV, visible or infrared (heat). These methods also can be selected from any combination of the following: mass-spectrometry; nuclear magnetic resonance; isotopically labeled materials, partitioning and spectral methods accounting for isotope distribution or labeled product formation; spectral and chemical methods to detect accompanying changes in ion or elemental compositions of reaction product(s) (including changes in pH, inorganic and organic ions and the like). Other methods of physical assays, suitable for use in GAGGS, can be based on the use of biosensors specific for reaction product(s), including those comprising antibodies with reporter properties, or those based on in vivo affinity recognition coupled with expression and activity of a reporter gene. Enzyme-coupled assays for reaction product detection and cell life-death-growth selections in vivo can also be used where appropriate. Regardless of the specific nature of the physical assays, they all are used to select a desired property, or combination of desired properties, encoded by the GAGGS-generated polynucleotides. Polynucleotides found to have desired properties are thus selected from the library.

The methods of the invention optionally include selection and/or screening steps to select nucleic acids having desirable characteristics. The relevant assay used for the selection will depend on the application. Many assays for proteins, receptors, ligands and the like are known. Formats include binding to immobilized components, cell or organismal viability, production of reporter compositions, and the like.

In high throughput assays, it is possible to screen up to several thousand different shuffled variants in a single day. For example, each well of a microtiter plate can be used to run a separate assay, or, if concentration or incubation time effects are to be observed, every 5–10 wells can test a single variant (e.g., at different concentrations). Thus, a single standard microtiter plate can assay about 100 (e.g., 96) reactions. If 1536 well plates are used, then a single plate can easily assay from about 100–about 1500 different reactions. It is possible to assay several different plates per day; assay screens for up to about 6,000–20,000 different assays (i.e., involving different nucleic acids, encoded proteins, concentrations, etc.) is possible using the integrated systems of the invention. More recently, microfluidic approaches to reagent manipulation have been developed, e.g., by Caliper Technologies (Mountain View, Calif.) which can provide very high throughput microfluidic assay methods.

In one aspect, cells, viral plaques, spores or the like, comprising GAGGS shuffled nucleic acids, are separated on solid media to produce individual colonies (or plaques). Using an automated colony picker (e.g., the Q-bot, Genetix, U.K.), colonies or plaques are identified, picked, and up to 10,000 different mutants inoculated into 96 well microtiter dishes containing two 3 mm glass balls/well. The Q-bot does not pick an entire colony but rather inserts a pin through the center of the colony and exits with a small sampling of cells, (or mycelia) and spores (or viruses in plaque applications). The time the pin is in the colony, the number of dips to inoculate the culture medium, and the time the pin is in that medium each effect inoculum size, and each parameter can be controlled and optimized.

The uniform process of automated colony picking such as the Q-bot decreases human handling error and increases the rate of establishing cultures (roughly 10,000/4 hours). These cultures are optionally shaken in a temperature and humidity controlled incubator. Optional glass balls in the microtiter plates act to promote uniform aeration of cells and the dispersal of cellular (e.g., mycelial) fragments similar to the blades of a fermenter. Clones from cultures of interest can be isolated by limiting dilution. As also described supra, plaques or cells constituting libraries can also be screened directly for the production of proteins, either by detecting hybridization, protein activity, protein binding to antibodies, or the like. To increase the chances of identifying a pool of sufficient size, a prescreen that increases the number of mutants processed by 10-fold can be used. The goal of the primary screen is to quickly identify mutants having equal or better product titers than the parent strain(s) and to move only these mutants forward to liquid cell culture for subsequent analysis.

One approach to screening diverse libraries is to use a massively parallel solid-phase procedure to screen cells expressing shuffled nucleic acids, e.g., which encode enzymes for enhanced activity. Massively parallel solid-phase screening apparatus using absorption, fluorescence, or FRET are available. See, e.g., U.S. Pat. No. 5,914,245 to Bylina, et al. (1999); see also, kairos-scientific.com/ (on the world wide web); Youvan et al. (1999) "Fluorescence Imaging Micro-Spectrophotometer (FIMS)" *Biotechnology et alia*<et-al.com (on the world wide web)>1:1–16; Yang et al.

(1998) "High Resolution Imaging Microscope (HIRIM)" *Biotechnology et alia*, <et-al.com(on the world wide web) >4:1–20; and Youvan et al. (1999) "Calibration of Fluorescence Resonance Energy Transfer in Microscopy Using Genetically Engineered GFP Derivatives on Nickel Chelating Beads" posted at kairos-scientific.com (on the world wide web). Following screening by these techniques, sequences of interest are typically isolated, optionally sequenced and the sequences used as set forth herein to design new sequences for in silico or other shuffling methods.

Similarly, a number of well known robotic systems have also been developed for solution phase chemistries useful in assay systems. These systems include automated workstations like the automated synthesis apparatus developed by Takeda Chemical Industries, LTD. (Osaka, Japan) and many robotic systems utilizing robotic arms (Zymate II, Zymark Corporation, Hopkinton, Mass.; Orca, Beckman Coulter, Inc. (Fullerton, Calif.)) which mimic the manual synthetic operations performed by a scientist. Any of the above devices are suitable for use with C) the present invention, e.g., for high-throughput screening of molecules encoded by codon-altered nucleic acids. The nature and implementation of modifications to these devices (if any) so that they can operate as discussed herein will be apparent to persons skilled in the relevant art.

High throughput screening systems are commercially available (see, e.g., Zymark Corp., Hopkinton, Mass.; Air Technical Industries, Mentor, Ohio; Beckman Instruments, Inc. Fullerton, Calif.; Precision Systems, Inc., Natick, Mass., etc.). These systems typically automate entire procedures including all sample and reagent pipetting, liquid dispensing, timed incubations, and final readings of the microplate in detector(s) appropriate for the assay. These configurable systems provide high throughput and rapid start up as well as a high degree of flexibility and customization.

The manufacturers of such systems provide detailed protocols the various high throughput. Thus, for example, Zymark Corp. provides technical bulletins describing screening systems for detecting the modulation of gene transcription, ligand binding, and the like.

A variety of commercially available peripheral equipment and software is available for digitizing, storing and analyzing a digitized video or digitized optical or other assay images, e.g., using PC (Intel x86 or pentium chip-compatible DOS™, OS2™ WINDOWS™, WINDOWS NT™ or WINDOWS95™ based machines), MACINTOSH™, or UNIX based (e.g., SUN™ work station) computers.

Integrated systems for analysis typically include a digital computer with GO software for GAGGS, and, optionally, high-throughput liquid control software, image analysis software, data interpretation software, a robotic liquid control armature for transferring solutions from a source to a destination operably linked to the digital computer, an input device (e.g., a computer keyboard) for entering data to the digital computer to control GAGGS operations or high throughput liquid transfer by the robotic liquid control armature and, optionally, an image scanner for digitizing label signals from labeled assay components. The image scanner can interface with image analysis software to provide a measurement of probe label intensity. Typically, the probe label intensity measurement is interpreted by the data interpretation software to show whether the labeled probe hybridizes to the DNA on the solid support.

Current art computational hardware resources are fully adequate for practical use in GAGGS (any mid-range priced Unix system (e.g., for Sun Microsystems) or even higher end Ad Macintosh or PCs will suffice). Current art in software technology is adequate (i.e., there are a multitude of mature programming languages and source code suppliers) for design of an upgradable open-architecture object-oriented genetic algorithm package, specialized for GAGGS users with a biological background.

A Digital Apparatus for GOs

Various methods and genetic algorithms (GOs) can be used to perform desirable functions as noted herein. In addition, digital or analog systems such as digital or analog computer systems can control a variety of other functions such as the display and/or control of output files.

For example, standard desktop applications such as word processing software (e.g., Microsoft Word™ or Corel WordPerfect™) and database software (e.g., spreadsheet software such as Microsoft Excel™, Corel Quattro PrO™, or database programs such as Microsoft Access™ or Paradox™) can be adapted to the present invention by inputting one or more character string into the software which is loaded into the memory of a digital system, and performing a GO as noted herein on the character string. For example, systems can include the foregoing software having the appropriate character string information, e.g., used in conjunction with a user interface (e.g., a GUI in a standard operating system such as a Windows, Macintosh or LINUX system) to manipulate strings of characters, with GOs being programmed into the applications, or with the GOs being performed manually by the user (or both). As noted, specialized alignment programs such as PILEUP and BLAST can also be incorporated into the systems of the invention, e.g., for alignment of nucleic acids or proteins (or corresponding character strings) as a preparatory step to performing an additional GO on the resulting aligned sequences. Software for performing PCA can also be included in the digital system.

Systems for GO manipulation typically include, e.g., a digital computer with GO software for aligning and manipulating sequences according to the GOs noted herein, or for performing PCA, or the like, as well as data sets entered into the software system comprising sequences to be manipulated. The computer can be, e.g., a PC (Intel x86 or Pentium chip-compatible DOS,™ OS2,™ WINDOWS,™ WINDOWS NT,™ WINDOWS95,™ WINDOWS98,™ LINUX, Apple-compatible, MACINTOSH™ compatible, Power PC compatible, or a UNIX compatible (e.g., SUN™ work station) machine) or other commercially common computer which is known to one of skill. Software for aligning or otherwise manipulating sequences can be constructed by one of skill using a standard programming language such as Visualbasic, Fortran, Basic, Java, or the like, according to the methods herein.

Any controller or computer optionally includes a monitor which can include, e.g., a cathode ray tube ("CRT") display, a flat panel display (e.g., active matrix liquid crystal display, liquid crystal display), or others. Computer circuitry is often placed in a box which includes numerous integrated circuit chips, such as a microprocessor, memory, interface circuits, and others. The box also optionally includes a hard disk drive, a floppy disk drive, a high capacity removable drive such as a writeable CD-ROM, and other common peripheral elements. Inputting devices such as a keyboard or mouse optionally provide for input from a user and for user selection of sequences to be compared or otherwise manipulated in the relevant computer system.

The computer typically includes appropriate software for receiving user instructions, either in the form of user input into a set parameter fields, e.g., in a GUI, or in the form of preprogrammed instructions, e.g., preprogrammed for a variety of different specific operations. The software then converts these instructions to appropriate language for instructing the system to carry out any desired operation. For example, in addition to performing GO manipulation of character strings, a digital system can instruct an oligonucleotide synthesizer to synthesize oligonucleotides for gene reconstruction, or even to order oligonucleotides from commercial sources (e.g., by printing appropriate order forms or by linking to an order form on the internet).

The digital system can also include output elements for controlling nucleic acid synthesis (e.g., based upon a sequence or an alignment of a sequences herein), i.e., an integrated system of the invention optionally includes an oligonucleotide synthesizer or an oligonucleotide synthesis controller. The system can include other operations which occur downstream from an alignment or other operation performed using a character string corresponding to a sequence herein, e.g., as noted above with reference to assays.

Figure 13:
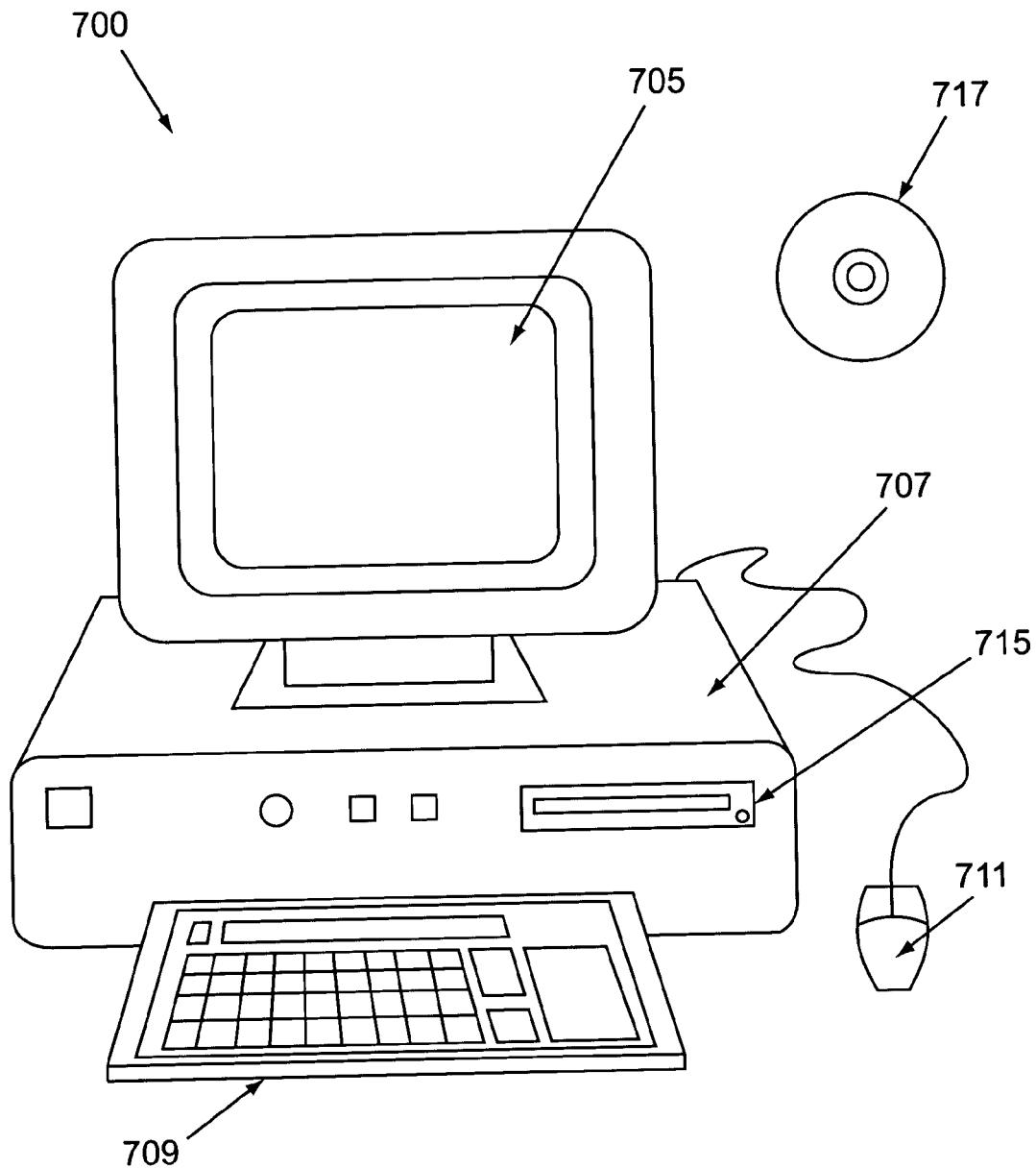
FIG. 13 is a schematic of a digital system of the invention.

In one example, GOs of the invention are embodied in a fixed media or transmissible program component containing logic instructions and/or data that when loaded into an appropriately configured computing device causes the device to perform a GO on one or more character string. FIG. 13 shows example digital device 700 that should be understood to be a logical apparatus that can read instructions from media 717, network port 719, user input keyboard 709, user input 711 or other inputting means. Apparatus 700 can thereafter use those instructions to direct GO modification of one or more character string, e.g., to construct one or more data set (e.g., comprising a plurality of GO modified sequences corresponding to nucleic acids or proteins). One type of logical apparatus that can embody the invention is a computer system as in computer system 700 comprising CPU 707, optional user input devices keyboard 709, and GUI pointing device 711, as well as peripheral components such as disk drives 715 and monitor 705 (which displays GO modified character strings and provides for simplified selection of subsets of such character strings by a user. Fixed media 717 is optionally used to program the overall system and can include, e.g., a disk-type optical or magnetic media or other electronic memory storage element. Communication port 719 can be used to program the system and can represent any type of communication connection.

The invention can also be embodied within the circuitry of an application specific integrated circuit (ASIC) or programmable logic device (PLD). In such a case, the invention is embodied in a computer readable descriptor language that can be used to create an ASIC or PLD. The invention can also be embodied within the circuitry or logic processors of a variety of other digital apparatus, such as PDAs, laptop computer systems, displays, image editing equipment, etc.

In one preferred aspect, the digital system comprises a learning component where the outcomes of physical oligonucleotide assembly schemes (compositions, abundance of products, different processes) are monitored in conjunction with physical assays, and correlations are established. Successful and unsuccessful combinations are documented in a database to provide justification/preferences for user-base or digital system based selection of sets of parameters for subsequent GAGGS processes involving the same set of parental character strings/nucleic acids/proteins (or even unrelated sequences, where the information provides process improvement information). The correlations are used to modify subsequent GAGGS processes to optimize the process. This cycle of physical synthesis, selection and correlation is optionally repeated to optimize the system. For example, a learning neural network can be used to optimize outcomes.

Embodiment in a Web Site.

The methods of this invention can be implemented in a localized or distributed computing environment. In a distributed environment, the methods may implemented on a single computer comprising multiple processors or on a multiplicity of computers. The computers can be linked, e.g. through a common bus, but more preferably the computer(s) are nodes on a network.

The network can be a generalized or a dedicated local or wide-area network and, in certain preferred embodiments, the computers may be components of an intra-net or an internet.

In one internet embodiment, a client system typically executes a Web browser and is coupled to a server computer executing a Web server. The Web browser is typically a program such as IBM's Web Explorer, Internet explorer, NetScape or Mosaic. The Web server is typically, but not necessarily, a program such as IBM's HTTP Daemon or other WWW daemon (e.g., LINUX-based forms of the program). The client computer is bi-directionally coupled with the server computer over a line or via a wireless system. In turn, the server computer is bi-directionally coupled with a website (server hosting the website) providing access to software implementing the methods of this invention.

A user of a client connected to the Intranet or Internet may cause the client to request resources that are part of the web site(s) hosting the application(s) providing an implementation of the methods of this invention. Server program(s) then process the request to return the specified resources (assuming they are currently available). A standard naming convention has been adopted, known as a Uniform Resource Locator ("URL"). This convention encompasses several types of location names, presently including subclasses such as Hypertext Transport Protocol ("http"), File Transport Protocol ("ftp"), gopher, and Wide Area Information Service ("WAIS"). When a resource is downloaded, it may include the URLs of additional resources. Thus, the user of the client can easily learn of the existence of new resources that he or she had not specifically requested.

The software implementing the method(s) of this invention can run locally on the server hosting the website in a true client-server architecture. Thus, the client computer posts requests to the host server which runs the requested process(es) locally and then downloads the results back to the client. Alternatively, the methods of this invention can be implemented in a "multi-tier" format wherein a component of the method(s) are performed locally by the client. This can be implemented by software downloaded from the server on request by the client (e.g. a to Java application) or it can be implemented by software "permanently" installed on the client.

In one embodiment the application(s) implementing the methods of this invention are divided into frames. In this paradigm, it is helpful to view an application not so much as a collection of features or functionality but, instead, as a collection of discrete frames or views. A typical application, for instance, generally includes a set of menu items, each of with invokes a particular frame—that is, a form which manifest certain functionality of the application. With this perspective, an application is viewed not as a monolithic body of code but as a collection of applets, or bundles of functionality. In this manner from within a browser, a user would select a Web page link which would, in turn, invoke a particular frame of the application (i.e., subapplication). Thus, for example, one or more frames may provide functionality for inputing and/or encoding biological molecule(s) into one or more character strings, while another frame provides tools for generating and/or increasing diversity of the encoded character string(s).

In particular preferred embodiments, the methods of this invention are implemented as one or more frames providing, e.g., the following functionalit(ies). Function(s) to encode two or more biological molecules into character strings to provide a collection of two or more different initial character strings wherein each of said biological molecules comprises a selected set of subunits; functions to select at least two substrings from the character strings; functions to concatenate the substrings to form one or more product strings about the same length as one or more of the initial character strings; functions to add (place) the product strings to a collection of strings, and functions to implement any feature of GAGGS or any GO or GA as set forth herein.

The functions to encode two or more biological molecules can provide one or more windows wherein the user can insert representation(s) of biological molecules. In addition, the encoding function also, optionally, provides access to private and/or public databases accessible through a local network and/or the intranet whereby one or more sequences contained in the databases can be input into the methods of this invention. Thus, for example, in one embodiment, where the end user inputs a nucleic acid sequenced into the encoding function, the user can, optionally, have the ability to request a search of GenBank and input one or more of the sequences returned by such a search into the encoding and/or diversity generating function.

Methods of implementing Intranet and/or Intranet embodiments of computational and/or data access processes are well known to those of skill in the art and are documented in great detail (see, e.g., Cluer et al. (1992) A General Framework for the Optimization of Object-Oriented Queries, Proc SIGMOD International Conference on Management of Data, San Diego, Calif., Jun. 2–5, 1992, SIGMOD Record, vol. 21, Issue 2, June, 1992; Stonebraker, M., Editor; ACM Press, pp. 383–392; ISO-ANSI, Working Draft, "Information Technology-Database Language SQL", Jim Melton, Editor, International Organization for Standardization and American National Standards Institute, July 1992; Microsoft Corporation, "ODBC 2.0 Programmer's Reference and SDK Guide. The Microsoft Open Database Standard for Microsoft Windows™ and Windows NT™, Microsoft Open Database Connectivity™ Software Development Kit", 1992, 1993, 1994 Microsoft Press, pp. 3–30 and 41–56; ISO Working Draft, "Database Language SQL-Part 2:Foundation (SQL/Foundation)", CD9075-2: 199.chi.SQL, Sep. 11, 1997, and the like). Additional relevant details regarding web based applications are found in "METHODS OF POPULATING DATA STRUCTURES FOR USE IN EVOLUTIONARY SIMULATIONS" by Selifonov and Stemmer.

EXAMPLES

The following examples are intended to further illustrate the present invention and should not be considered to be limiting. One of skill will immediately recognize a variety of parameters which can be changed to achieve essentially similar results.

EXAMPLE 1

Decision Tree for Example GAGGS Process

Figure 1B:
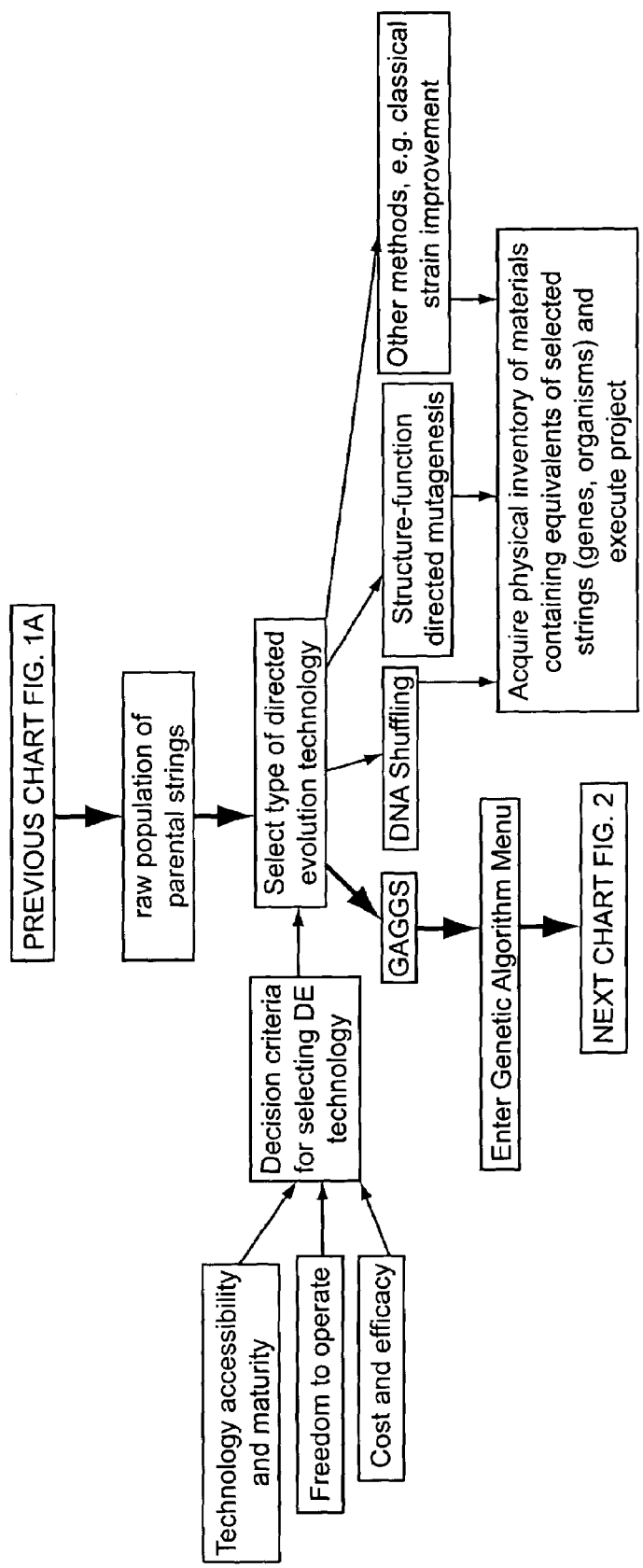
Figure 1C:
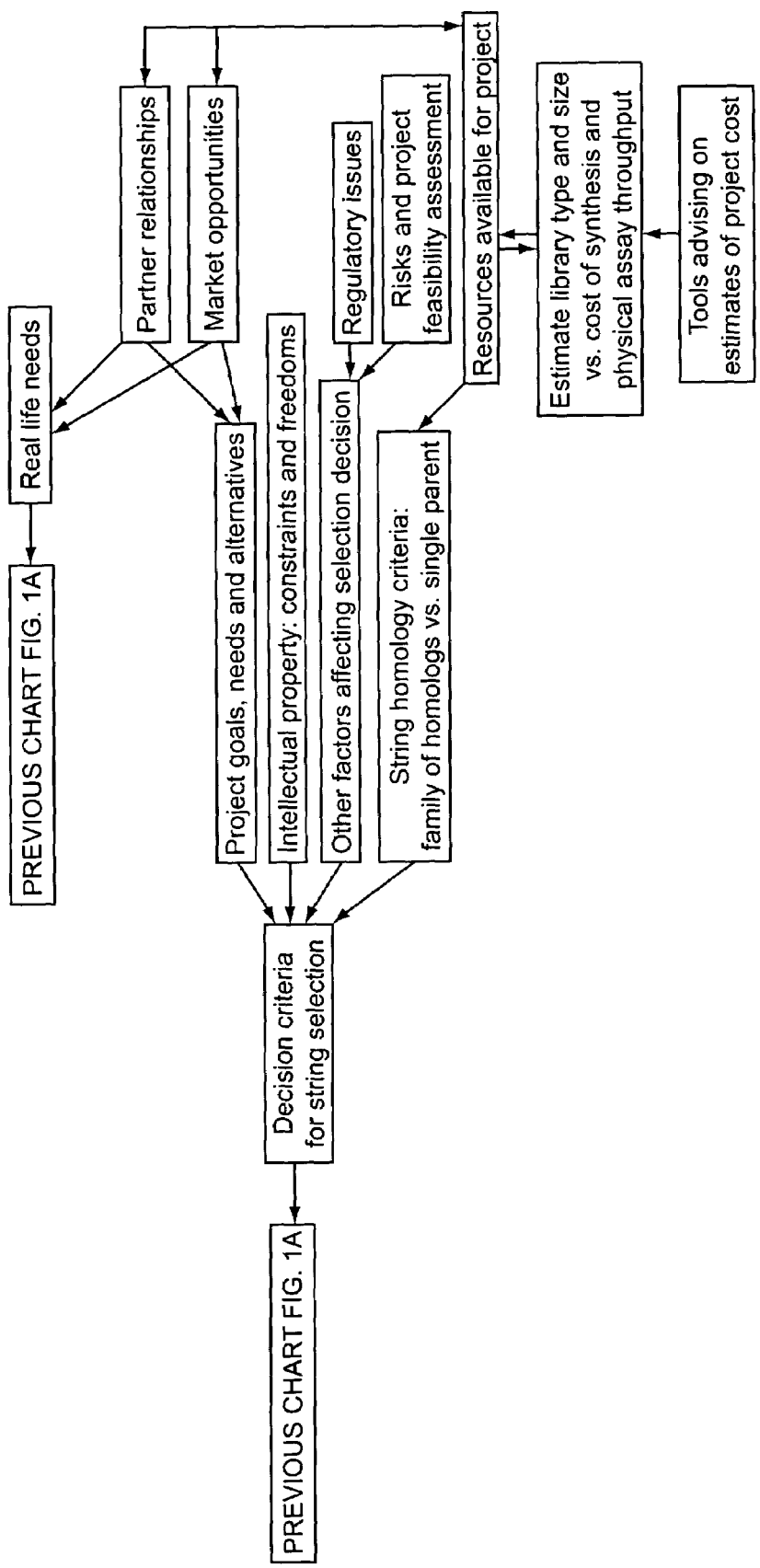
Figure 3A:
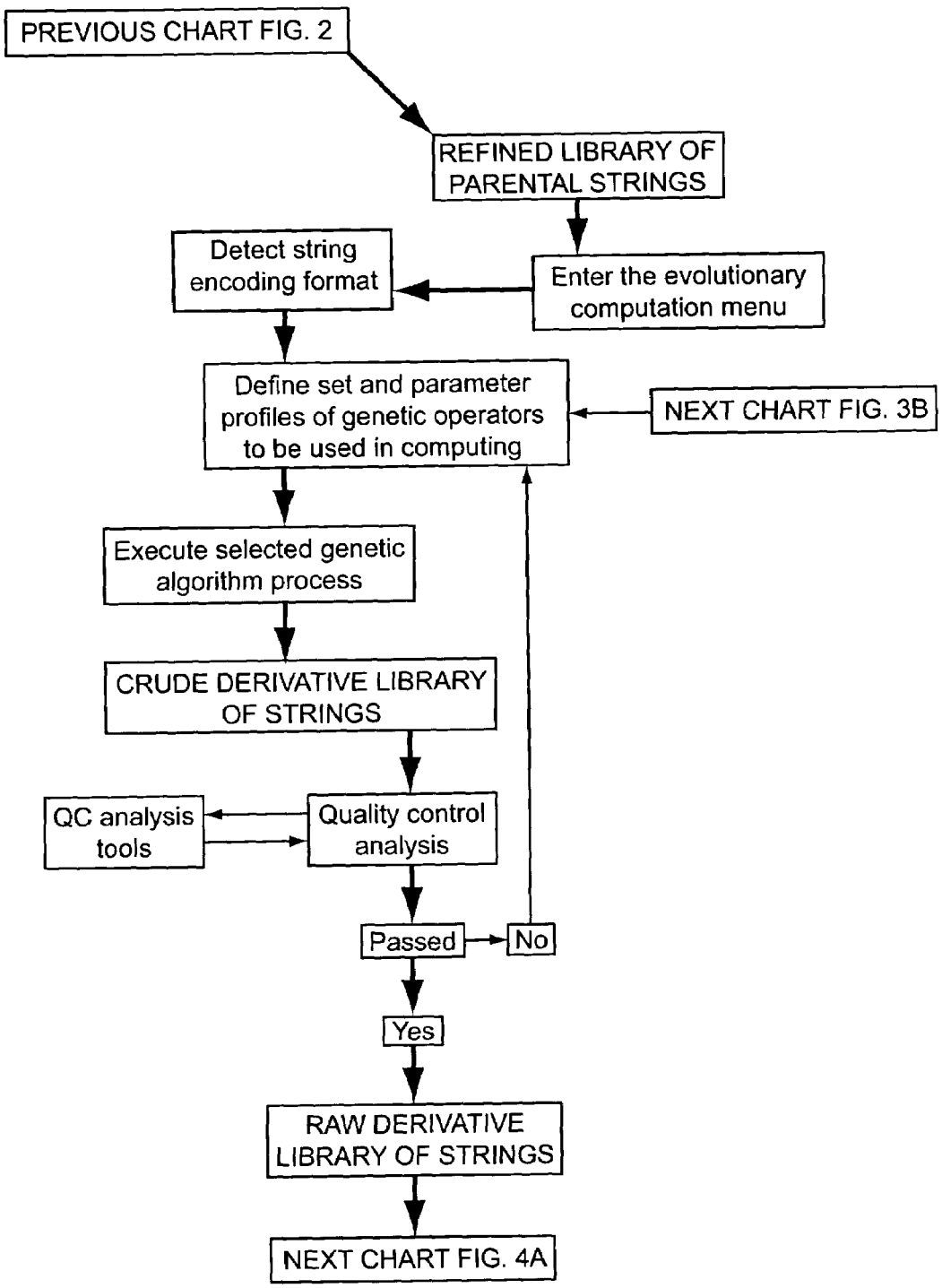
FIG. 3 is a flow chart describing a portion of directed evolution by GAGGS. The flow chart of FIG. 3 is optionally contiguous from FIG. 2.
Figure 3B:
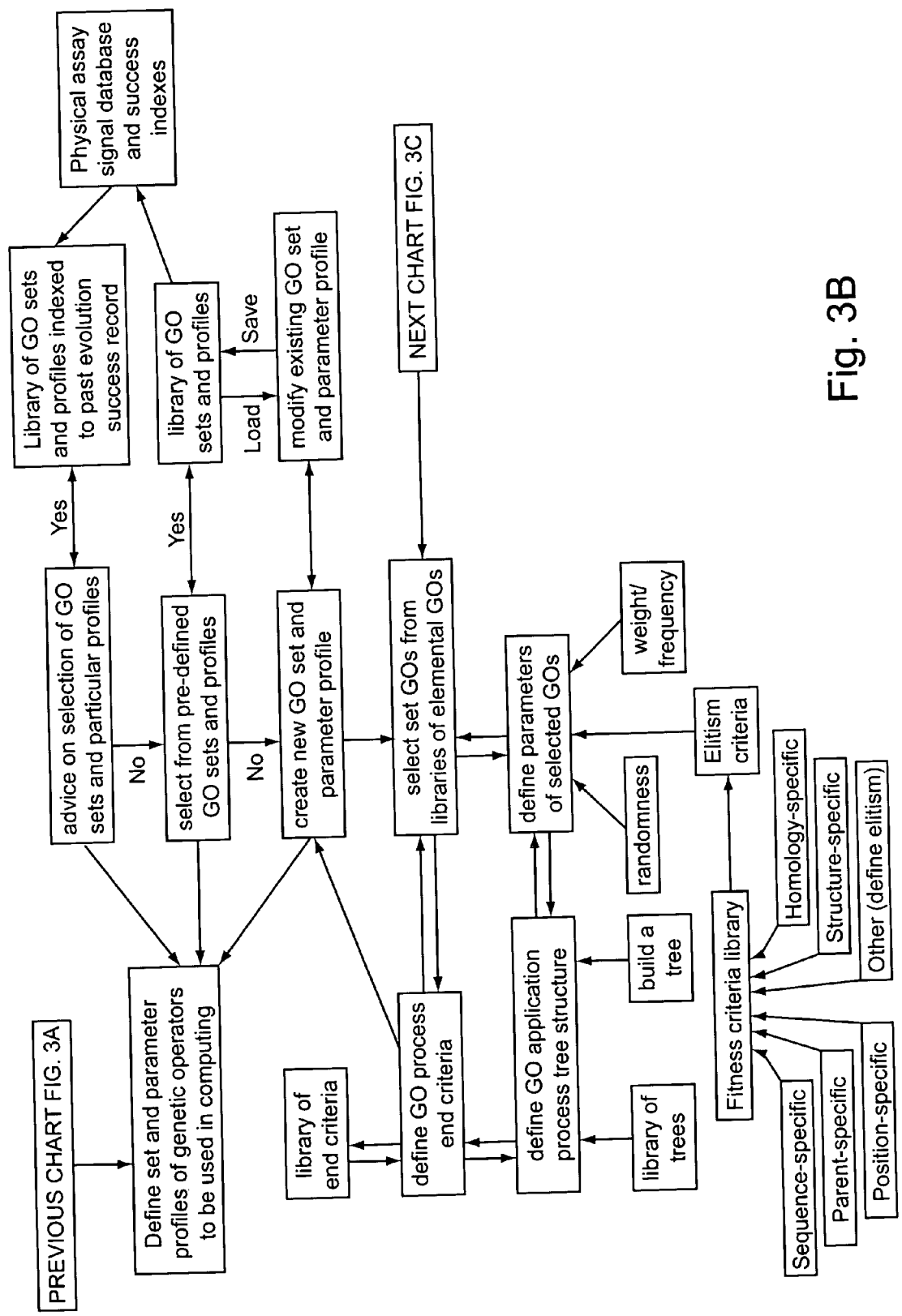
Figure 3C:
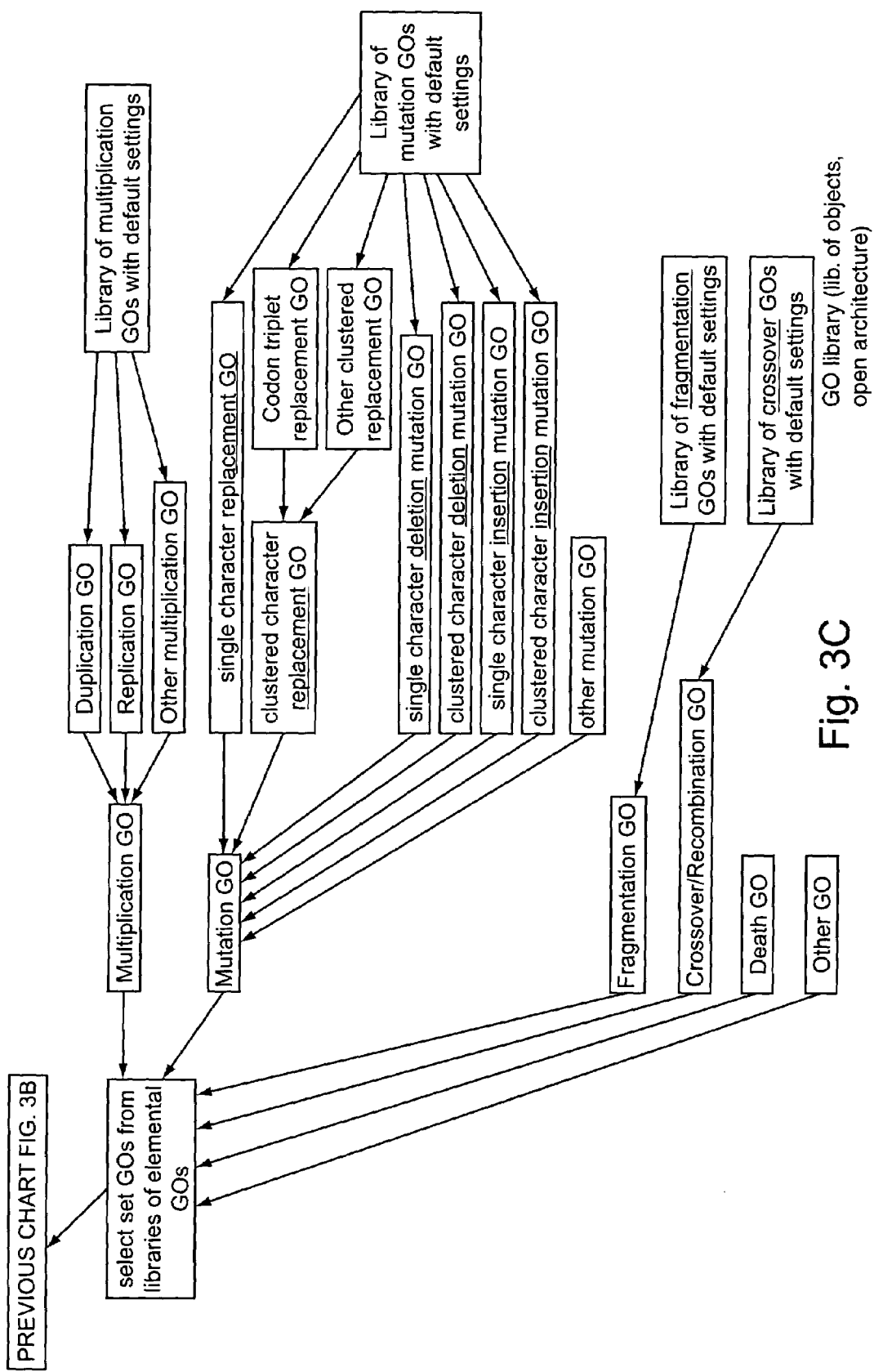
Figure 4A:
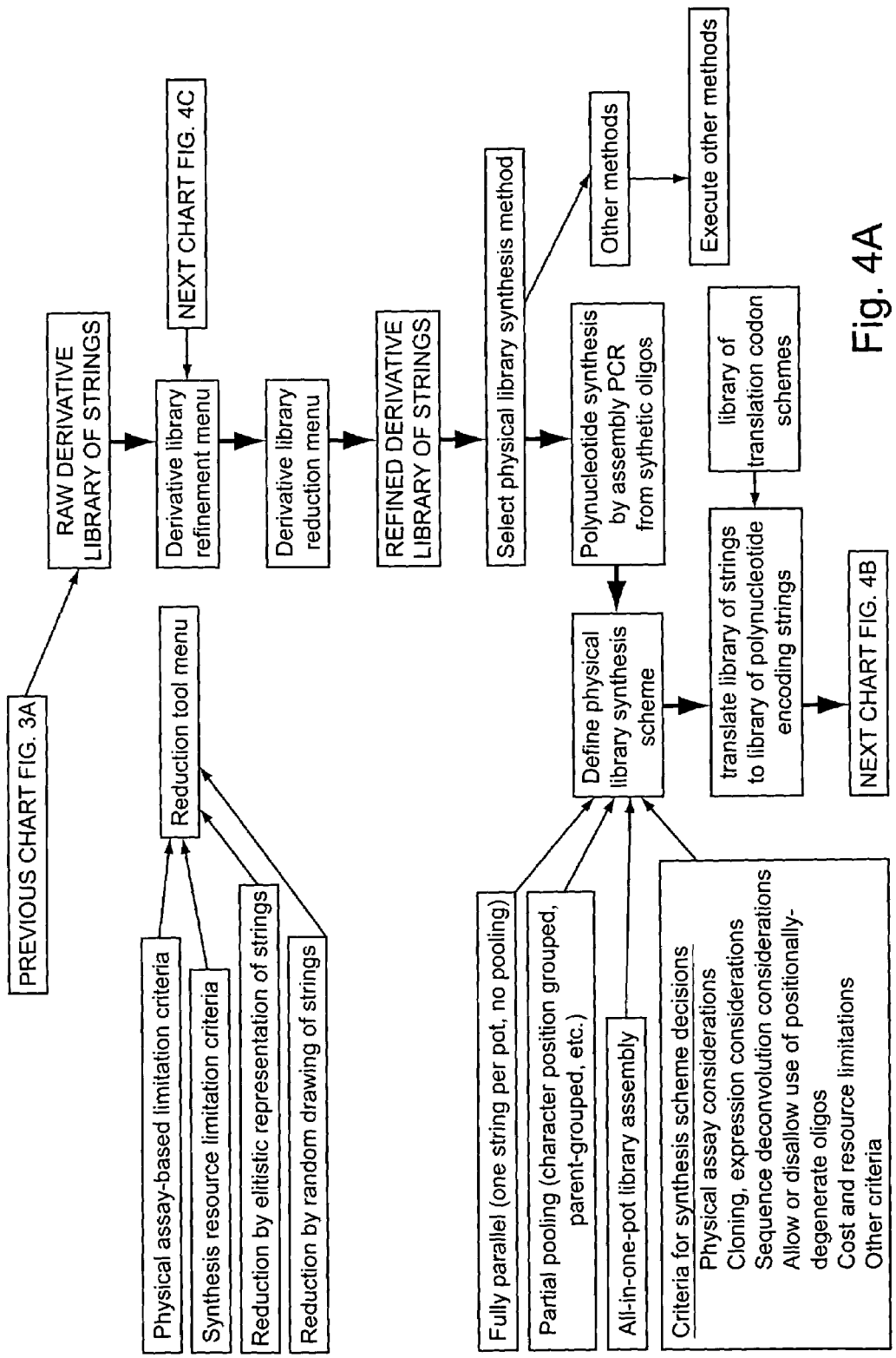
FIG. 4 is a flow chart describing a portion of directed evolution by GAGGS. The flow chart of FIG. 4 is optionally contiguous from FIG. 3.
Figure 4B:
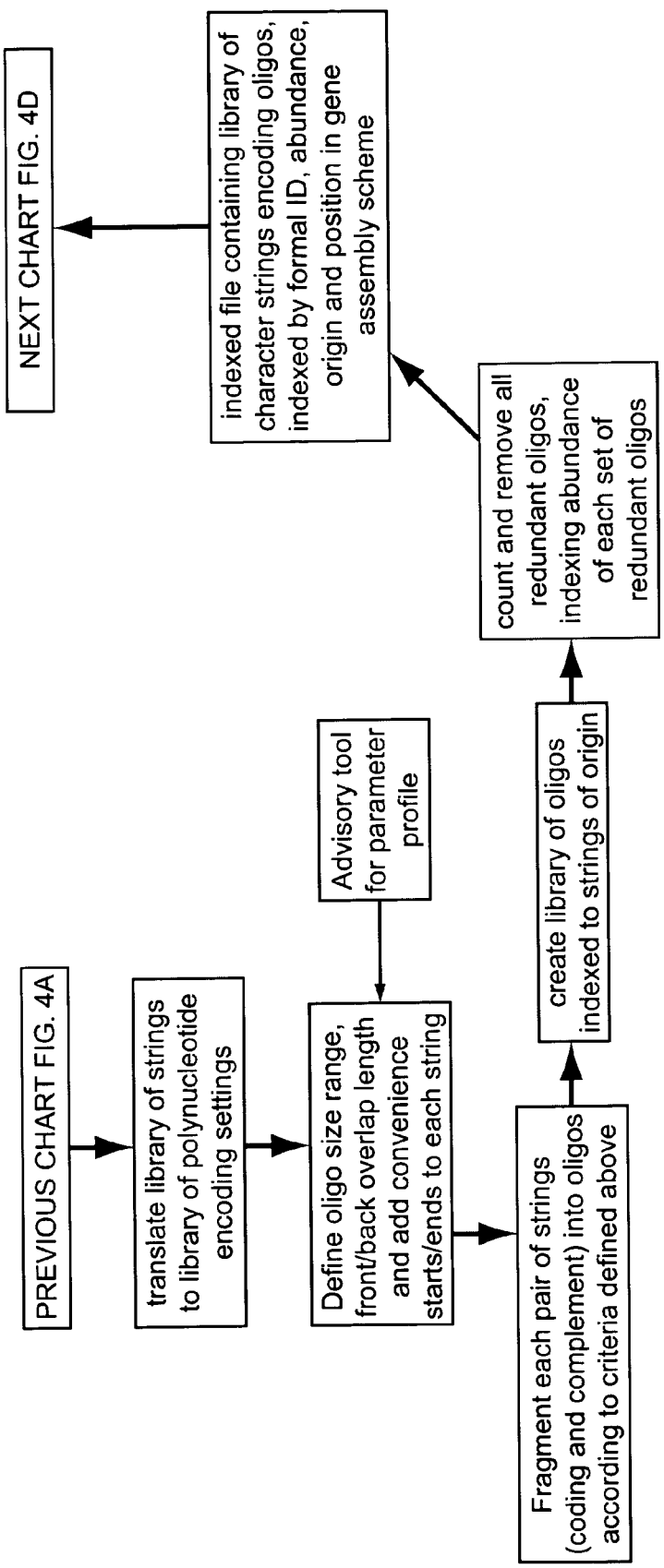
Figure 4C:
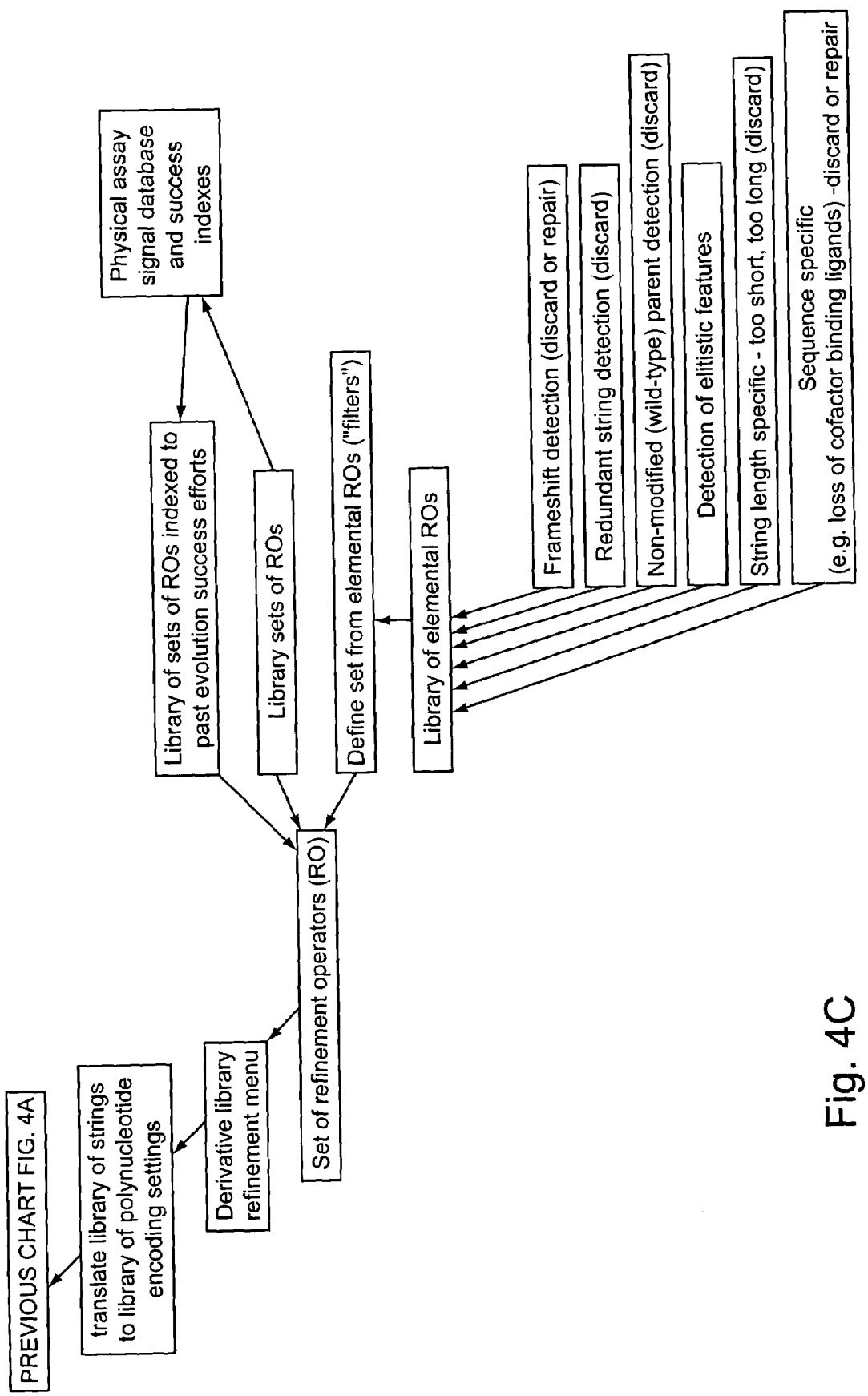
Figure 4D:
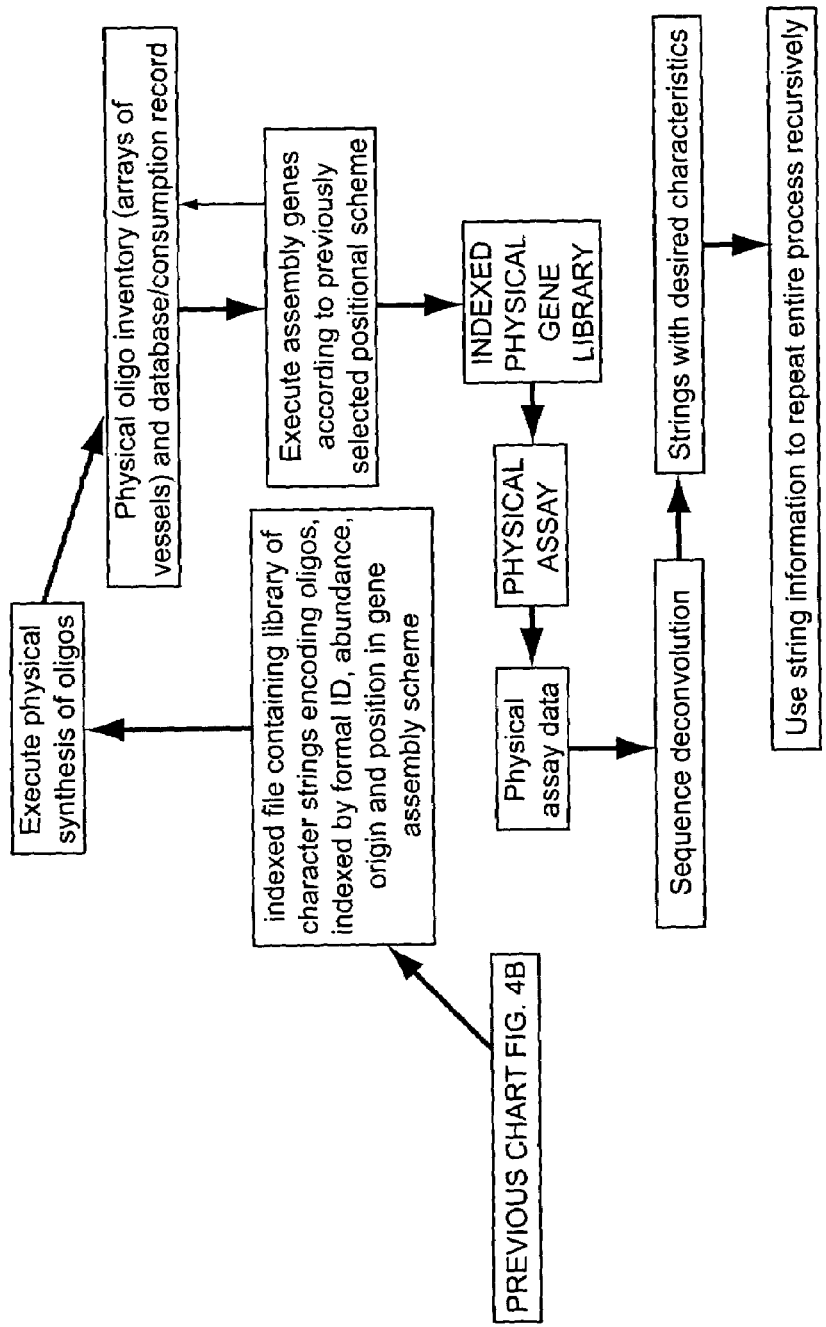

A set of flow schematics which provide a general representation of an exemplary process of Directed Evolution (DE) by GAGGS are enclosed (FIGS. 1–4). FIG. 1 provides an example decision making process from an idea of a desired property to selection of a genetic algorithm. FIG. 2 provides a directed evolution decision tree from selection of the genetic algorithm to a refined library of parental character strings. FIG. 3 provides example processing steps from the refined parental library to a raw derivative library of character strings. FIG. 4 processes the raw character strings to strings with a desired property.

Generally the charts are schematics of arrangements for components, and of process decision tree structures. It is apparent that many modifications of this particular arrangement for DEGAGGS, e.g., as set forth herein, can be developed and practiced. Certain quality control modules and links, as well as most of the generic artificial neural network learning components are omitted for clarity, but will be apparent to one of skill. The charts are in a continuous arrangement, each connectable head-to tail. Additional material and implementation of individual GO modules, and many arrangements of GOs in working sequences and trees, as used in GAGGS, are available in various software packages. Suitable references describing exemplar existing software are found, e.g., at [aic.nrl.navy.mil/galist/ (on the world wide web) and at cs.purdue.edu/coast/archive/clife/FAQ/www/Q20_2.htm (on the world wide web). It will be apparent that many of the decision steps represented in FIGS. 1–4 are performed most easily with the assistance of a computer, using one or more software program to facilitate selection/decision processes.

EXAMPLE 2

Modeling Cost Estimates

Use of degenerate synthetic oligos with very limited degree/low level of positional degeneracy (under 0.01–5% per position) can offer a very substantial cost saving in building those libraries which incorporate substantial mutagenicity. For PCR assembly gene synthesis, however, representation of all of the crossover events between parental entries uses synthesis of two dedicated oligos per simulated crossover event.

However, as will be apparent from the examples below and from the combinatorial nature of nucleic acid evolution algorithms, even building very large ($10^9$–$10^{10}$) gene libraries for physical screening uses less than $10^3$ individual 40-mer oligos for evolution of a family of typical genes of ~1.6 kb size.

Several typical examples below provide examples of costs of gene synthesis components in GAGGS, where the cost calculation is based arbitrarily at $0.7 per base (for a 40–50 nmol quantity, which is adequate for gene reassembly procedures) for exemplary purposes. Larger volume demand in oligo synthesis service leads to substantially lower unit cost (e.g., to a decrease of as much as 10 fold) and the general costs of oligo synthesis are in decline. Oligo synthesis is an inheritantly parallel and routine process easily amenable to automation and thus to increases in throughput. Currently, non-chip parallel devices for oligo synthesis provide an effective capacity to complete simultaneous (single-load) synthesis of 196 (2×96) individual 60-mer oligos in less than

EXAMPLE 3

GAGGS of a Single Parent Low Mutagenicity Library

This example describes GAGGS of a single parent low mutagenicity library derived from an average gene (~1.6 kb), given the sequence information of a single 1.6 kb gene (encoding 500 aa +"convenience" start/end oligos). The goal is to build a library of gene variants with all possible single amino acid changes, one aa change per each gene copy in the library.

Relevant parameters include the number of oligos and cost to build 1 parental 1.6 kb gene, e.g., from 40 mer oligos, with complete 20+20 base overlaps e.g., by non-error prone assembly PCR, the number of all possible single aa replacement mutations, the number of distinct non-degenerate 40-mer oligos used to "build-in" all possible single aa mutations, the minimal number of all distinct fixed-position single-codon-degenerate oligos used to incorporate all possible single aa mutations, but not terminations, and the minimal number of all distinct fixed-position single-codon-fully degenerate oligos used to incorporate all possible single aa mutations.

For a 1.6 kb gene, 1∞1,600: 40∞2=80 oligos; $0.7∞40–80=$2,240. N=500 19=9,500 9,500×2=19,000; $532,000 @ $0.7/base $56 per gene, 1 per pool 500×2×3=3,000; $84,000 @ 0.7/base, $8.85 per gene, 20 phenotypes per pool, normalized abundance (e.g. by using only three variable codons, two of which are degenerate: NNT, VAA, TGG) 500×2=1,000; $28,000 @0.7/base $2.94 per gene, 20 phenotypes per pool, skewed abundance (this results in the presence of significant numbers of truncated genes in the synthesized library).

The same physical oligo inventory used for the first round GAGGS is used in the second round of GAGGS to synthesize a library which contains ~95% of all possible combinations of any of two single aa changes. To have 100% coverage (to include for combinations of mutations within +/−20 bp proximity, additional oligos are used. Where at least one mutation from the previous round has been identified as beneficial, coverage of all combinations of new mutations within +/−20 bp of the beneficial mutations uses synthesis of no more than 42 new oligos). The cost of subsequent rounds of GAGGS grow only marginally, and linearly, while diversity sampled in a recursive mode grows exponentially.

EXAMPLE 4

GAGGS of Recombinogenic (Non-Mutagenic) Library Parented By a Family of Genes (GAGGS Equivalent of Single Round of Family DNA Shuffling)

Given sequence information for six fairly average (1.6 kb) size genes, each having six areas of homology with each of the other parental genes (six "heads" and "tails" for chimerizing each area of homology).

Relevant parameters include: the number of oligos and resulting cost to build 6 parental 1.6 kb genes (from 40 mer oligos, complete 20+20 overlaps, by non-error-prone assembly PCR), the number of distinct pairwise crossovers between all matching homology areas, assuming 1 crossover event per pairwise homology region), the number of all possible chimeras using the crossovers, the theoretical library size, and the number of distinct oligos and cost to build all possible chimeras. As above, 6 1,600: 40∞2=480 oligos, $0.7 ∞40∞480=$13,440, i.e., $2,240 per gene built. N=180, calculated according to the formula N=k∞m∞(m$^{-1}$), where m=6 number of parents, and k=6 is the number of pairwise homology areas satisfying crossover conditions. X=~5.315±10$^9$, calculated according to the formula:

$$X = \sum_{n=1}^{k} \{C_k^n \times m \times [m \times (m-1)]^n\}$$

where X is the theoretical library size and n is number of crossovers in each library entry (integer from 1 to k) 2–180+480=840 oligos; $0.7∞40–840=$23,520; $0.000048 per gene built. If only 10$^6$ are screened, then the cost of oligos is $0.024 per gene built; if only 10$^5$, then the cost of oligos is $0.24 per gene built, if 10$^4$ are screened then the cost of oligos is $2.35 per gene built.

The cost of running multiple rounds of GAGGS is not additive, as most of the excess oligos from previous rounds can be reused in synthesis of the later generation libraries.

Even if only a small fraction of all genes built is actually screened (e.g. 10$^4$, with cost of oligos $2.35 per gene built), the oligo expenses are comparable with cost of assays on per gene-assay basis. In addition, industry wide oligo synthesis costs are declining.

EXAMPLE 5

Stepwise GAGGS

This example provides a GAGGS family model stepwise protocol. A family of genes/proteins (DNA or AA sequence) is selected. All possible pairwise alignments are made to identify pairwise homology regions satisfying crossover operator conditions (length, % identity, stringency). Crossover points are selected, one per each of the pairwise homology substrings, in the middle of each substring, or randomly, or according to an annealing-based probability model built on histograms of crossover probability ranks for every pair of parents. Oligos are selected for assembly PCR and synthesized. Genes/libraries are assembled from synthesized oligos. The libraries are screened/selected as set forth above.

EXAMPLE 6

Subtilisin Family Model

Figures 5A, 5B:
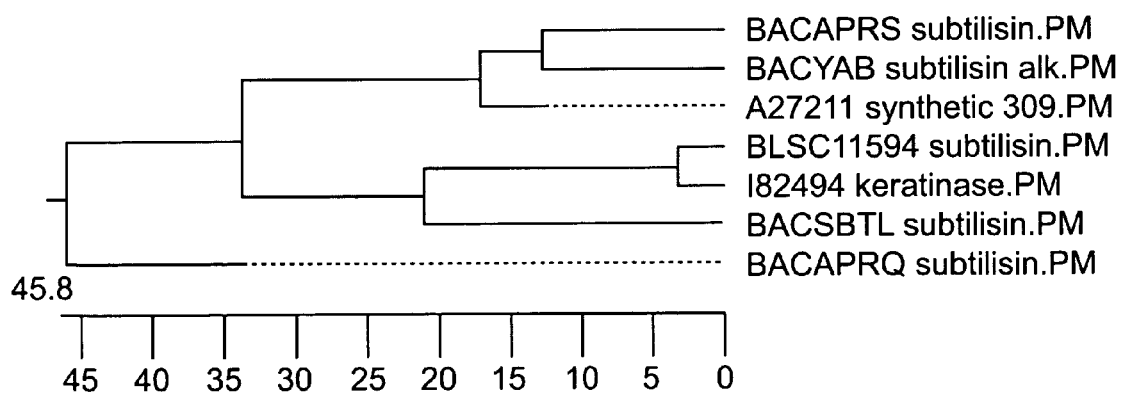
FIG. 5 is a chart and relational tree showing percent similarity for different subtilisins (an exemplar shuffling target).
Figure 6:
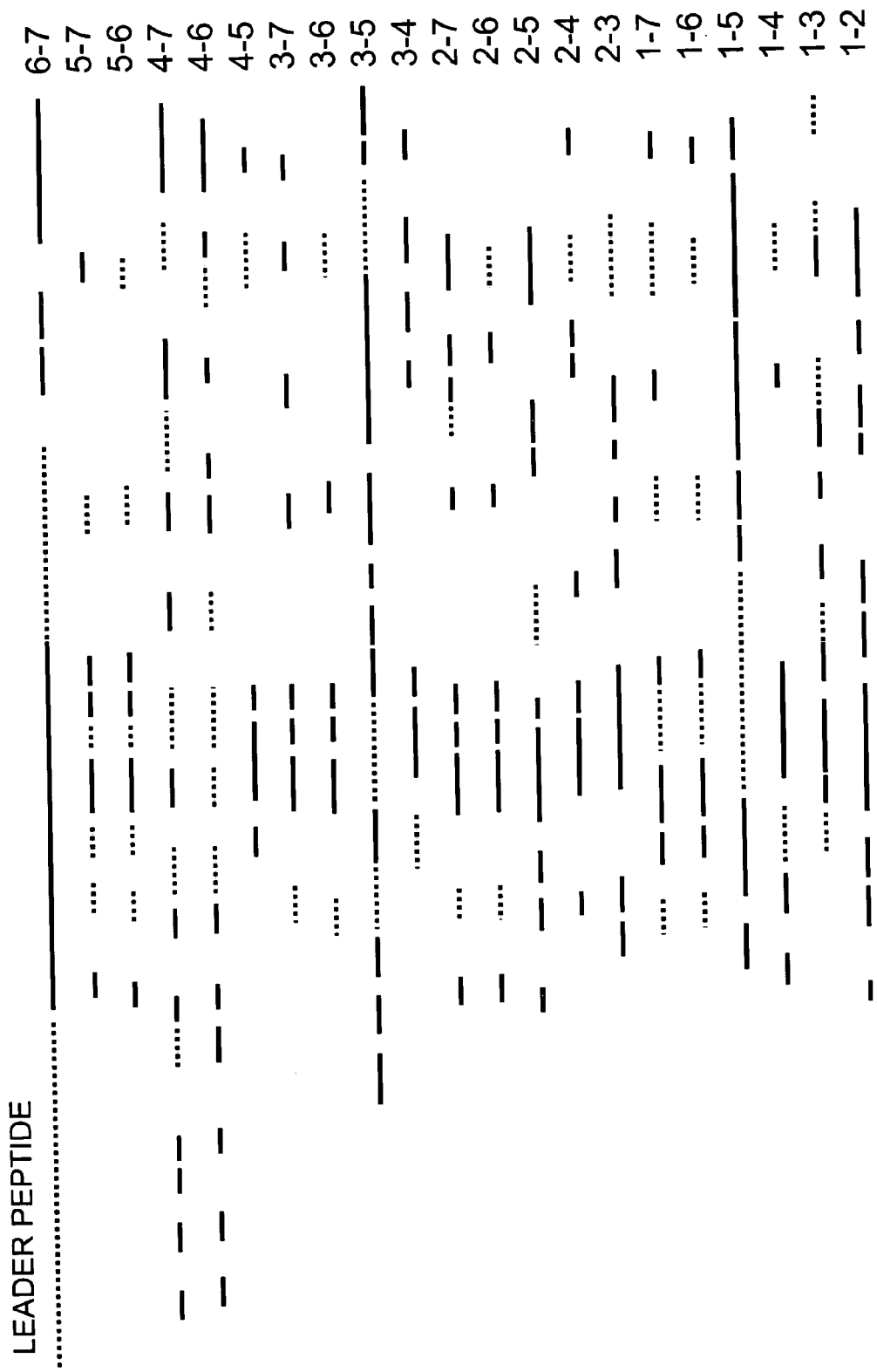
FIG. 6 is a pairwise dot-plot alignment showing homology areas for different subtilisins.
Figure 7:
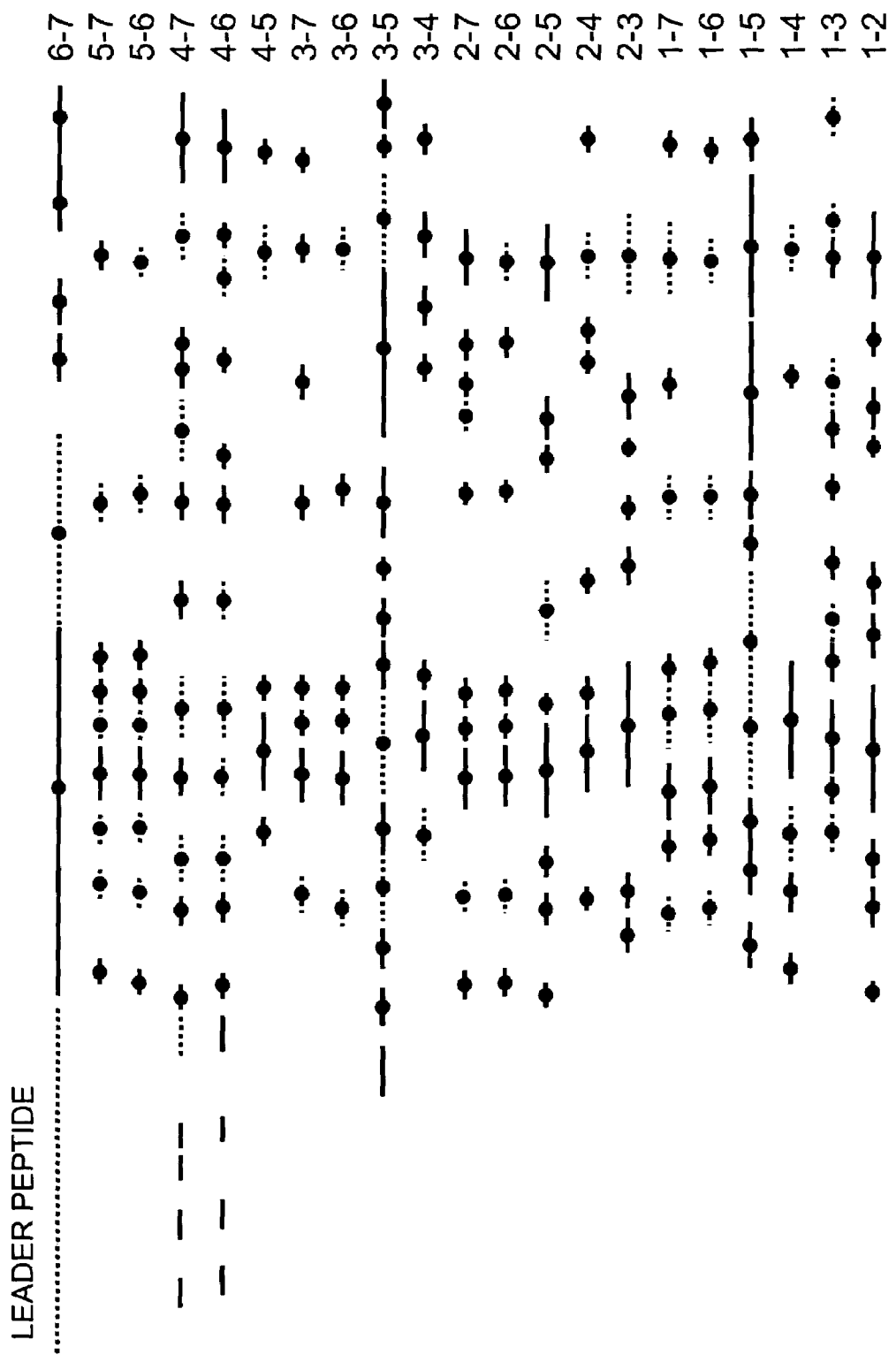
FIG. 7 is a pairwise dot-plot alignment showing homology areas for 7 different parental subtilisins.

Amino acid sequences were aligned (Codon usage can be optimized on retrotranslation for a preferred expression system, and number of oligos for synthesis can be minimized). A Dot plot pairwise alignment of all possible pairs of 7 parents was made (FIGS. 5, 6, 7). FIG. 5 is a percent similarity alignment for 7 parents. Amino acid sequences are aligned, with the leader peptide excluded. FIG. 6 is a dot-plot alignment of the sequences to identify regions of similarity. FIG. 7 is a dot plot showing pairwise crossover points in the alignment.

Pair 6 and 7 show 95% percent identity per each window of ≧7aa, while all other pairs show 80% percent identity per each window of ≧7aa. Note that the stringency of alignment (and subsequent representation of crossover between parents) can be manipulated individually for each pair, so that low homology crossovers can be represented at the expense of highly homologous parents. No structural biases or active site biases were incorporated in this model.

As an example GAGGS calculation for the subtilisin family model, assuming 7 parents, of about 400 amino acids, and 1200 bp each (including the leader) or about 275 amino acids and 825 bp for mature protein, 7×825×2+about 500=12 kb of total sequence to be generated by gene synthesis. From 40 mers, with full overlap assembly (20+20 bp overlaps), about 300 oligos are used.

For pairwise crossover oligos to build chimeras, based on alignment results, with one crossover per each homologous substring, there are about 180 homologous substrings, with 170 in the coding region and 10 in the leader region. With 2 60 mers per each crossover point, and 2 head-tail sets for each pair of parents, about 360 additional oligos dedicated to build crossovers can be used. The total number of oligos is about 660 (300 40 mers and 360 60 mers). At a total cost of oligos of $0.70 per base, the oligos would be about $23,520. The cost of reagents would run about $0.07 per base, for a total cost of about $2,252 dollars.

EXAMPLE 7

Napthalene Dioxygenase

Figures 12A, 12B:
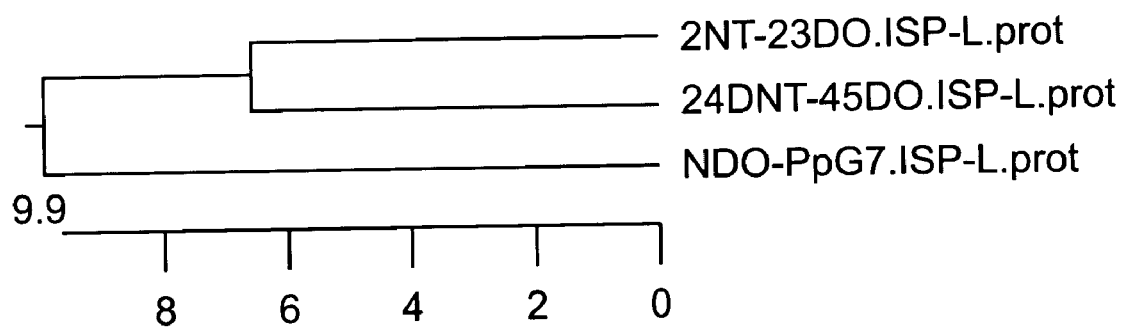
FIG. 12 is a difference plot and relatedness tree for shuffling Naphthalene deoxygenase.

Napthalene dioxygenase is a non-heme reductive dioxygenase. There are at least IR three closely related but catalytically distinct types of Napthalene dioxygenases. FIG. 12 provides a schematic of a percent similarity plot for the three different Napthalene dioxygenase types, with the amino acid sequence for the ISP large subunit (which is responsible for substrate specificity) being provided.

At a size of about 1,400 amino acids, there are 3×1,400 total base pairs=260 40 E mer oligos for 20+20 overlap gene synthesis. A plot of the sequence alignment reveals that there are 14+19+23=112 60 mer high stringency oligos used in the recombination. The cost of oligos at $0.70 per base would yield a cost of about $12,000 for synthesis, using about 9 hours of synthesizer time to make the oligos. The estimated library size would be about $9.4 \times 10^9$ chimeras.

EXAMPLE 8

Single Parent GAGGS Calculation

As noted above, one aspect of the invention provides for single parent GAGGS. In these methods, polynucleotides having desired characteristics are provided. This is accomplished by: (a) providing a parental sequence character string encoding a polynucleotide or polypeptide; (b) providing a set of character strings of a pre-defined length that encode single-stranded oligonucleotide sequences comprising overlapping sequence fragments of an entire parental character string, and an entire polynucleotide strand complementary to the parental character string (splitting the sequence of a parent into oligos suitable for assembly PCR); (c) creating a set of derivatives of parental sequence comprising variants with all possible single point mutations, with, e.g., one mutation per variant string (defining all possible single point mutations); (d) providing a set of overlapping character strings of a pre-defined length that encode both strands of the parental oligonucleotide sequence, and a set of overlapping character strings of a pre-defined length that encode sequence areas including the mutations (oligos incorporating single point mutations, suitable for the same assembly PCR scheme); (e) synthesizing sets of single-stranded oligonucleotides according to the step (c) (e.g., to build or rebuild the parental sequence or a variant thereof e.g., incorporating single point mutations during gene assembly); (f) assembling a library of mutated genes in assembly PCR from the single-stranded oligonucleotides (pooling, partial pooling, or one per container).

For one gene per container approaches (or other approaches involving physically separating library components, e.g., in arrays), wild type oligos are excluded at mutations; and (g) selecting or screening for recombinant polynucleotides having evolved toward a desired property. In an additional optional step (h), the method includes deconvoluting sequence of the mutated polynuceotides (i.e., determining which library member has a sequence of interest, and what that sequence is) having evolved toward a desired property to determine beneficial mutations (when assembly PCR is one per container format, this is done by positional sequence deconvolution, rather than actual sequencing, i.e., the physical location of the components are adequate to provide knowledge of the sequence). In an optional additional step (i), the method includes assembling a library of recombinant variants which combine some or all possible beneficial mutations in some or all possible combinations, from single-stranded oligos by assembly PCR. This is performed from the same set of oligos; if some of the mutations are positionally close (within any one oligo), then additional single strand oligos are made which incorporate combinations of mutations. An optional step 0) includes selecting or screening for recombinant polynucleotides having evolved further toward a desired property.

An example single parent GAGGS calculation, per 1 kb of sequence follows.

Genome length: 1000 bp.

First round mutation rate: 1 amino acid/gene.

Number of oligonucleotides to build wild-type gene: 52 (40 mers, 20+20 overlap synthesis scheme).

Number of oligonucleotide to provide for all possible single point non-terminating mutations (333 total possible): non degenerate oligos: 13320. Partially degenerate 40 mers, one pg position per oligo: 1920. Fully degenerate oligos, 40 mers, one fg position per oligo: 666.

Error prone PCR assembly will also work, but sequence deconvolution is performed, e.g., by sequencing before subsequent rounds.

The number of additional oligos to allow for construction of all possible recombinations with beneficial mutations would use about 10% of the preceding number of oligos. However, about 95% of all possible recombinants having beneficial mutations can be made from the initial set produced above.

EXAMPLE 9

A Process for Design of Crossover Oligonucleotides for Synthesis of Chimerical Polynucleotides First, substrings are identified and selected in parental strings for applying a crossover operator to from chimeric junctions. This is performed by: a) identifying all or part of the pairwise homology regions between all parental character strings, b) selecting all or part of the identified pairwise homology regions for indexing at least one crossover point within each of the selected pairwise homology regions, c)

selecting one or more of the pairwise non-homology regions for indexing at least one crossover point within each of the selected pairwise non-homology regions ("c" is an optional step which can be omitted, and is also a step where structure-activity based elitism can be applied), thereby providing a description of a set of positionally and parent-indexed regions/areas (substrings) of parental character strings suitable for further selection of crossover points.

Secondly, further selection of crossover points within each of the substrings of the set of the substrings selected in step 1 above is performed. The steps include: a) randomly selecting at least one of the crossover points in each of the selected substrings, and/or b) selecting at least one of the crossover points in each of the selected substrings, using one or more of annealing-simulation-based models for determining probability of the crossover point selection within each of the selected substrings and/or c) selecting one crossover point approximately in the middle of each of the selected substrings, thereby creating a set of pairwise crossover points, where each point is indexed to corresponding character positions in each of the parental strings desired to from a chimeric junction at that point.

Thirdly, optional codon usage adjustments are performed. Depending on methods used to determine homology (strings encoding DNA or AA), the process can be varied. For example, if a DNA sequences was used: a) adjustment of codons for the selected expression system is performed for every parental string, and b) adjustment of codons among parents can be performed to standardize codon usage for every given aa at every corresponding position. This process can significantly decrease total number of distinct oligos for gene library synthesis, and may be particularly beneficial for cases where AA homology is higher than DNA homology, or with families of highly homologous genes (e.g. 80%+identical).

This option has to be exercised with caution, as it is in essence an expression of an elitism mutation operator. Thus, one considers the benefits of cutting the number and resulting costs of oligos vs. introduction of this bias, which can have undesirable consequences. Most typically, one uses codons which encode AA at a given position in a majority of parents.

If AA sequences are used: a) retrotranslate sequence to degenerate DNA; b) define degenerate nucleotides using position-by-position referencing to codon usage in original DNA (of majority of parents or of corresponding parent), and/or—exercise codon adjustments suitable for the selected expression system where a physical assay will be performed.

This step can also be used to introduce any restriction sites within coding parts of the genes, if any, for subsequent identification/QA/deconvolution/manipulations of library entries. All crossover points identified in step 2 above (indexed to pairs of parents) are correspondingly indexed to the adjusted DNA sequences.

Fourth, oligo arrangements are selected for a gene assembly scheme. This step includes several decision steps:

Uniform 40–60 mer oligos are typically used (using longer oligos will result in decrease of # of oligos to build parents, but uses additional dedicated oligos for providing representation of closely positioned crossovers/mutations.

Select whether Shorter/Longer Oligos are allowed (i.e., a Yes/No decision). A "Yes" decision cuts the total number of oligos for high homology genes of different lengths with gaps (deletion/insertion), esp for 1–2aa.

Select the overlap length (typically 15–20 bases, which can be symmetrical or asymmetrical).

Select whether degenerate oligos are allowed (Yes/No). This is another potent cost cutting feature and also a powerful means to obtain additional sequence diversity. Partial degeneracy schemes and minimized degeneracy schemes are especially beneficial in building mutagenic libraries.

If software tools are used for these operations, several variations of the parameters are run to select maximum library complexity and minimal cost. Exercising complex assembly schemes using oligos of various length significantly complicates indexing processes and, AI subsequently, assembly of the library in positionally encoded parallel or partial pooling formats. If this is done without sophisticated software, a simple and uniform scheme (e.g. all oligos 40 bases long with 20 bases overlap) can be used.

Fifth, "convenience sequences" are designed in front and in the back of the parent strings. Ideally, it is the same set which will be built in every library entry at the end. These include any restriction sites, primer sequences for assembled product identifications, RBS, leader peptides and other special or desirable features. In principle, the convenience sequences can be defined at a later stage, and at this stage, a "dummy" set of appropriate length can be used, e.g. a substring from an easily recognizable forbidden letters.

Sixth, an indexed matrix of oligo strings for building every parent is created, according to the selected scheme. An index of every oligo includes: a parent identifier (parentID), indication of coding or complementary chain, and position numbers. Crossover-points are determined for indexed coding string of every parent with head and tail convenience substrings. A complementary chain of every string is generated. Every coding string is selected according to the selected assembly PCR scheme in step 4 above (e.g. in increments of 40 bp). Every complement string is split according to the same scheme (e.g. 40 bp with 20 bp shift)

Seventh, an indexed matrix of oligos is created for every pairwise crossover operation. First, all oligos which have pairwise crossover markers are determined. Second, all sets of all oligos which have the same position and same pair of parents crossover markers (4 per crossover point) are determined. Third, every set of 4 oligo strings are taken which have been labeled with the same crossover marker, and another derivative set of 4 chimeric oligo strings comprising of characters encoding 2 coding and 2 complement chains (e.g. with 20 bp shift in 40=20+20 scheme) are made. Two coding strings are possible, having a forward end sequence substring of one parent followed by the backward end of the second parent after crossover point. Complement strings are also designed in the same fashion, thereby obtaining an indexed complete inventory of strings encoding oligos suitable for gene library assembly by PCR.

This inventory can further be optionally refined by detecting all redundant oligos, counting them and deleting from inventory, accompanied by the introduction of the count value to an "abundance=amount" field in the index of each oligo string. This may be a very beneficial step for reducing total number of oligos for library synthesis, particularly in the cases if parental sequences are highly homologous.

EXAMPLE 10

Program Algorithm for Designing Oligonucleotides for Synthesis

The following is a program outline for designing oligonucleotides for use in synthetic/recombination protocols. Given an alignment of proteins and a codon bias table:
For each position in an alignment of proteins find a set of minimally degenerate codons that code for
    Amino Acids at this position using codon bias table
For each sequence in alignment
    Add three letter codon (DNA) that codes for the amino
        acid at this position in this sequence to DNA version
        of sequence
    !Gaps are represent by a special codon—
for each sequence of DNA created by above
    !Note gaps are ignored in this step
    For each window=rough oligo size
        check end degeneracy
            Try to increase and decrease window length to mini-
                mize end degeneracy while staying within length
                bounds
            add oligos given window bounds and all sequences
            add oligos given reverse window bounds and all
                sequences
    for each position in dnaseqs
        for each sequence
            If the current position is the start of a gap
                Add oligos given bounds which contains a minimum
                    amount of sequence from current sequence 5' of
                    the gap and a minimum amount of sequence from
                    current sequence 3' of the gap
                Repeat add oligos for reverse bounds
add Oligos: given a list of sequences (DNA) and bounds
    for each position in the bounds
        get all unique bases at this position from DNA
            sequences in the list
        generate a base (or degenerate base symbol) for this
            position
    if total degenerate positions is greater than user defined
        number
        split sequence list in two, add Oligos given sequence
            list one, add Oligos given
sequence list two (recursive)
    else add this oligo (set of bases for each position) to oligo
        list display all oligo in oligo list

EXAMPLE 11

Crossover Point Selection

Figure 8:
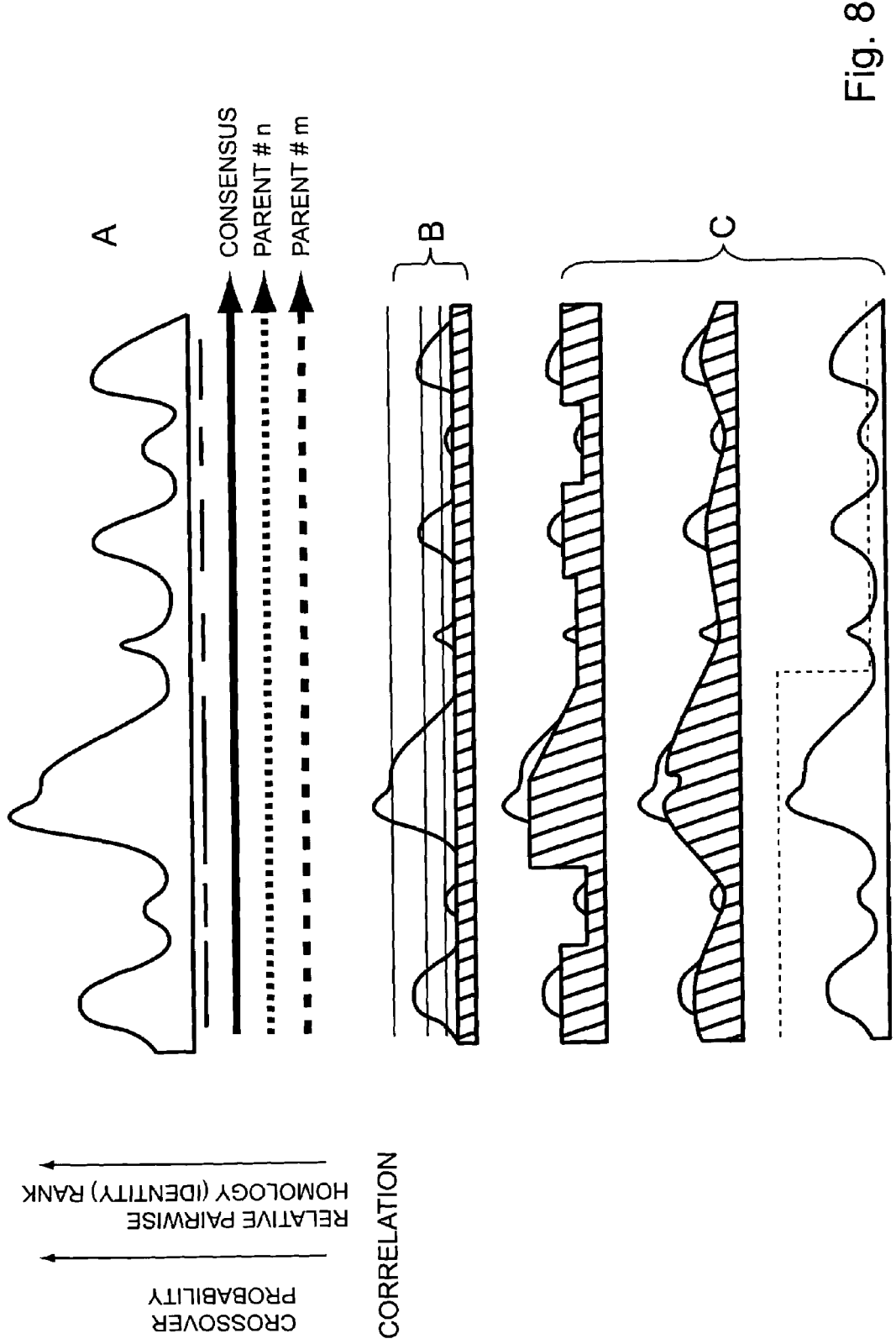
FIG. 8, Panels A–C are pairwise histograms showing conditions determining probability of crossover point selection can be independently controlled for any region over a selected gene length, as well as independently for the pairs of parents.

FIGS. 8–11 are schematics of various processes and process criteria for oligonucleotide selection for recombination between parental nucleic acids. FIG. 8, panel A shows a typical dot-plot alignment of two parents and the increase in crossover probability that results in regions of similarity. Panel B shows that crossovers can be selected based upon a simple logical/physical filter, i.e., the physical or virtual annealing temperature of oligonucleotides, e.g., using a linear annealing temperature. Panel C shows various more complex filters which vary annealing temperature to achieve specific crossovers, i.e., by appropriately controlling the physical or virtual annealing temperature.

Figure 10:
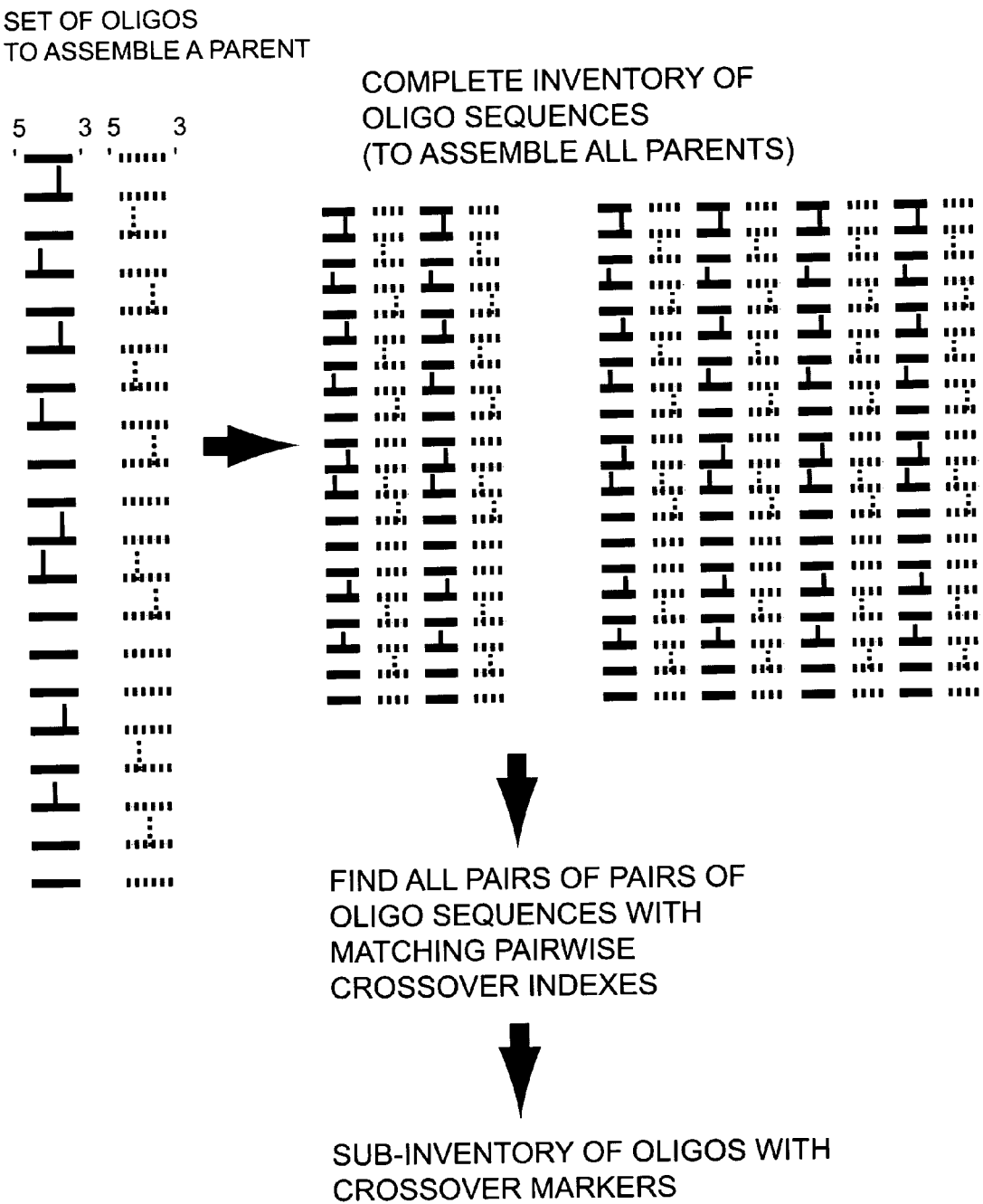
FIG. 10 shows a procedure for oligonucleotide assembly to make nucleic acids.
Figure 11:
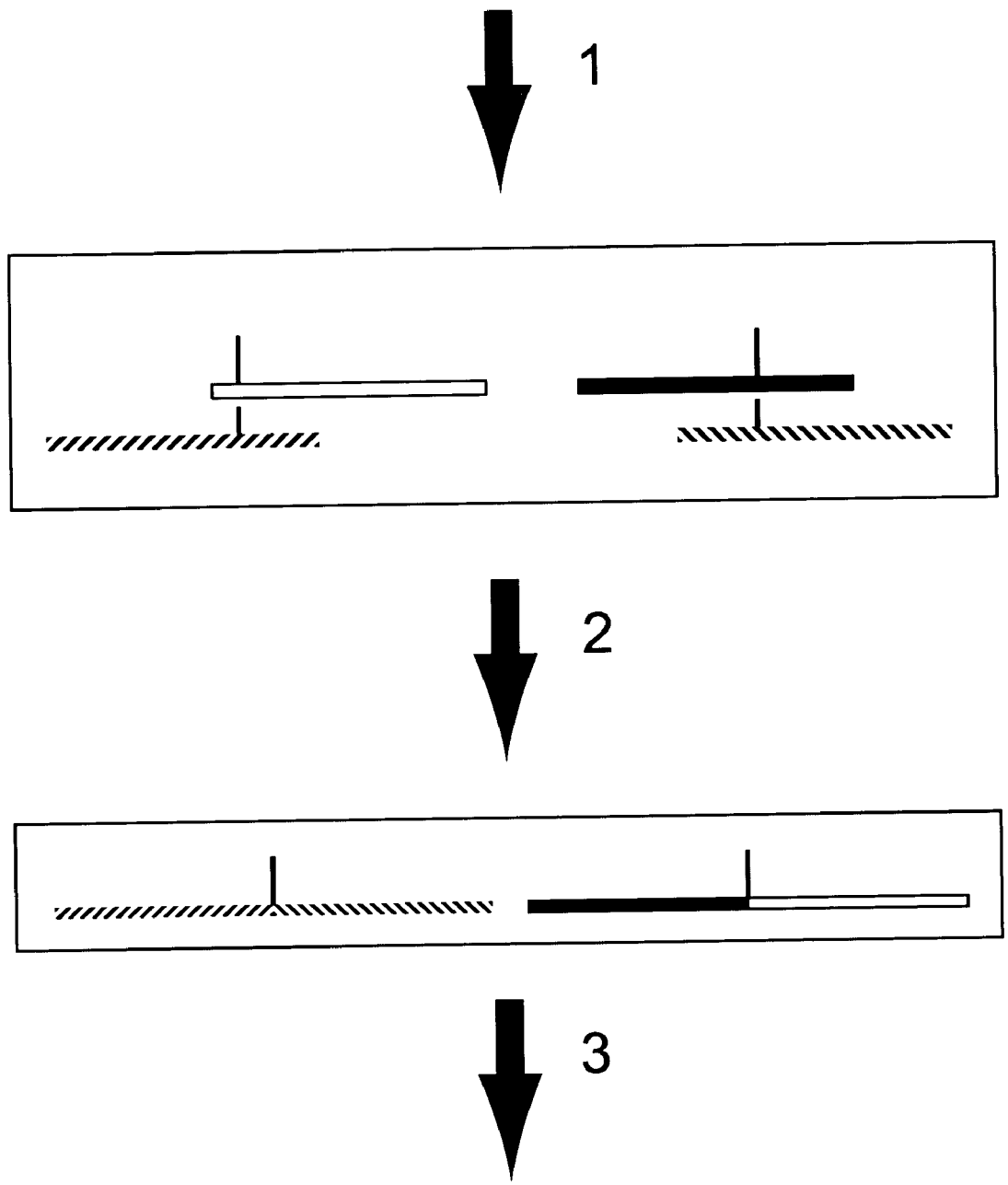
FIG. 11 is a continuation of FIG. 13 showing an oligonucleotide assembly scheme.

FIG. 9 schematically represents the introduction of indexed crossover points into the sequence of each of the aligned parents. In brief, sequences are aligned and the positional index of each crossover point (marker field) is represented schematically by a vertical identifier mark. The crossover point, for parents m and n, as represented in FIG. 8, is represented by an identifier, a position number for parent m (a head) and a position number for parent n (a tail). This process is repeated for every parent in a data set, applying the oligonucleotide gridding operator (grid of positional indexes which indicate the start and end of every oligonucleotide in a PCR assembly operation) to each of the parents. FIG. 10 schematically represents the complete inventory of oligonucleotide sequences to assemble all of the parents. The data set is simplified by identifying all pairs of oligonucleotide sequences with matching pairwise crossover indexes, providing a sub inventory of oligos with crossover markers. FIG. 11 provides a schematic for obtaining an inventory of sequences for chimeric oligonucleotides for each of the selected crossover points. In brief, two pairs of oligo sequences with matching pairwise crossover indexes are selected (down arrow 1). Sequences of chimeric oligonucleotides are generated around the to pairwise crossover point (head-tail, tail-head, s or a chain) (down arrow 2). In a "40=20+20" assembly scheme (where a 40mer has 20 residues from each parent), only one oligo longer than 60 bp. is used for each chimerization (two for each crossover point, regardless of relative positions within each oligo). This empirical finding can be described by variations of cut and join operations at the depicted S or A chains (e.g., as in FIG. 8), with the rule being reduced to a guidance table. In the chimeric oligos, the A or S chain and sequence head and tail subfragments are defined using a selected subset of rules from the guidance table. Selection or rules from the guidance table can be automated based upon comparison of relative positions of crossover points in the oligos (boolean operations) (down arrow 3). This process is repeated for every set of oligos with identical crossover indexes to obtain an inventory of sequences for chimeric oligos for each of the selected crossover points.

EXAMPLE 12

Synthetic Shuffling by Repeated Cycles of Melting, Annealing and Polymerization

The methods herein provide, inter alia, synthetic shuffling using, e.g., a primerless PCR reaction to assemble a series of overlapping oligos designed to capture the diversity represented in a family of related sequences. For example, the process provides family shuffling, without needing access to starting parental sequences-synthetic shuffling provides a direct route from an in silico database to shuffled library. See also, "OLIGONUCLEOTIDE MEDIATED NUCLEIC ACID RECOMBINATION" by Crameri et al., Filed Jan. 18, 2000, USSN PCT/US00/01203. Synthetic shuffling projects are not limited to natural diversity, and need not result in equal representation of diversity, and diversity can occur with any desired granularity of diversity (e.g., at the level of single amino acids, or in blocks, depending on the sequences that are selected). Freedom of oligo sequence, length, and number; as well as freedom to mix oligos in any desired combination and quantities under any desired assembly parameters allows great control over library design.

One example is the synthetic shuffling of subtilisins, also described supra. In one example 16 overlapping 60-mers (8 top strand and 8 bottom strand) with 20 bp of homology between ends of top and bottom strand oligos formed a backbone were designed to capture the majority of natural diversity represented in a 660 bp gene segment (also known as the diversified region) of a family of 15 subtilisin sequences. The diversity was largely captured by introducing degeneracies into the oligonucleotide backbone. Diversity that was not captured in the backbone oligos was encoded in 11 additional 39- to 45-mers. In addition to capturing the diversity represented in the 15 subtilisin sequences, the backbone and spiking oligos optimized codon usage for *Bacillus subtilis* and maximized recombination. Oligos were mixed at equimolar concentrations and assembled in a primerless PCR reaction. A full-length library was rescued from the assembly by conventional PCR with primers annealing to construct ends. The library was designed such that it recombines at the level of single amino acids and results in equal representation of all possible amino acids in a particular position (assuming unbiased assembly and equal representation of nucleotides at degenerate positions). This is in contrast to recombination by simple fragmentation and reassembly, which typically shuffles in blocks and can result in biased representation of encoded amino acids, based on occurrence of a particular amino acid in the starting parental sequences.

Modifications can be made to the methods and materials as hereinbefore described without departing from the spirit or scope of the invention as claimed, and the invention can be put to a number of different uses, including:

The use of an integrated system to generate shuffled nucleic acids and/or to test shuffled nucleic acids, including in an iterative process.

An assay, kit or system utilizing a use of any one of the selection strategies, materials, components, methods or substrates hereinbefore described. Kits will optionally additionally comprise instructions for performing methods or assays, packaging materials, one or more containers which contain assay, device or system components, or the like.

In an additional aspect, the present invention provides kits embodying the methods and apparatus herein. Kits of the invention optionally comprise one or more of the following: (1) a shuffled component as described herein; (2) instructions for practicing the methods described herein, and/or for operating the selection procedure herein; (3) one or more assay component; (4) a container for holding nucleic acids or enzymes, other nucleic acids, transgneic plants, animals, cells, or the like, (5) packaging materials, and (6) software for performing any of the decision steps noted herein related to GAGGS.

In a further aspect, the present invention provides for the use of any component or kit herein, for the practice of any method or assay herein, and/or for the use of any apparatus or kit to practice any assay or method herein.

The previous examples are illustrative and not limiting. One of skill will recognize a variety of non-critical parameters which may be altered to achieve essentially similar results. All patents, applications and publications cited herein are incorporated by reference in their entirety for all purposes.

What is claimed is:

1. A method of identifying a set of oligonucleotides for use in an in vitro recombination procedure, the method comprising:
    (a) providing data identifying sequences of two or more parental polypeptides or parental nucleic acids that encode the polypeptides;
    (b) computationally selecting one or more cross-over sites on the sequences based on structural information about the parental polypeptides or polypeptides encoded by the parental nucleic acids; thereby defining one or more recombinant polypeptides or recombinant nucleic acids that result from cross-overs between the parental polypeptides or nucleic acids at the one or more cross-over sites;
    (c) selecting at least one of the recombinant polypeptides or recombinant nucleic acids by computationally assessing structural stability of at least some of the recombinant polypeptides or polypeptides encoded by the recombinant nucleic acids; and
    (d) computationally identifying one or more oligonucleotides for in vitro recombination by choosing at least one portion of at least one of the recombinant polypeptides or recombinant nucleic acids selected in (c) which at least one portion corresponds to the one or more oligonucleotides identified for in vitro recombination.

2. The method of claim 1, wherein the structural information employed in (b) comprises information depicting the three-dimensional structure of at least a portion of the parental polypeptides or polypeptides encoded by the parental nucleic acids.

3. The method of claim 1, wherein (b) comprises selecting cross-over points that correspond to overlapping amino acids in the parental polypeptides.

4. The method of claim 1, wherein (b) comprises selecting cross-over points at sites that will preserve selected subunits, domains, or motifs in the parental polypeptides.

5. The method of claim 1, wherein (b) comprises selecting cross-over points at sites chosen to maintain or disrupt one ore more structural relationships between two or more amino acids in the parental polypeptides.

6. The method of claim 1, further comprising performing an additional genetic operation on one or more of the parental or recombinant polypeptides or the parental or recombinant nucleic acids.

7. The method of claim 1, wherein the genetic operation is selected from the group consisting of multiplication, mutation, fragmentation, and ligation.

8. The method of claim 1, wherein the two or more parental polypeptides or parental nucleic acids comprise naturally occurring polypeptides or naturally occurring nucleic acids that encodes a polypeptides.

9. The method of claim 1, wherein (c) comprises computationally assessing three-dimensional structural stability of at least some of the recombinant polypeptides or polypeptides encoded by the recombinant nucleic acids.

10. The method of claim 1, wherein the oligonucleotides identified in (d) are "bridging" oligonucleotides.

11. The method of claim 1, further comprising aligning the two or more parental polypeptides or parental nucleic acids prior to computationally selecting one or more cross-over sites on the sequences.

12. The method of claim 1, wherein the recombinant polypeptides or recombinant nucleic acids that result from the cross-overs comprise contiguous sequences of multiple amino acids or nucleotides from the two or more of the parental polypeptides or parental nucleic acids.

13. A computer program product comprising a machine readable medium on which is provided program instructions for identifying a set of oligonucleotides for use in an in vitro recombination procedure, the program instructions comprising:
    (a) code for providing data identifying sequences of two or more parental polypeptides or parental nucleic acids that encode the polypeptides;
    (b) code for selecting one or more cross-over sites on the sequences based on structural information about the parental polypeptides or polypeptides encoded by the parental nucleic acids; thereby defining one or more recombinant polypeptides or recombinant nucleic acids that result from cross-overs between the parental polypeptides or nucleic acids at the one or more cross-over sites;
    (c) code for selecting at least one of the recombinant polypeptides or recombinant nucleic acids by assessing structural stability of at least some of the recombinant polypeptides or polypeptides encoded by the recombinant nucleic acids; and (d) code for identifying one or more oligonucleotides for in vitro recombination by choosing at least one portion of at least one of the recombinant polypeptides or recombinant nucleic acids selected in (c) which at least one portion corresponds to the one or more oligonucleotides identified for in vitro recombination.

14. The computer program product of claim 13, wherein the structural information employed in (b) comprises information depicting the three-dimensional structure of at least a portion of the parental polypeptides or polypeptides encoded by the parental nucleic acids.

15. The computer program product of claim 13, wherein (b) comprises code for selecting cross-over points that correspond to overlapping amino acids in the parental polypeptides.

16. The computer program product of claim 13, wherein (b) comprises code for selecting cross-over points at sites that will preserve selected subunits, domains, or motifs in the parental polypeptides.

17. The computer program product of claim 13, wherein (b) comprises code for selecting cross-over points at sites chosen to maintain or disrupt one or more structural relationships between two or more amino acids in the parental polypeptides.

18. The computer program of claim 13, further comprising code for performing an additional genetic operation on one or more of the parental or recombinant polypeptides or the parental or recombinant nucleic acids.

19. The computer program product of claim 18, wherein the genetic operation is selected from the group consisting of multiplication, mutation, fragmentation, and ligation.

20. The computer program product of claim 13, wherein at least one of the parental polypeptides or the parental nucleic acids comprise a naturally occurring polypeptide or a naturally occurring nucleic acid that encodes a polypeptide.

21. The computer program product of claim 13, wherein (c) comprises code for assessing three-dimensional structural stability of at least some of the recombinant polypeptides or polypeptides encoded by the recombinant nucleic acids.

22. The computer program product of claim 13, wherein the code for identifying one or more oligonucleotides in (d) identifies "bridging" oligonucleotides.

23. The computer program product of claim 13, further comprising code for aligning the two or more parental polypeptides or parental nucleic acids prior to computationally selecting one or more cross-over sites on the sequences.

24. The computer program product of claim 13, wherein the recombinant polypeptides or recombinant nucleic acids that result from the cross-overs comprise contiguous sequences of multiple amino acids or nucleotides from the two or more of the parental polypeptides or parental nucleic acids.

* * * * *